United States Patent
Sauer et al.

(10) Patent No.: US 8,313,496 B2
(45) Date of Patent: *Nov. 20, 2012

(54) SYSTEM FOR ENDOSCOPIC SUTURING

(75) Inventors: Jude S. Sauer, Pittsford, NY (US);
Michael W. Fitzsimmons, Rochester, NY (US); Mark A. Bovard, Mendon, NY (US)

(73) Assignee: LSI Solutions, Inc., Victor, NY (US)

( * ) Notice: Subject to any disclaimer, the term of this patent is extended or adjusted under 35 U.S.C. 154(b) by 1078 days.

This patent is subject to a terminal disclaimer.

(21) Appl. No.: 10/438,607

(22) Filed: May 15, 2003

(65) Prior Publication Data

US 2004/0034369 A1 Feb. 19, 2004

Related U.S. Application Data

(63) Continuation-in-part of application No. 09/776,431, filed on Feb. 2, 2001, now Pat. No. 6,997,931.

(51) Int. Cl.
*A61B 17/10* (2006.01)
*A61B 17/04* (2006.01)
*A61B 17/12* (2006.01)

(52) U.S. Cl. ........ 606/139; 606/144; 606/148; 606/149; 606/150; 600/104; 600/105; 600/106; 600/107; 604/22

(58) Field of Classification Search .......... 606/139, 606/144, 145, 146, 148, 222, 147, 149, 150; 600/104–108; 604/22
See application file for complete search history.

(56) References Cited

U.S. PATENT DOCUMENTS

| | | | |
|---|---|---|---|
| 4,633,880 A * | 1/1987 | Osypka et al. | 600/374 |
| 4,836,205 A * | 6/1989 | Barrett | 606/144 |
| 4,841,888 A | 6/1989 | Mills et al. | |
| 4,960,410 A * | 10/1990 | Pinchuk | 604/96.01 |
| 5,037,021 A | 8/1991 | Mills et al. | |
| 5,080,663 A | 1/1992 | Mills et al. | |
| 5,167,220 A * | 12/1992 | Brown | 600/157 |
| 5,269,763 A * | 12/1993 | Boehmer et al. | 604/167.04 |
| 5,368,601 A | 11/1994 | Sauer et al. | |
| 5,391,173 A | 2/1995 | Wilk | |
| 5,431,666 A | 7/1995 | Sauer et al. | |
| 5,507,757 A | 4/1996 | Sauer et al. | |

(Continued)

FOREIGN PATENT DOCUMENTS

EP 0 669 103 A1 8/1995

(Continued)

OTHER PUBLICATIONS

Gong, F. et al., "Cutting Thread at Flexible Endoscopy", Gastrointestinal Endoscopy, vol. 44, No. 4, 667-679 (1996).

(Continued)

*Primary Examiner* — Gary Jackson
*Assistant Examiner* — Michael Mendoza
(74) *Attorney, Agent, or Firm* — Kenneth J. Lukacher

(57) ABSTRACT

A system for endoscopic suturing is provided having an endoscope, such as a gastroscope, with a distal end locatable in the body of a patient and a flexible shaft extending to the distal end, a flexible accessory tube coupled to the endoscope to flex relative to the endoscope's shaft, and a tip coupled to the shaft of the endoscope having an opening through which one end of the accessory tube is received. Tissue suturing and suture securing instruments are provided each having a sufficiently flexible shaft locatable through the accessory tube.

40 Claims, 92 Drawing Sheets

U.S. PATENT DOCUMENTS

| | | | |
|---|---|---|---|
| 5,520,702 A | | 5/1996 | Sauer et al. |
| 5,562,686 A | | 10/1996 | Sauer et al. |
| 5,584,861 A | | 12/1996 | Swain et al. |
| 5,626,588 A | | 5/1997 | Sauer et al. |
| 5,626,590 A | | 5/1997 | Wilk |
| 5,643,289 A | | 7/1997 | Sauer et al. |
| 5,669,917 A | | 9/1997 | Sauer et al. |
| 5,722,990 A | | 3/1998 | Sugarbaker et al. |
| 5,755,730 A | | 5/1998 | Swain et al. |
| 5,766,183 A | * | 6/1998 | Sauer ............................ 606/139 |
| 5,792,153 A | | 8/1998 | Swain et al. |
| 5,810,805 A | | 9/1998 | Sutcu et al. |
| 5,810,849 A | * | 9/1998 | Kontos .......................... 606/144 |
| 5,817,013 A | * | 10/1998 | Ginn et al. ................... 600/114 |
| 5,855,585 A | * | 1/1999 | Kontos .......................... 606/144 |
| 5,876,411 A | * | 3/1999 | Kontos .......................... 606/144 |
| 5,906,606 A | * | 5/1999 | Chee et al. ................... 604/527 |
| 5,908,429 A | * | 6/1999 | Yoon ............................. 606/144 |
| 5,910,105 A | * | 6/1999 | Swain et al. ................. 600/131 |
| 5,919,199 A | * | 7/1999 | Kelly et al. .................. 606/139 |
| 5,954,731 A | | 9/1999 | Yoon |
| 6,022,313 A | * | 2/2000 | Ginn et al. ................... 600/114 |
| 6,068,648 A | * | 5/2000 | Cole et al. .................... 606/232 |
| 6,071,233 A | * | 6/2000 | Ishikawa et al. ............. 600/104 |
| 6,077,279 A | * | 6/2000 | Kontos .......................... 606/148 |
| 6,533,796 B1 | * | 3/2003 | Sauer et al. ................... 606/144 |
| 6,641,592 B1 | * | 11/2003 | Sauer et al. ................... 606/144 |
| 6,808,491 B2 | * | 10/2004 | Kortenbach et al. .......... 600/104 |
| 6,997,931 B2 | * | 2/2006 | Sauer et al. ................... 606/139 |

FOREIGN PATENT DOCUMENTS

| | | |
|---|---|---|
| EP | 0 568 098 B1 | 10/1997 |
| EP | 0 669 102 B1 | 10/1998 |

OTHER PUBLICATIONS

Kadirkamanathan, S. et al., "Anti-reflux Operations at Flexible Endoscopy Using Endoluminal Stitching Techniques: An Experimental Study", Gastrointestinal Endoscopy, vol. 44, No. 2, 144-162 (1996).

Swain, C. et al., "An Endoscopically Deliverable Tissue-Transfixing Device for Securing Biosensors in the Gastrointestinal Tract", Gastrointestinal Endoscopy, vol. 40, No. 6, 730-737 (1994).

Rich, P., "Simple GERD Treatment Offers New Alternative", The Medical Post, vol. 35, No. 11, 1-3 (1999).

Filipi, C., "Totally Endoscopic Antireflux Surgery: A Clinical Trial of the BARD Endoscopic Sewing Device", Creighton Univ. Cardiothoracic Update, vol. 1, No. 6, 1-3 (1998).

Brochure entitled "SEW-RIGHT SR 5, The Single Squeeze Suturing Device", LSI Solutions, Copyright 2000.

Brochure entitled "Ti-KNOT TK 5, The Device to Instantly Secure and Trim Suture", LSI Solutions, Copyright 2000.

Brochure entitled "The EndoCinch Procedure, BARD's Unique New Endoscopic Suturing System for treating Symptomatic GERD".

* cited by examiner

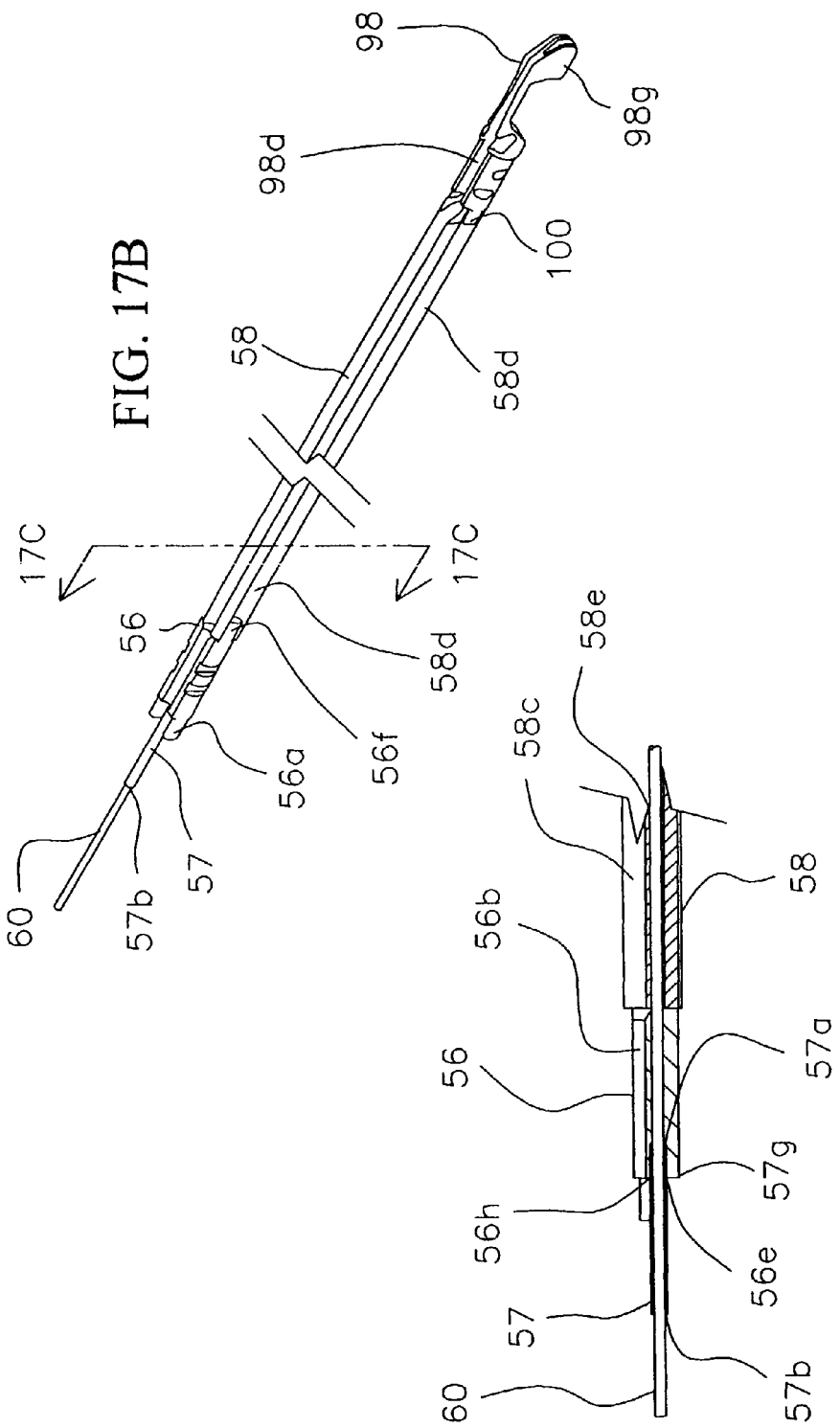

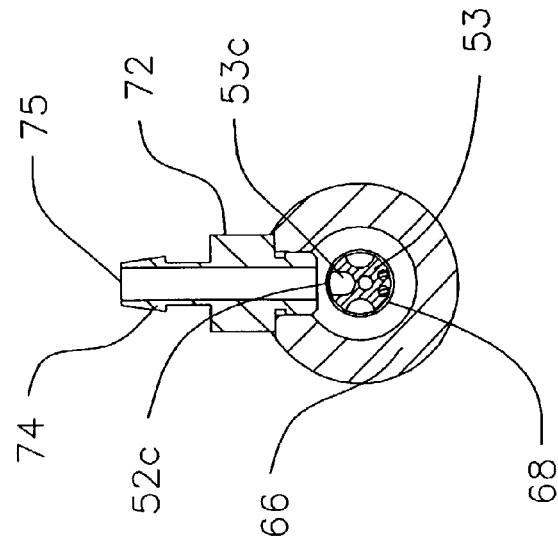
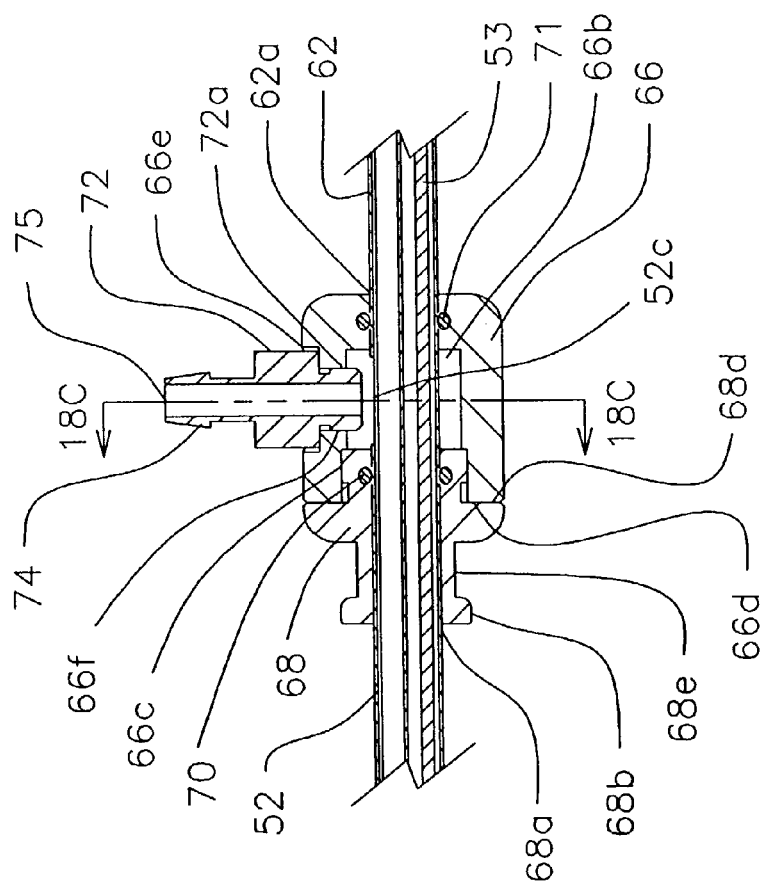
FIG. 18C
FIG. 18B

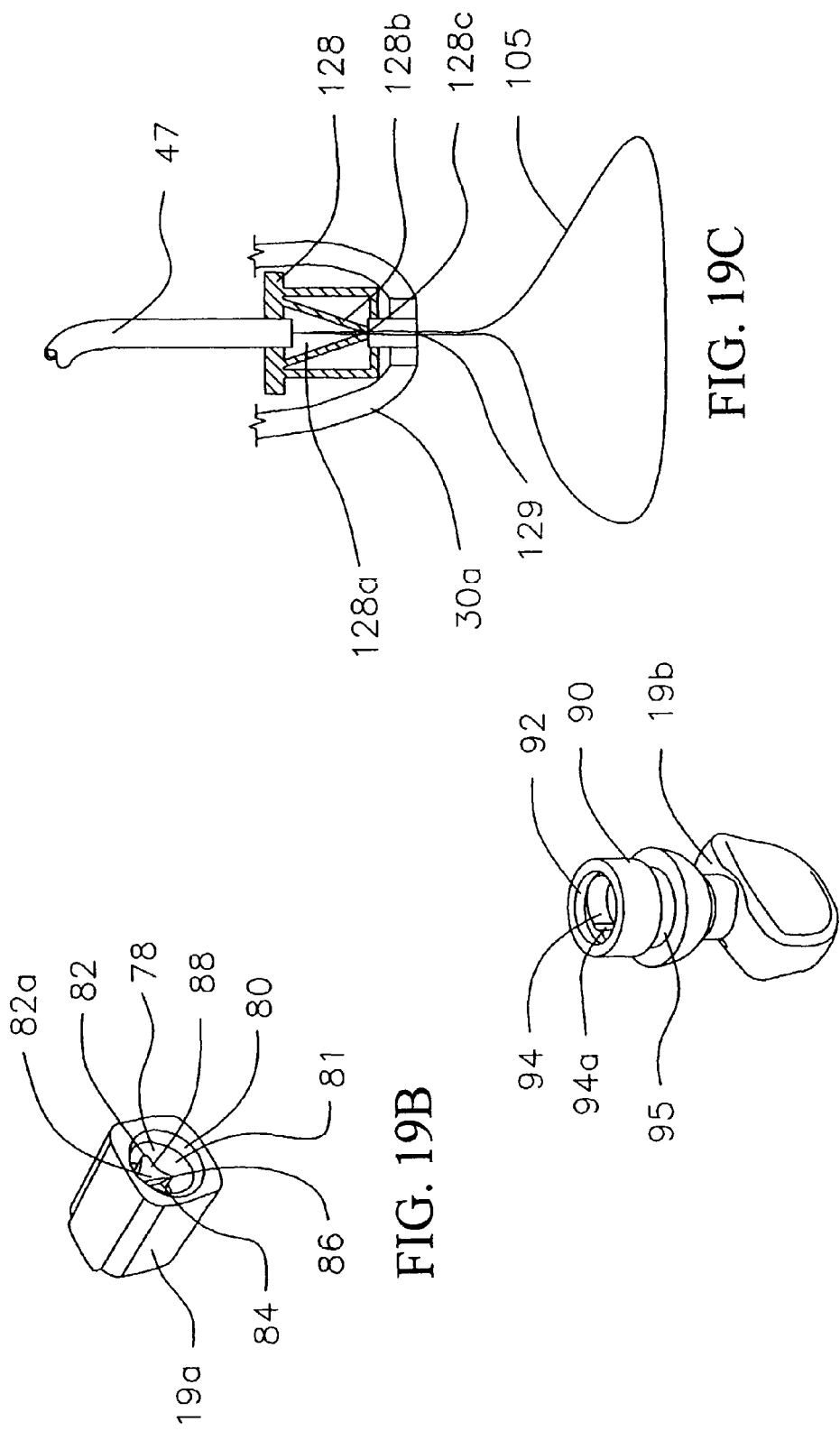

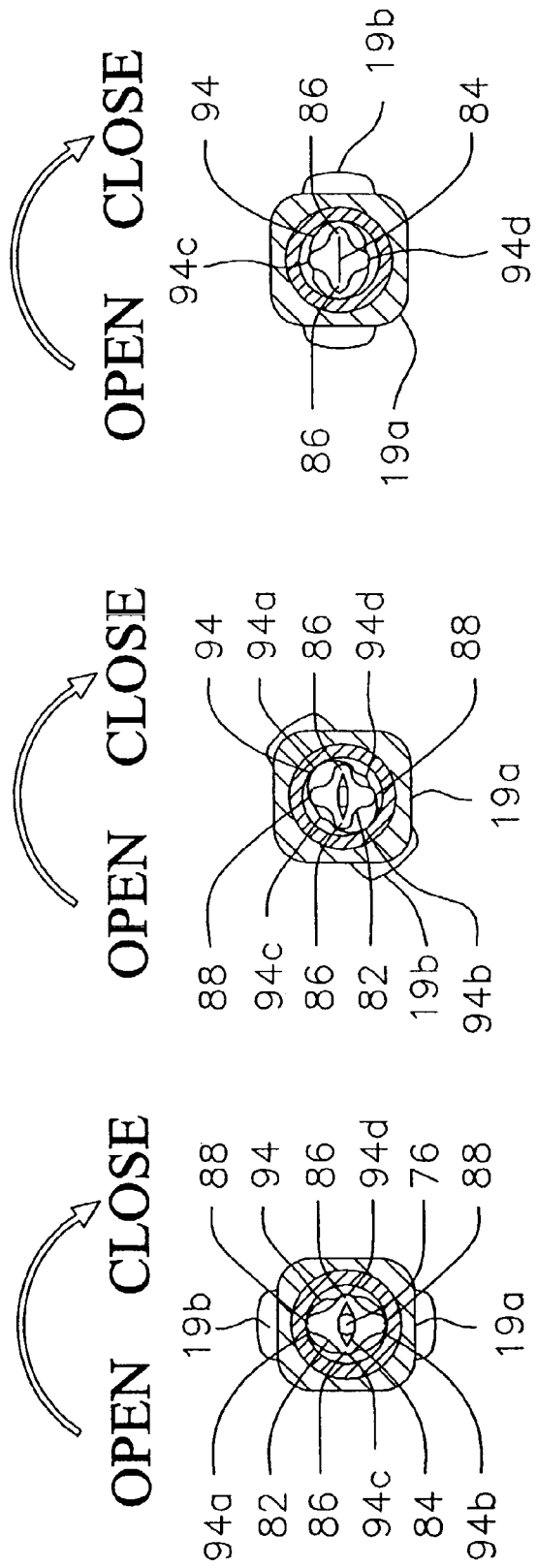

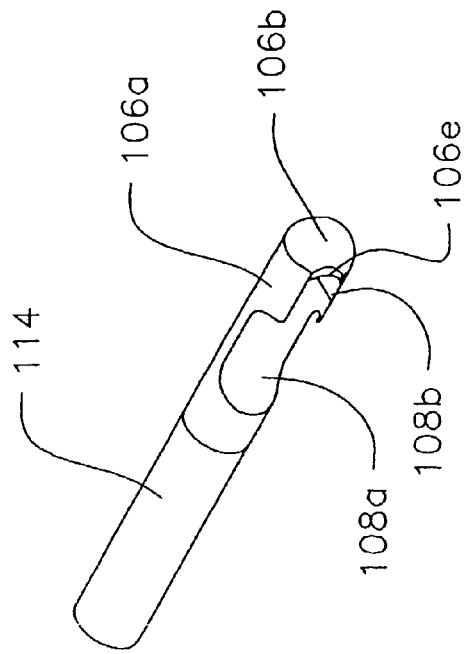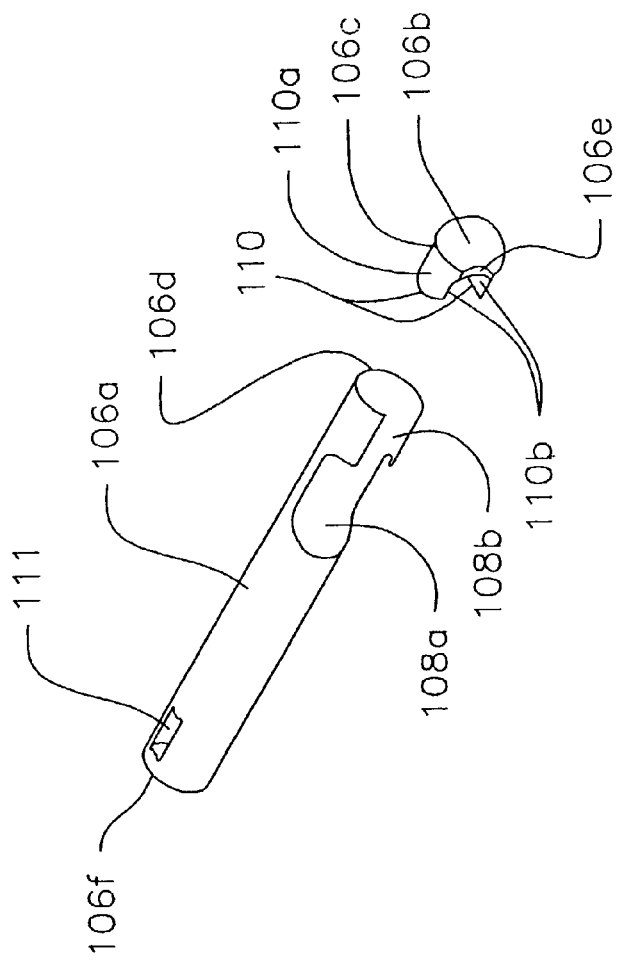

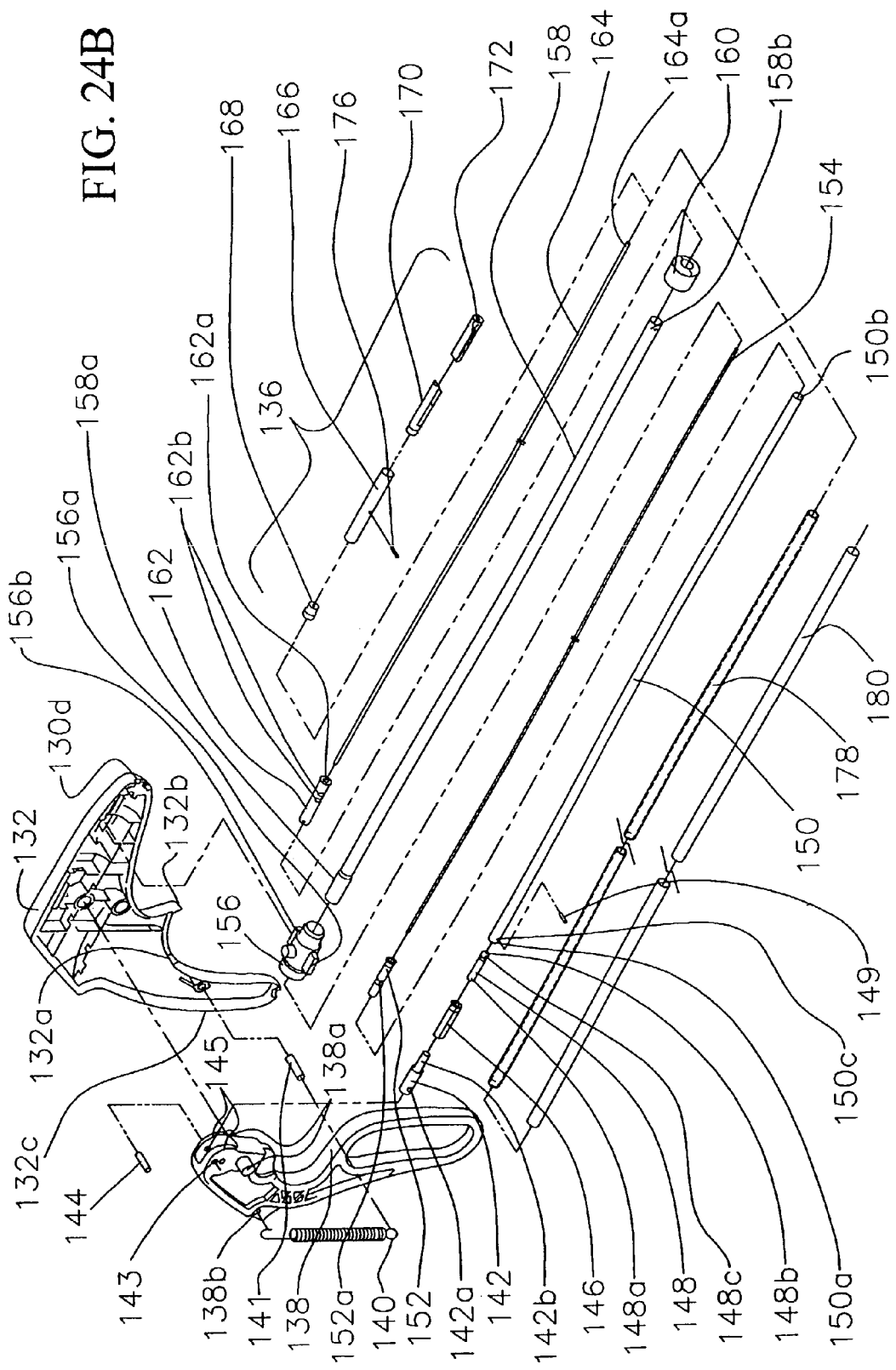

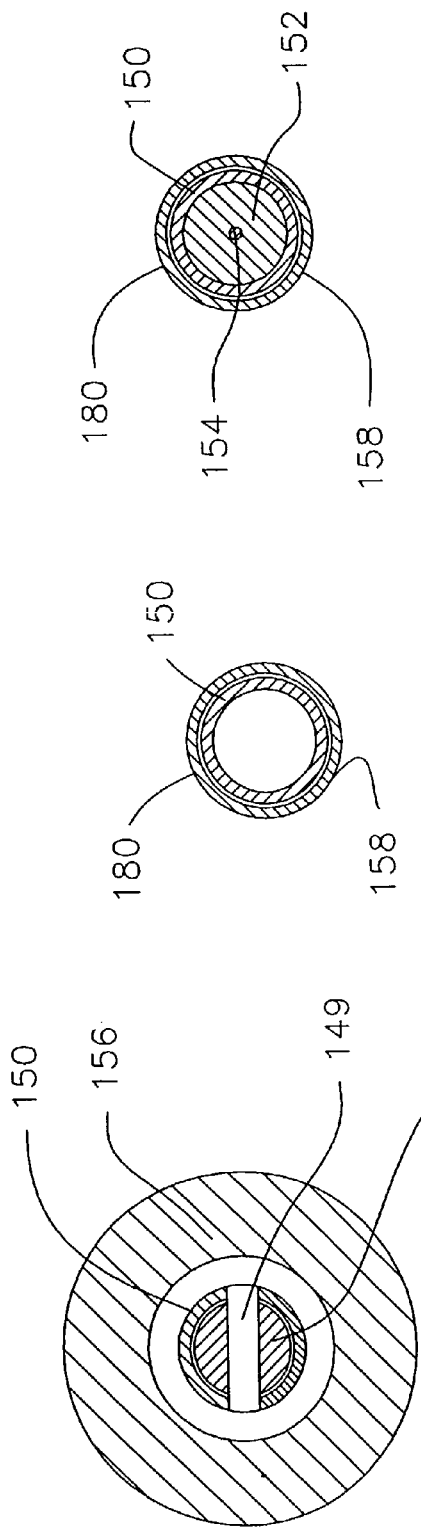
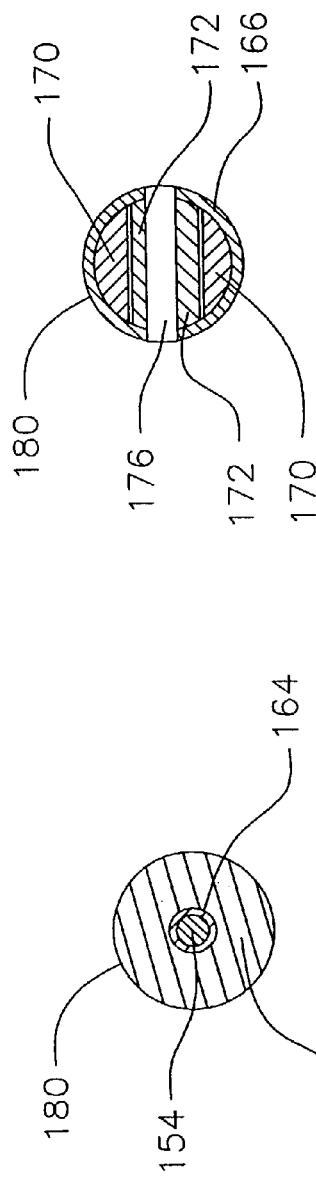
FIG. 24C
FIG. 24D
FIG. 24E
FIG. 24F
FIG. 24G

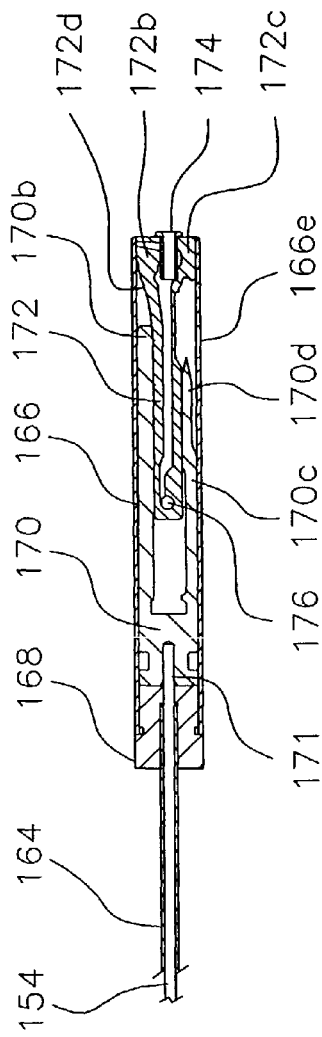
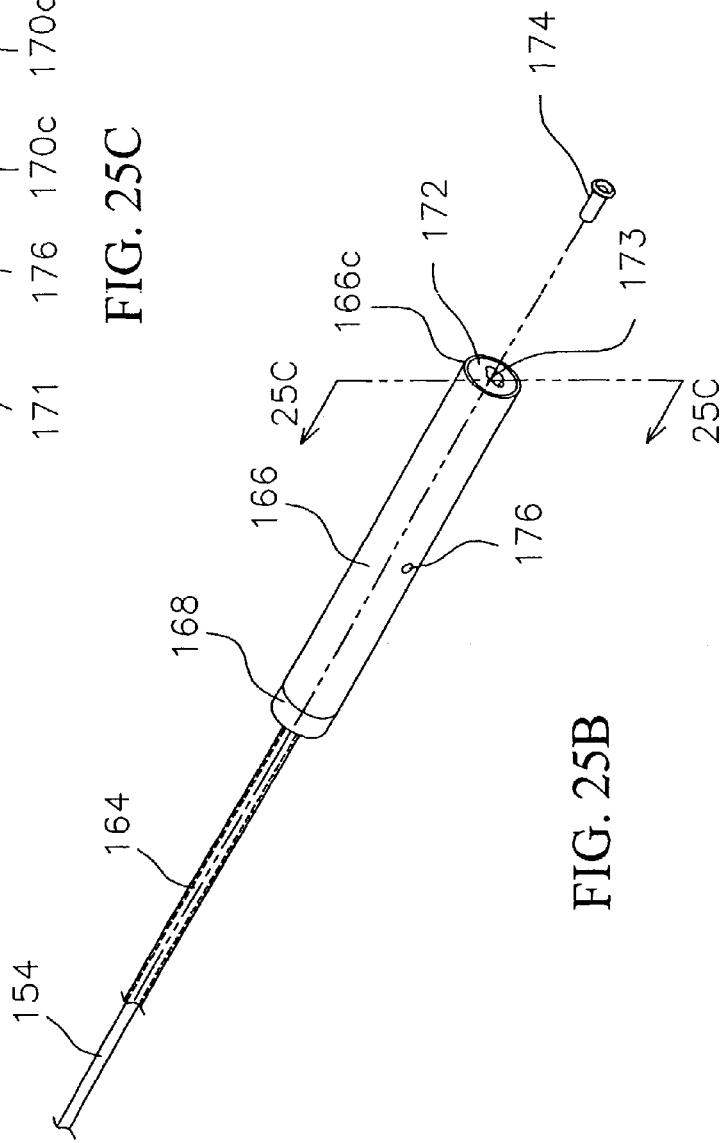
FIG. 25C
FIG. 25B

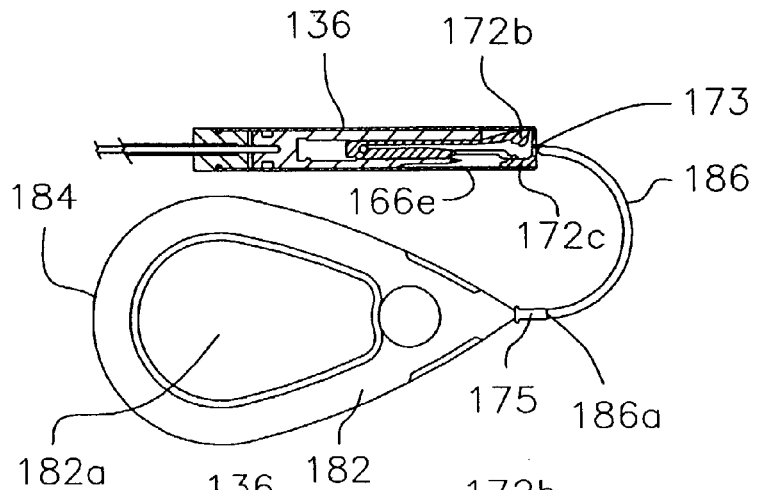
FIG. 26A
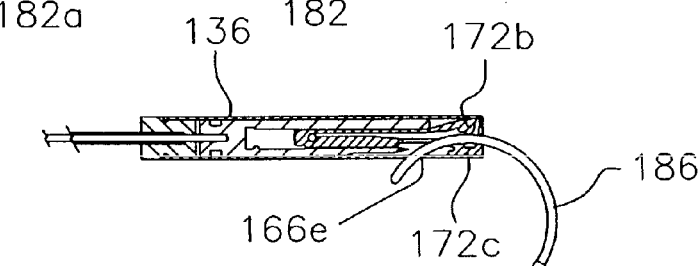
FIG. 26B
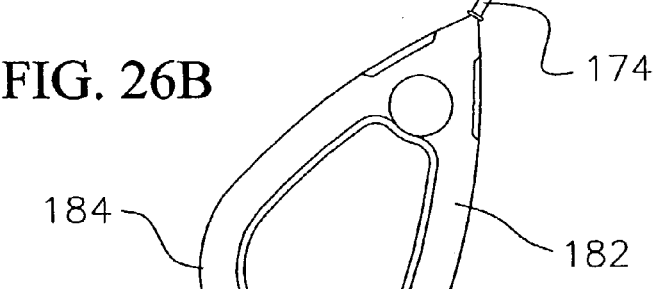
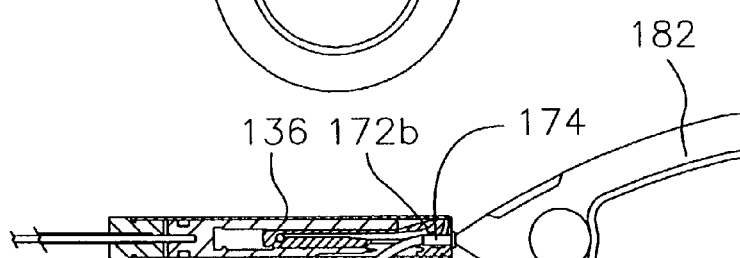
FIG. 26C

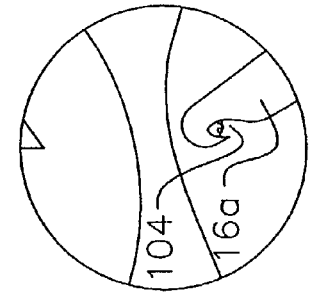
FIG. 28A
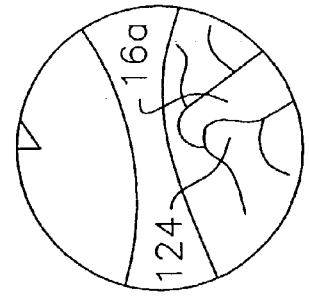
FIG. 28B
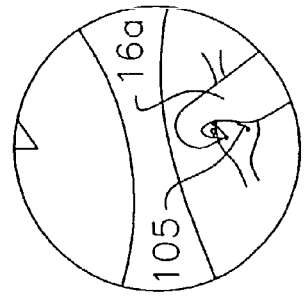
FIG. 28C
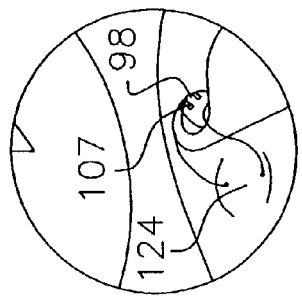
FIG. 28D
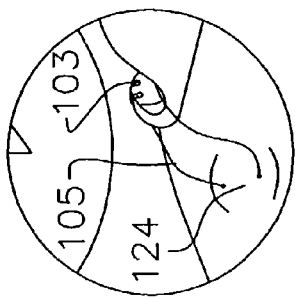
FIG. 28E
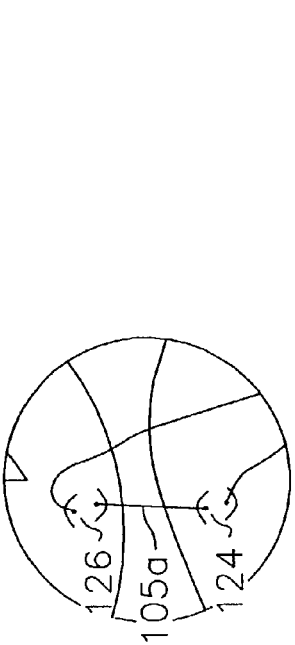
FIG. 28F
FIG. 28G
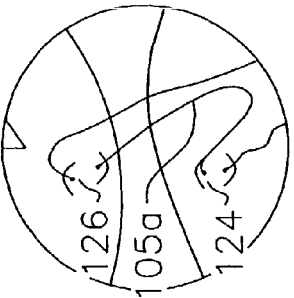
FIG. 28H
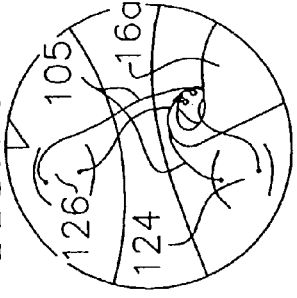
FIG. 28I
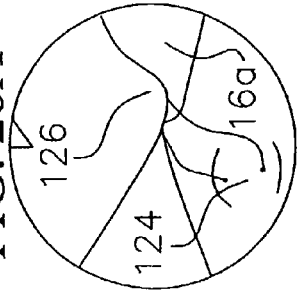
FIG. 28J
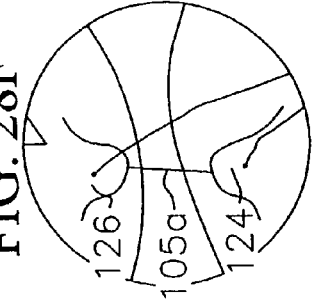
FIG. 28K
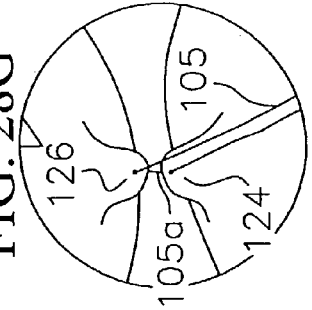
FIG. 28L
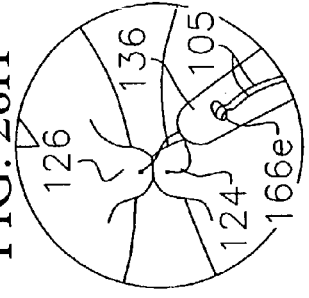
FIG. 28M
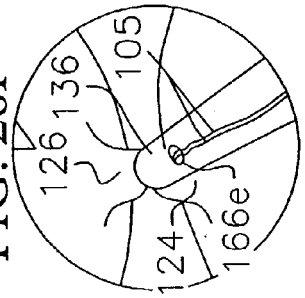
FIG. 28N
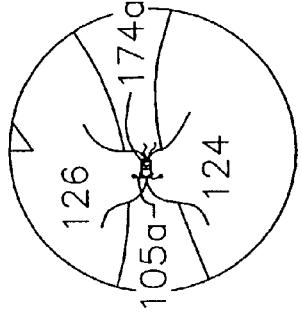

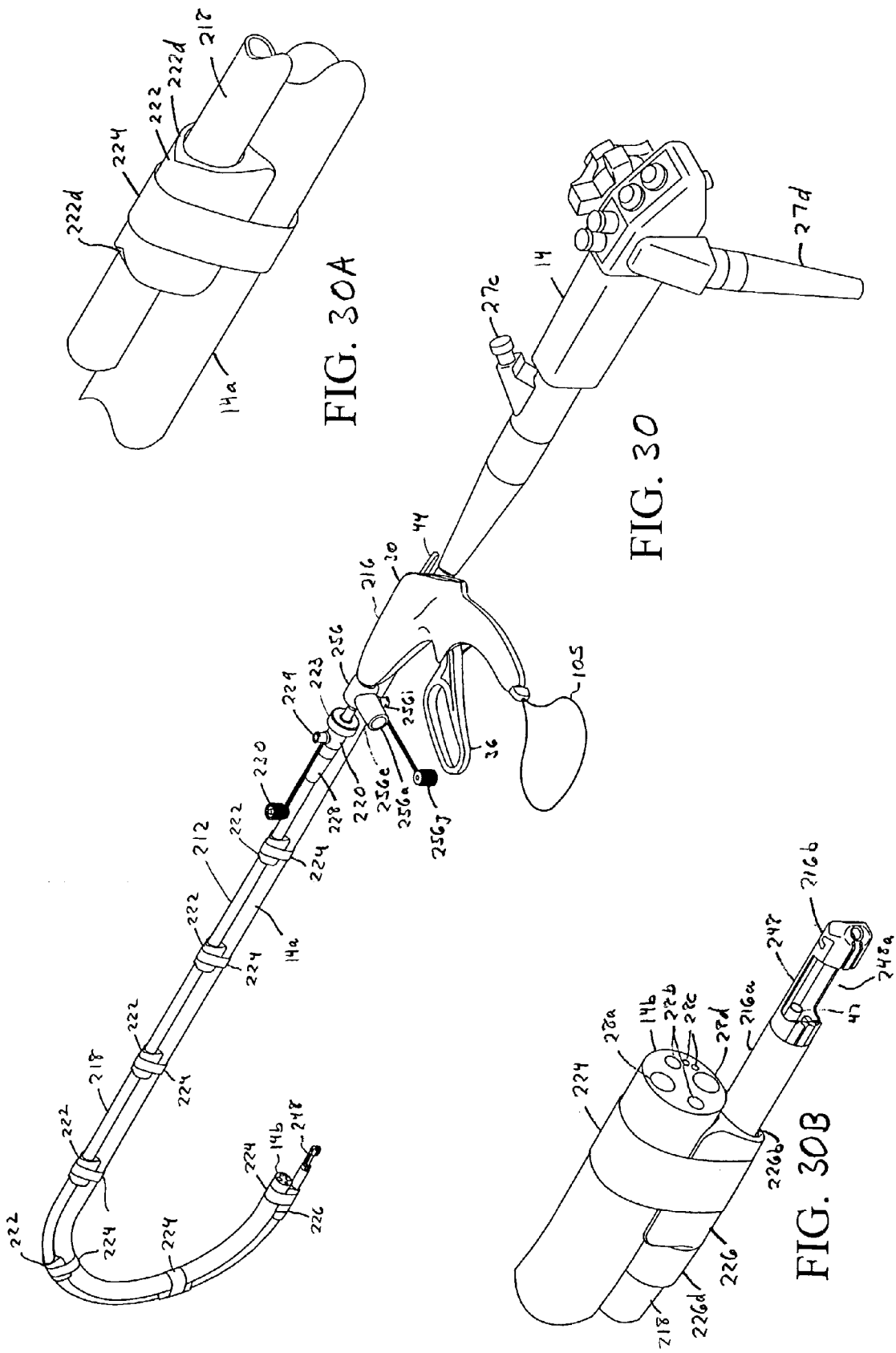

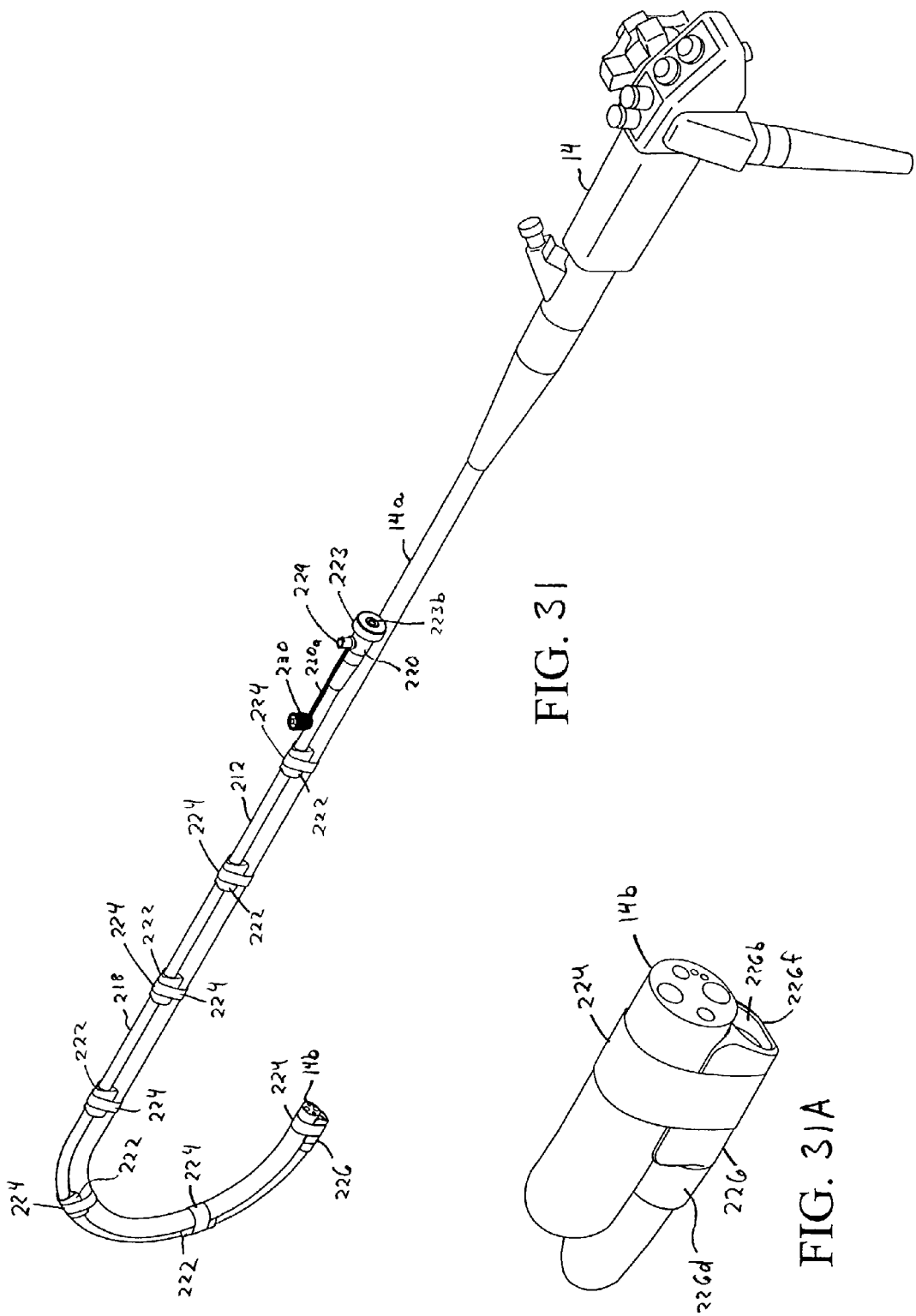

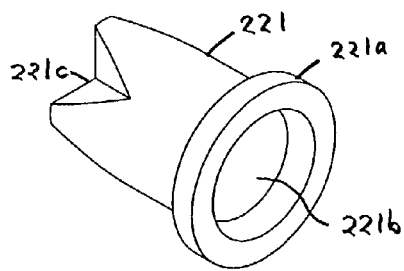
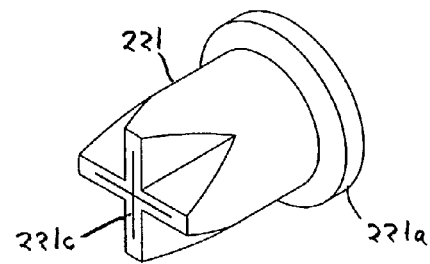
FIG. 33        FIG. 33A
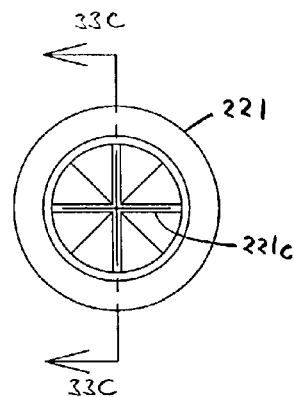
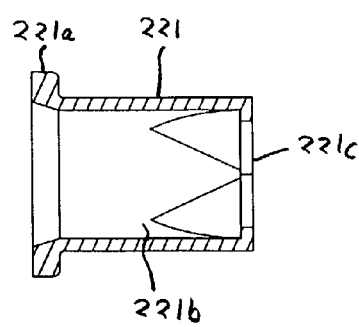
FIG. 33B        FIG. 33C

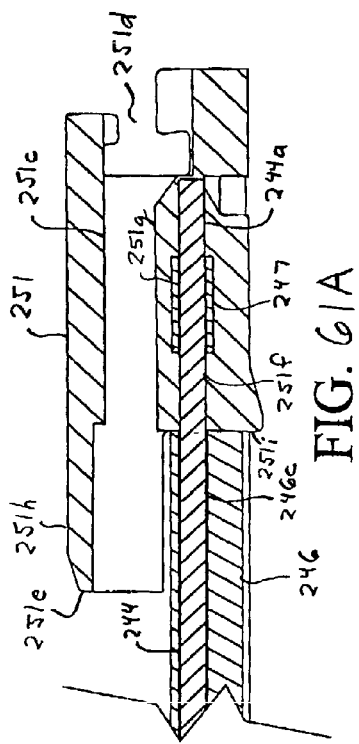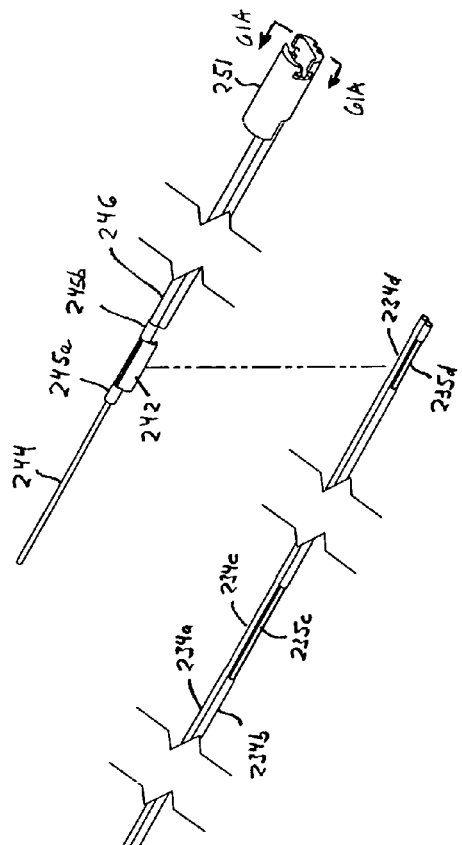

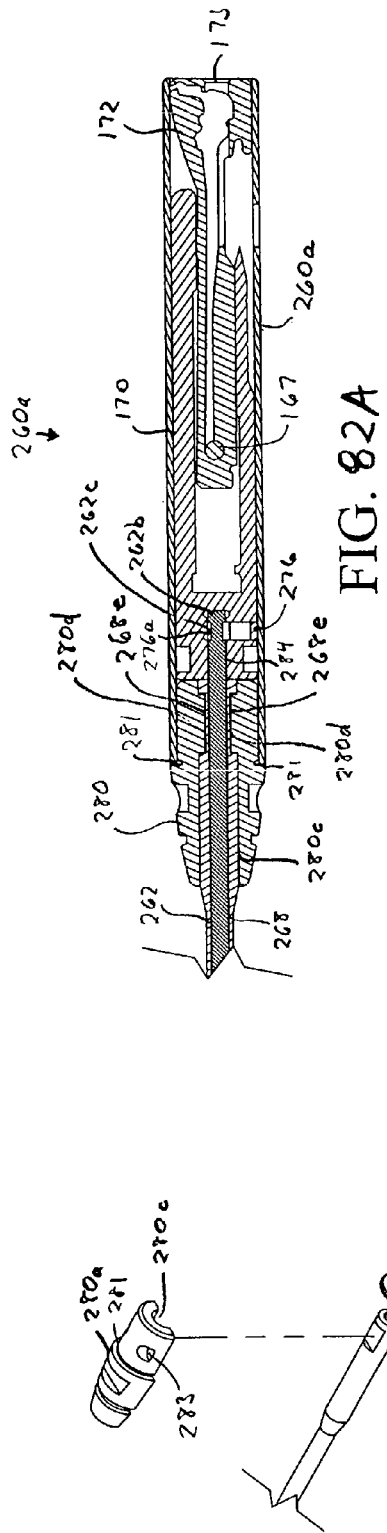
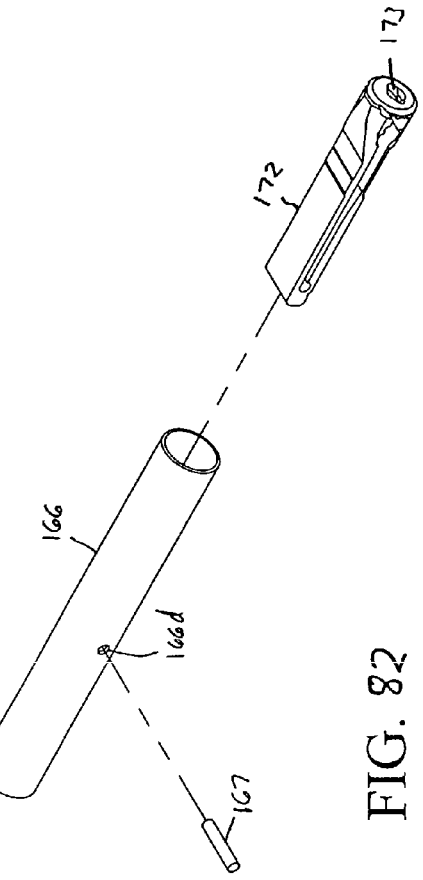
FIG. 82A
FIG. 82

SYSTEM FOR ENDOSCOPIC SUTURING

CROSS-REFERENCE TO RELATED APPLICATIONS

This application is a continuation-in-part of U.S. patent application Ser. No. 09/776,431, filed Feb. 2, 2001 now U.S. Pat. No. 6,997,931, which is herein incorporated by reference.

FIELD OF THE INVENTION

The present invention relates to a system (and method) for endoscopic suturing, and in particular to a system for suturing through an accessory tube coupled to a flexible endoscope, which may be placed in the stomach through mouth and the esophagus of a patient utilizing a tissue suturing instrument and a suture securing instrument. The invention is suitable, for example, for applying at least one suture in the soft tissue lining of the stomach for different procedures such as gastroplasty, fundoplication, anterior gastropexy, or other procedures requiring suturing in the stomach, without the need for laparotomy or laparoscopy.

BACKGROUND OF THE INVENTION

Application of sutures in the gastrointestinal tract is required for several different types of medical procedures, for example, transoral endoscopic valvuloplasty for gastroesophageal reflux disease, gastroplasty, fundoplication, anterior gastropexy, suturing esophageal perforations, or closure of esophageal side of tracheo-esophageal fistula. Traditionally, these procedures were performed by physicians, such as gastroenterologist or surgeons, either by laparoscopy or open surgical techniques. Such procedures are invasive, as laparoscopy requires small access incision(s) made in the body of the patient through which a laparoscope and other surgical enabling tools are provided, while open surgical techniques are traditionally invasive and can have complications and long patient recovery periods.

The solution to these problems is to perform these medical procedures through the gastroesophageal tract via the mouth or other naturally occurring orifices. Already available flexible endoscopes, commonly called gastroscopes, can be provided through the gastroesophageal tract and enable illumination and visualization of tissue along the gastroesophageal tract on a video display for diagnostic purposes. Although gastroscopes often have a working channel to a port at the distal end of the gastroscope through which a biopsy tool may be provided to obtain tissue samples, they are not currently designed or typically large enough to be capable of applying sutures in tissue.

U.S. Pat. No. 5,792,153 describes a sewing device coupled to the distal end of an endoscope, which enables suturing in the gastroesophageal tract of a patient. The sewing device has a single hollow needle mounted in the biopsy channel of the endoscope, and a wire extending through the needle to a T-shaped tag having one end of a suture thread which extends outside of the patient. To apply a suture, suction is applied to a U-shaped opening of the sewing device via another channel of the endoscope to suck a layer (or fold) of tissue into the U-shaped opening, the needle in the biopsy channel is then pushed through the tissue, and then the wire is pushed and rotated to position the tag in a chamber along one side of the U-shaped opening. This rotates the tag into a position which captures the tag and the suture end in this chamber, and the needle and wire are retracted to the other side of the U-shaped opening. The endoscope and its coupled sewing device are removed from the patient, leaving a loop of suture through the tissue which must then be secured and closed. The patent also provides another sewing device at the end of an endoscope which enables multiple stitches in tissue with the same needle and suture thread. The sewing device of U.S. Pat. No. 5,792,153 to apply a single stitch is manufactured by Laboratories BARD S. A. of Voisinsle Bretonneux, France, and described in Kadirkamanathan et al., Gastrointestinal Endoscopy, August 1996, Vol. 44, No. 2, pp.144-162.

Once the suture thread is placed through the tissue with the sewing device of U.S. Pat. No. 5,792,153, the suture thread must be secured and then cut close to the tissue. One device also manufactured by Laboratories BARD S. A., and described in U.S. Pat. No. 5,755,730, provides for securing and cutting suture using an endoscope. The device passes through the biopsy channel of the endoscope is order to push a knot made by a physician or surgeon, which ties the ends of a loop of suture thread together, down to the tissue, and then a cutting member cut the ends of the suture. Since the sewing device of U.S. Pat. No. 5,792,153 does not allow normal use of its biopsy channel of the endoscope upon which the sewing device is mounted, a second endoscope must be used to secure and cut the suture through its biopsy channel using the device described in U.S. Pat. No. 5,755,730. This results in multiple passes of endoscopes back and forth through the gastroesophageal tract, especially if single sutures are each applied and secured at multiple locations in tissue. To reduce possible damage to the esophageal tract and to facilitate multiple instrument insertions, an overtube is first placed in the esophageal tract and each endoscope is inserted and removed through the overtube. However, the overtube may be uncomfortable to patients, and can cause complications, such as mucosal tears in the esophagus. Accordingly, it would be desirable to provide a system for suturing which does not require different endoscopes for suture placement and suture securing, and moreover can apply and secure multiple single sutures in tissue with the single insertion of a flexible endoscope, i.e., gastroscope without requiring an overtube.

Other sewing devices or machines mounted on the end of an endoscope are described in U.S. Pat. Nos. 5,037,021 and 4,841,888. These sewing devices similarly utilize two channels of the endoscope, one to suction tissue into a slot of the device and the other to advance and retract a wire coupled to needle through the tissue. The needle has a suture loop at its tip such that when the needle is advanced through the slot it extends into a chamber where a hook or U-shaped member pivots to retain the suture loop when the needle retracts. A wire is coupled to the hook and extends through the same channel where suction is provided, such that movement of this wire pivot the hook to capture the suture thread. Removal of the sewing device then leaves a loop of suture through the tissue.

A further sewing device is described in U.S. Pat. No. 5,080,663 and also utilizes an operating device having tubes in a tubular sheath, such as endoscopic means, to provide suction to a slot in the device to capture a double fold of tissue and two wires extending through such tubes. One wire advances and retracts a needle having a tag with suture at its tip through tissue and the other wire controls capture of a tag at the other side of the opening. The patent provides for applying a sensor or transmitter in the body of a patient, such as the stomach. This sewing device is also described in Swain et al., An endoscopically deliverable tissue-transfixing device for securing biosensors in the gastrointestinal tract, Gastrointestinal Endoscopy, November/December 1994, Vol. 40, No. 6, pp. 730-737.

Like the sewing devices of U.S. Pat. No. 5,792,153, those described in U.S. Pat. Nos. 5,037,021 4,841,888, and 5,080,663 have the same drawbacks as these devices are also mounted on an endoscope. Moreover, mounting on an endoscope limits the use of the endoscope for full visualization of tissue, as the sewing device partially obstructs the viewing area at the distal end of the endoscope. Further the use of the biopsy or working channel of an endoscope for needle placement does not allow use of the channel for other purposes, such as obtaining a biopsy. Accordingly, it would further be desirable to provide for suturing with a flexible endoscope which allows for more complete traditional use of the endoscope.

SUMMARY OF THE INVENTION

Accordingly, it is the principal object of the present invention to provide an improved system for endoscopic suturing that overcomes the drawbacks of the prior art.

It is another object of the present invention to provide an improved system for endoscopic suturing which allows single insertion of an endoscope and accessory tube assembly in the gastrointestinal tract of a patient through which multiple instruments for suturing and securing sutures can be used without removal of the endoscope between suturing and suture securing operations.

It is a further object of the present invention to provide an improved system for endoscopic suturing which provides a channel to sew through independent of an endoscope.

Yet a further object of the present invention is to provide an improved system for endoscopic suturing in which a suturing instrument separate from an endoscope can utilize suction to capture tissue to be sutured.

A still further object of the present invention is to provide an improved system for remote suturing which can readily be adapted to different types of flexible endoscopes to provide an external accessory tube through which medical or surgical instruments can pass.

A still further object of the present invention is to provide an improved system for endoscopic suturing which utilizes one or more instruments which each have a sufficient flexible shaft to pass through an external flexible accessory tube attached to a flexible endoscope.

A further object of the present invention is to provide an improved system for endoscopic suturing and suture securing instruments having shafts with enhanced flexibility.

Yet a further object of the present invention is to provide an improved system for endoscopic suturing in which remote viewing with an endoscope of suture and suture securing operations is provided in the stomach without hindering endoscope functionality.

Briefly described, a preferred embodiment of this system embodying the invention includes an endoscope, such as a gastroscope, having a distal end locatable in the body of a patient, such as in the gastrointestinal or gastroesophageal tract, and a flexible shaft extending to the distal end, a flexible accessory tube coupled to the endoscope to be movable with flexing of the endoscope's shaft, and an attachment tip coupled to the shaft of the endoscope having an opening through which one end of the accessory tube is received. The accessory tube is coupled to the shaft of the endoscope with multiple tube guides enabling the accessory tube to slide through the tube guides in response to bending of the endoscope's shaft. The accessory tube has a cannula with a sealable opening through which an instrument may pass into the accessory tube. The system includes a tissue suturing instrument having a partially flexible shaft locatable through the accessory tube, and a tissue engaging end coupled to the shaft which is viewable by the endoscope at its distal end when the instrument is fully inserted through the accessory tube. The tissue engaging end has a vacuum sleeve enabling suction to be selectably applied at the tissue engaging end to capture tissue in a gap of a sew tip through an opening in the vacuum sleeve. Suction is applied via a vacuum connection assembly to a channel which extends down the shaft to the sew tip. A valve is provided to close one end of the suture carrying channel to enable such suction at the sew tip. Two needles are provided which extend through the shaft of the suturing instrument. The shaft has a rigid section and then a flexible section coupled to the distal tissue engaging end of the instrument, in which each section has a guide member through which needles and suture pass to the distal tissue engaging end. Each needle is separately actuated into the gap of the sew tip through suctioned tissue to capture a ferrule having one end of a loop of suture. The system further includes a suture securing instrument having a partially flexible shaft locatable through the accessory tube, and a distal tissue engaging end coupled to the shaft which is viewable by the endoscope at its distal end when the instrument is fully inserted through the accessory tube. After removal of the suturing instrument from the accessory tube, a loop of suture extends through the tissue through the accessory tube, the suture securing instrument receives the free ends of the loop of suture at its distal end through a sleeve member, and the suture securing instrument is then inserted through the accessory tube to the location of the suture in the tissue. The suture securing instrument has a housing with a pivotally mounted actuator member, and a shaft with a rigid section coupled to the housing and then a flexible section to the instrument's distal end. A drive wire coupled to the actuator member extends through the shaft to the instrument to actuate crimping of the sleeve member to retain the suture closed and cutting of the free ends of the suture. The endoscope enables an operator, such as a surgeon, gastroenterologist, or other skilled physician, to view the engaging end of the suturing instrument for selecting placement of the suture through tissue, and of the distal end of the suture securing instrument to secure the suture closed.

Another embodiment of the suturing instrument is provided having a shaft with enhanced flexibility. Such flexibility is provided by needle carrying tubes for each of the needles which extend through a portion of the shaft's rigid section and then flexible section, where the needle carrying tubes are coupled by a cable or wire to the distal tissue engaging end. Needles undulate in diameter through at least part of the flexible section prior to entering channels along the distal tissue engaging end. Slots along the sew tip extend through the gap to assist in conveying suction (i.e., negative air pressure) along the gap when such suction is applied down the shaft to the sew tip of the distal tissue engaging end. A rigid tube of the instrument defines the extent of the rigid section, while such rigid tube is coupled to a flexible body or tube which defines the flexible portion of the shaft to the distal tissue engaging end. The enhanced flexibility of the shaft further facilitates the ability of the shaft to flex in the accessory tube in accordance with such flexures of the accessory tube following flexures of the endoscope's shaft.

Another embodiment of the suture securing instrument is also provided having a housing with a pivotally mounted actuator member, and a flexible tube which extends from the housing to the distal end of the instrument, a drive wire is coupled to the actuator member and extends through said flexible tube to actuate crimping of the sleeve member and cutting of free ends of the suture at the distal end. The flexible tube is fixed to the housing and to the distal end, and the wire is extendable and retractable through the flexible tube in response to pivoting of the actuator member. The flexible tube further has successive regions of reduced diameter from the housing to the distal end of the instrument to enhance flexibility of the tube. An overtube extends from the housing along part of the flexible tube. The overtube and flexible tube define the shaft of the instrument. The shaft of the suture securing instrument of this embodiment provides enhanced flexibility to further facilitate the shaft to flex in the accessory tube in accordance with such flexures of the accessory tube following flexures of the endoscope's shaft A method embodying the present invention is also provided having the steps of: locating an endoscope, such as a gastroscope, coupled to an accessory tube through the gastrointestinal or gastroesophageal tract of a patient; inserting a suturing instrument through the accessory tube to place two ends of a loop of suture through tissue of the gastrointestinal or gastroesophageal tract; removing the suturing instrument to leave a loop of suture in the tissue having two free ends extending from the accessory tube; inserting a suture securing instrument having a distal end with a sleeve member through which the free ends of the suture loop are drawn to the suture in the tissue to crimp the sleeve member and cut the free ends of the suture; and removing the suture securing instrument from the accessory tube.

Optionally, the suturing instrument and suture securing instrument may be used without the accessory tube when an internal working of biopsy channel is provided in the endoscope that permits the passage of the shaft of the suturing instrument and suture securing instrument, respectively.

The following description refers to the endoscope as a gastroscope for purposes of illustration. Other types of endoscopes may be used in the system and method.

BRIEF DESCRIPTION OF THE DRAWINGS

The foregoing objects, features and advantages of the invention will become more apparent from a reading of the following description in connection with the accompanying drawings, in which:

FIG. 1A is a partial view of endoscope shaft of FIGS. 1 and 2 showing the attachment of a tube guide to the endoscope while enabling the accessory tube to be slidable through the tube guide in response to flexing of the endoscope's shaft;

FIG. 1B is an expanded view of the distal end of the system of FIG. 1;

FIG. 2A is an expanded view of the distal end of the system of FIG. 2;

FIG. 10A is a perspective view of the retainer member of the suturing instrument of FIGS. 9 and 10;

FIG. 10B is a side view of the cam member of the suturing instrument of FIGS. 9 and 10;

FIG. 17B is a perspective view showing the connection of the coupler member, sew tip, and the guide member of FIG. 17A;

FIG. 17C is a cross-sectional view along lines 17C-17C of the FIG. 17B;

FIG. 18B is a cross-sectional view of the vacuum connection assembly along lines 18B-18B of FIG. 18;

FIG. 18C is a cross-sectional view along lines 18C-18C of the suturing instrument of FIG. 9;

FIGS. 19A and 19B are perspective view of the valve seat and valve knob of the valve of the suturing instrument of FIGS. 9 and 10;

FIG. 19C is schematic diagram of an alternative valve for the suturing instrument of FIGS. 9 and 10;

FIGS. 20A, 20B, and 20C illustrate the valve seat in response to the rotation of the valve knob from an open state to a closed state to seal one end of the suture tube of the suturing instrument of FIGS. 9 and 10;

FIGS. 21C and 21D are perspective views showing assembly of the sleeve of FIGS. 21 and 21A;

FIG. 24B is an exploded view of the suture securing instrument of FIG. 24 in which the right cover of the housing is removed;

FIGS. 24C is a cross-sectional view through lines 24C-24C of the suture securing instrument of FIG. 24A.

FIGS. 24D is a cross-sectional view through lines 24D-24D of the suture securing instrument of FIG. 24A.

FIGS. 24E is a cross-sectional view through lines 24E-24E of the suture securing instrument of FIG. 24A.

FIGS. 24F is a cross-sectional view through lines 24F-24F of the suture securing instrument of FIG. 24A.

FIG. 24G is a cross-sectional view through lines 24G-24G of the suture securing instrument of FIG. 24A.

FIGS. 25A and 25B illustrate the assembly of the distal end of the suture securing instrument of FIG. 24;

FIG. 25C is a cross-section of the distal end of the suture securing instrument along lines 25C-25C of FIG. 25B;

FIGS. 26A-26D illustrate the use of a loading device for placement of a sleeve member into the distal end of the suture securing instrument of FIG. 24, in which FIG. 26D further illustrates a guide wire loop for loading of suture in the instrument;

FIGS. 28A-28N represent an example of the view through the endoscope for applying a suture by the suturing instrument of the system of FIG. 1 and then secured in place by a suture securing instrument of the system;

FIG. 30 is a perspective view of the system in accordance with another embodiment of the accessory tube and another embodiment of the suturing instrument of the present invention;

FIG. 30A is a partial view of the shaft of the endoscope of FIG. 30 showing the attachment of one of the tube guides to the shaft while enabling the accessory tube to be slidible through the tube guide in response to flexing of the endoscope's shaft;

FIG. 30B is an expanded view of the distal end of the system of FIG. 30;

FIG. 31 is a perspective view of the system of FIG. 30 with the suture instrument of the system removed;

FIG. 31A is an expanded view of the distal end of the system of FIG. 31;

FIG. 33 is a front perspective view of the sealing element in the cannula of the accessory tube of FIGS. 30-32;

FIG. 33A is a back perspective view of the sealing element in the cannula of the accessory tube of FIGS. 30-32;

FIG. 33B is a back end view of the sealing element in the cannula of the accessory tube of FIGS. 30-32;

FIG. 33C is cross-sectional view along lines 33C-33C of FIG. 33B;

FIG. 46A is an expanded view of the distal end of the suturing instrument of FIG. 46;

FIG. 48A is an expanded view of the distal end of the suturing instrument of FIG. 48;

FIGS. 60, 61, 62, and 63 are exploded views showing stages of assembly of the components of the shaft of the suturing instrument of FIG. 46;

FIG. 61A is a cross-sectional view along lines 61A-61A of FIG. 61 showing attachment of distal coupler to the cable prior to attachment to the flexible body of the suturing instrument;

FIG. 63A is an expanded exploded view of the distal end of the suturing instrument of FIG. 46;

FIG. 65A is an expanded view of the regions of undulating diameters along the needle of FIG. 65;

FIG. 65B is an expanded view of the tip of the needle of FIG. 65;

FIG. 72 is cross-sectional view along lines 72-72 of FIG. 68;

FIG. 73 is cross-sectional view along lines 73-73 of FIG. 68;

FIG. 74 is cross-sectional view along lines 74-74 of FIG. 68;

FIG. 75 is cross-sectional view along lines 75-75 of FIG. 68;

FIG. 76 is cross-sectional view along lines 76-76 of FIG. 68;

FIG. 77 is cross-sectional view along lines 77-77 of FIG. 68;

FIG. 78 is cross-sectional view along lines 78-78 of FIG. 68;

FIG. 79 is an exploded view of the distal coupler of the suture securing instrument of FIG. 66 prior to attachment to the distal end of the flexible tube;

FIG. 80 is an exploded perspective view showing the coupling of proximal end of the drive wire to the actuator member of the suture securing instrument of FIG. 66;

FIG. 81 is a exploded perspective view of the assembly of the shaft of the suture securing instrument of FIG. 66 prior to the coupling of the distal end of the drive wire, which extending through assembled shaft, to the wedge tip section of the instrument's distal end;

FIG. 82 is an exploded perspective view of the distal end of the suture securing instrument of FIG. 66 prior to coupling the distal coupler to the flexible tube of FIG. 81; and FIG. 82A is a cross-sectional view along lines 82A-82A of FIG. 66A showing the assembled distal end of the suture securing instrument of FIG. 66.

DETAILED DESCRIPTION OF THE INVENTION

Figure 1:
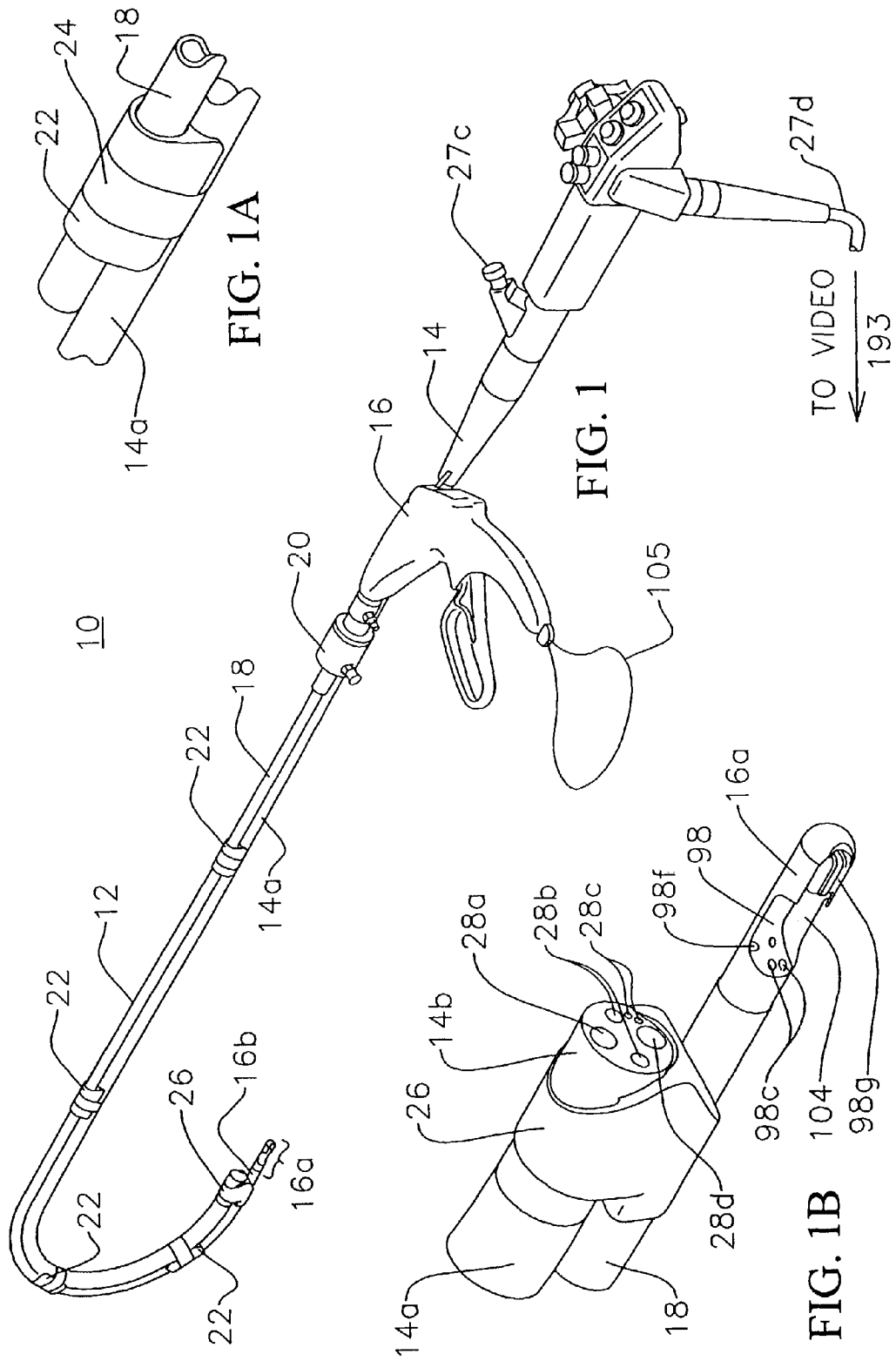
FIG. 1 is a perspective view of the system in accordance with the present invention for application of a suture in tissue.
Figure 2:
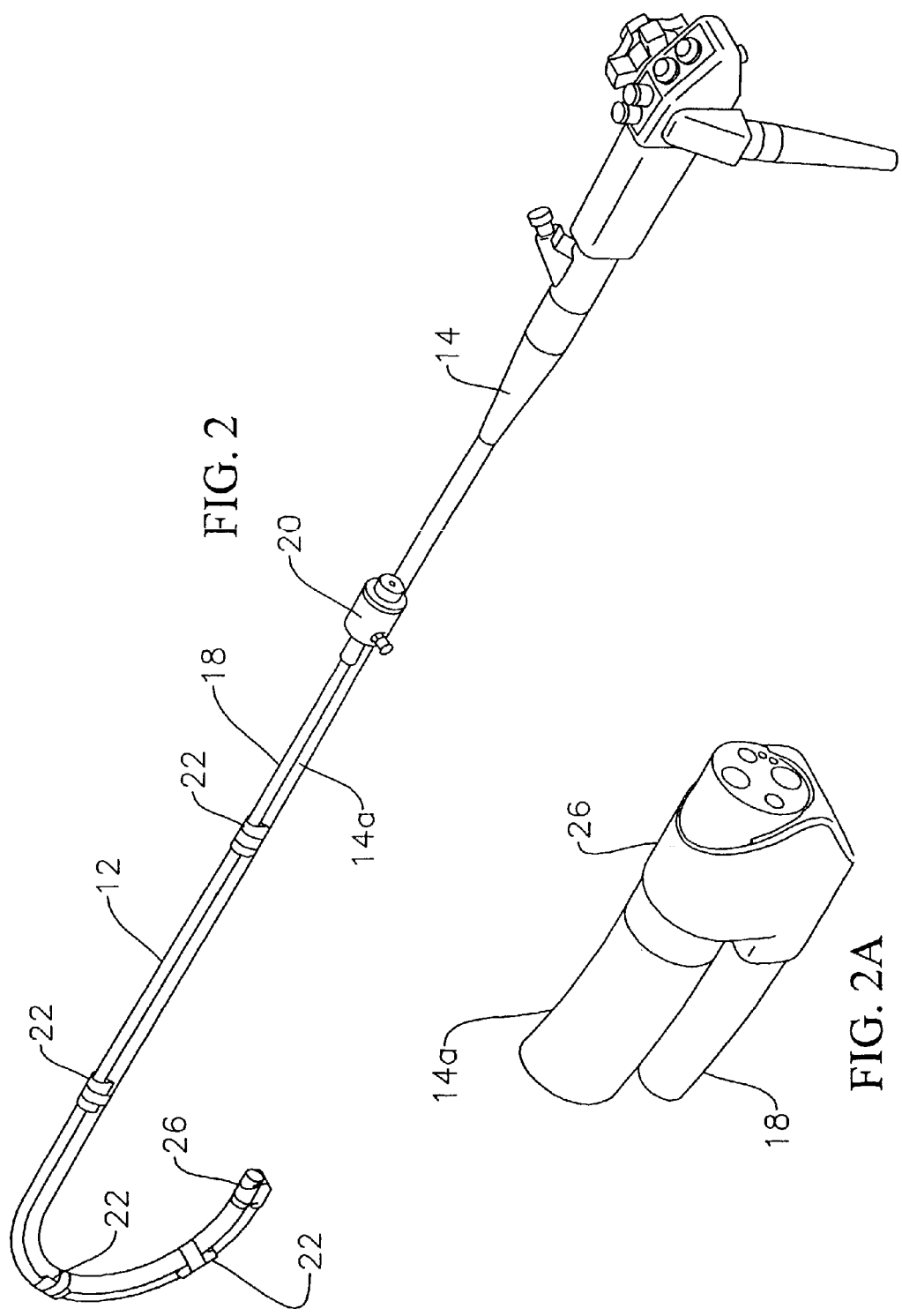
FIG. 2 is a perspective view of the system of FIG. 1 with the suture instrument of the system removed.
Figure 6:
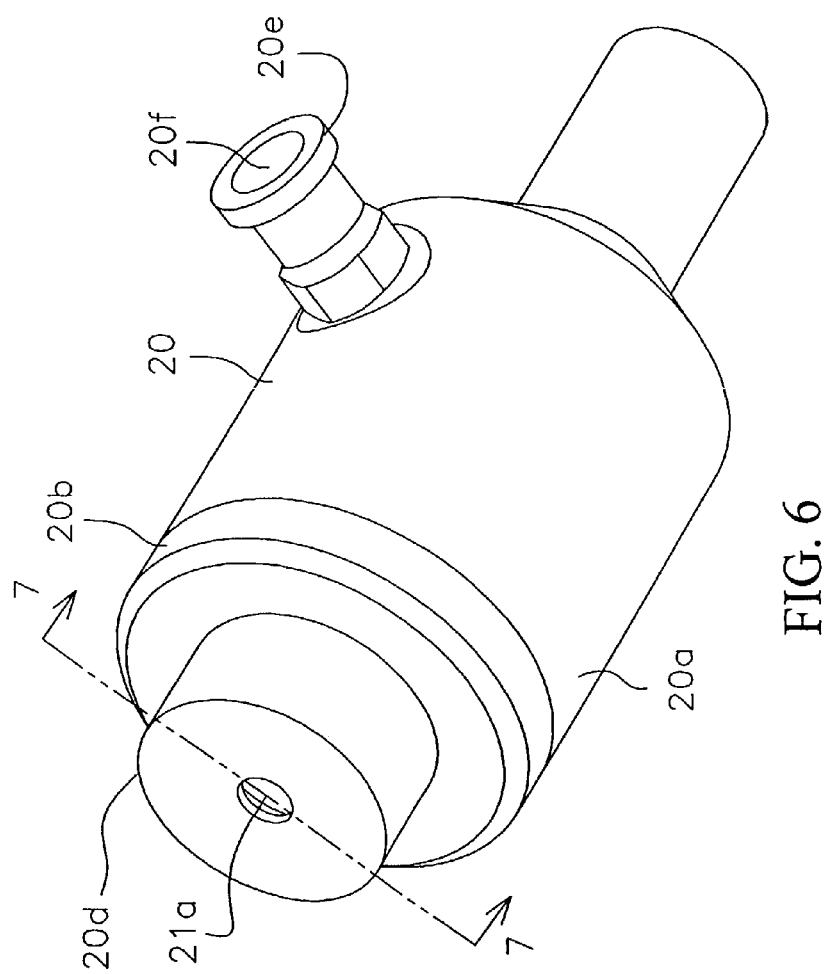
FIG. 6 is a perspective view of the cannula of FIG. 3.

Referring to FIG. 1, a system 10 for suturing is shown including an accessory tube 12 and an endoscope 14, referred to herein after as a gastroscope, or other type of flexible endoscope having a shaft 14a coupled to the accessory tube, and a suturing instrument 16. The suturing instrument 16 may be inserted in the accessory tube 12 as shown in FIG. 1, and is removable from the accessory tube 12 as shown in FIG. 2. The accessory tube 12 has access tubing 18 which is sufficiently flexible to be movable with flexing of the flexible shaft 14a of the gastroscope. Tubing 18 is braid reinforced with a braid of stainless steel, nylon, or Kevlar, to maintain the integrity of the tubing's circular cross-sectional shape and avoid kinking as the shaft 14a of the gastroscope bends when placed through-the mouth into the gastrointestinal tract of a patient. The braiding may be located between two layers of tubing 18, which are integrated with the braiding during their extrusion forming tubing 18. For example, the outer diameter of tubing 18 may be 0.263 inches, while the internal diameter of tubing 18 may be 0.231 inches, and is such that a tissue engaging end 16a coupled to shaft 16b of suturing instrument 16 can pass through the tubing. Tubing 18 may be composed of pebax, polyurethane, or other flexible plastics of medical grade. The accessory tube 12 further has a cannula 20 attached to tubing 18 through which instruments, such as suturing instrument 16, may pass. Cannula 20 is described in more detail later in connection with FIGS. 6 and 7. Accessory tube 12 is shown as a separate component in FIG. 2.

Figure 3:
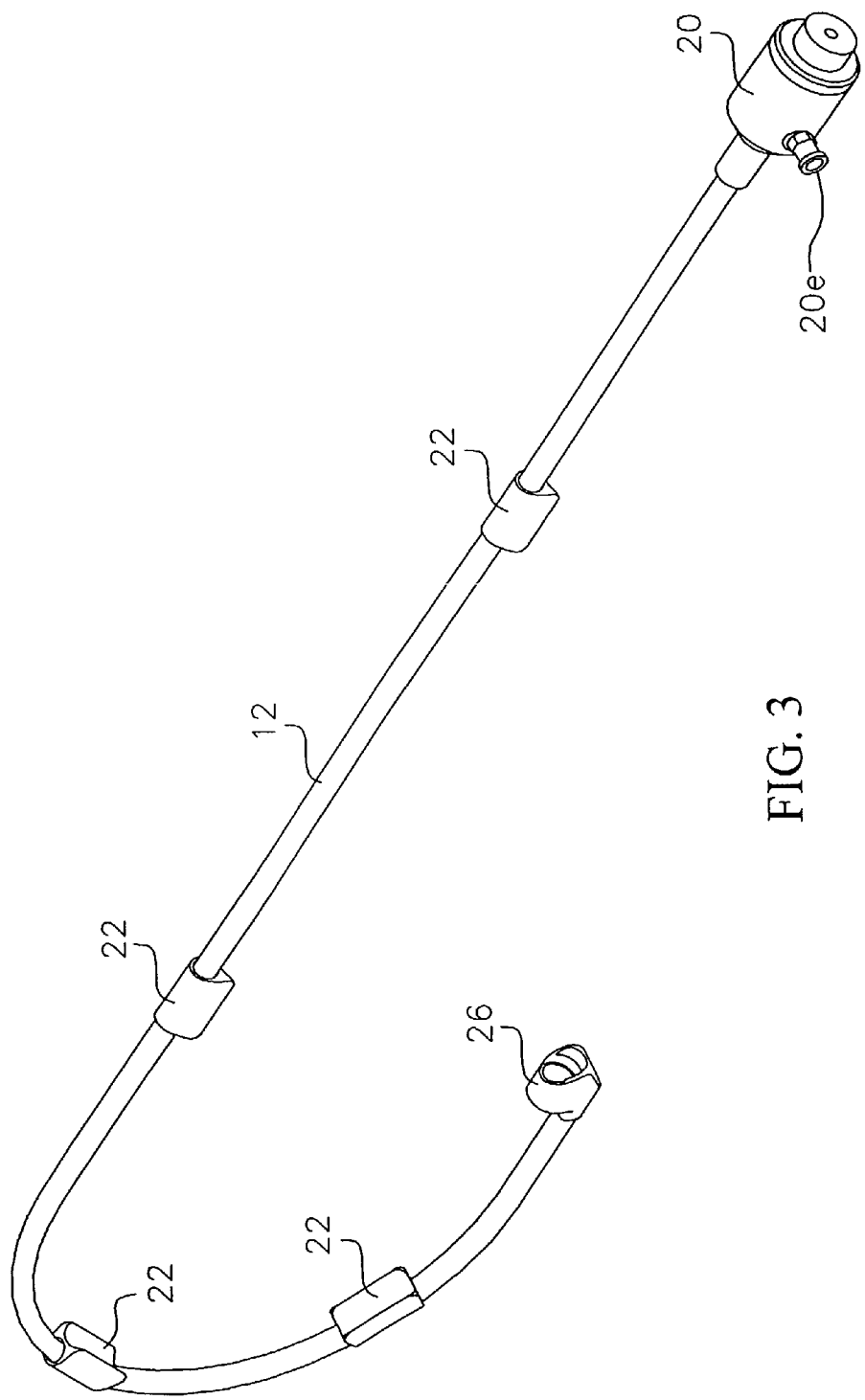
FIG. 3 is a perspective view of the accessory tube, cannula, attachment tip and tube guides of FIGS. 1 and 2.
Figure 4:
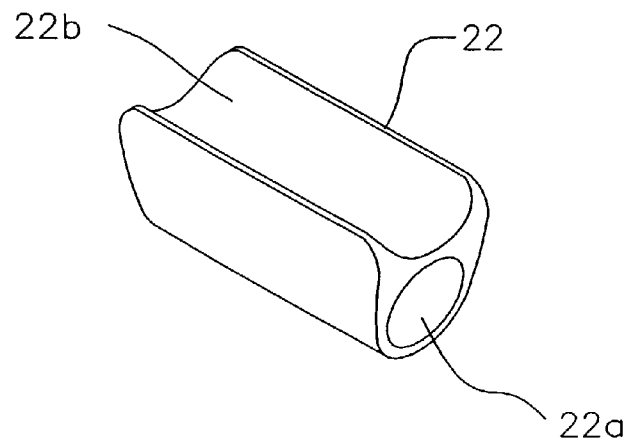
FIG. 4 is a perspective view of the tube guide of FIG. 3.
Figure 4A:
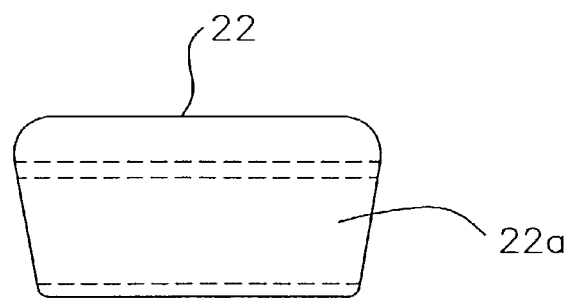
FIG. 4A is a side view of the tube guide of FIG. 4.

Multiple tube guides 22 couple tubing 18 to shaft 14a of gastroscope 14. Each tube guide 22 has an opening 22a extending through the tube guide and a curved surface 22b along its length which abuts the outer curved surface of shaft 14a, as shown in FIGS. 1A. FIGS. 4 and 4A show the tube guide 22 in more detail. Tube guides 22 may be attached to shaft 14a by a band of tape 24 having an adhesive layer to fix the tube guide to shaft 14a. Other attaching means are also be used, such as glue. The diameter of opening 22a is slightly larger than the outer diameter of tubing 18 such that the tubing 18 is slidable through opening 22a to enable the accessory tube 12 to move in concert with flexing, bending, rotation, or other movements of the gastroscope 14. Tube guides 22 maintain tubing 18 substantial coaxial with shaft 14a of gastroscope 14. Preferably, four tube guides are provided as shown in FIGS. 1, 2, and 3, but other number of tube guides may be used.

Figure 5:
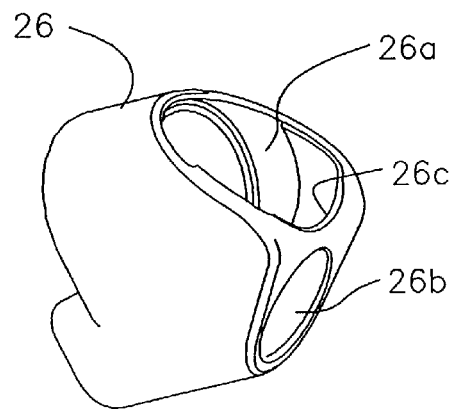
FIGS. 5 and 5A are front and back perspective views, respectively, of the attachment tip of FIG. 3.
Figure 5A:
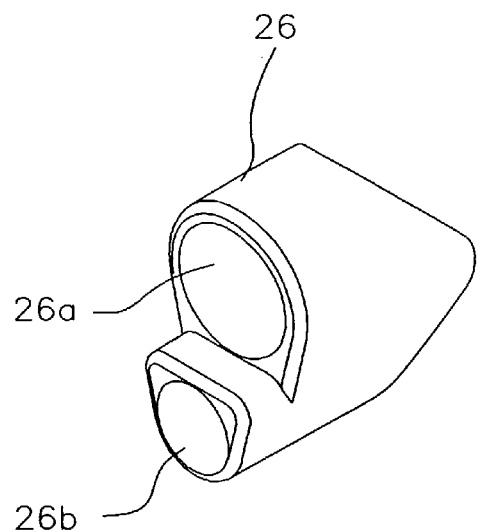

At the distal end of accessory tube 12 is an attachment tip 26 having two openings 26a and 26b to receive one end of tubing 18, and the distal end 14b of gastroscope 14, respectively. Attachment tip 26 is shown in more detail in FIG. 1B, and as a separate component in FIGS. 5 and 5A. Tubing 18 is attached to attachment tip 26, such as by glue or insert molding, while the gastroscope's distal end 14a is held by friction and seats in a shelf or lip 26c (FIG. 5) which forms a stop limiting forward movement of distal end 14a. The attachment tip 26 may be made of urethane or other molded plastic material. The length of the accessory tube 12 from its cannula 20 to attachment tip 26 may be, for example, 30 inches, but also may be of other lengths.

Gastroscope 14 may be any typical gastroscope, such as that manufactured by Olympus, Inc., Pendax, Inc., VisionSciences, or Welch Allyn. For purposes of illustration, gastroscope 14 has at its upper end 14c a handle 27a, two dials 27b to steer the gastroscope, and various buttons/knobs to control typical gastroscope operation. The distal end 14b of the gastroscope has elements for imaging optics 28a, illumination 28b, water for cleaning imaging optics 28c, and a biopsy or working channel 28d representing tubing in communication with a port 27c at upper end 14c. A video display system 193 (FIG. 29B) is coupled to upper end 14a, via a cable 27d, to allow viewing of tissue from its distal end 14b on a display via optics 28a. Although a gastroscope is referred to herein, any other flexible endoscope may similarly be used. FIGS. 2 and 2A illustrate the accessory tube 12 and gastroscope 14 when no instrument is located in the accessory tube.

Figure 7:
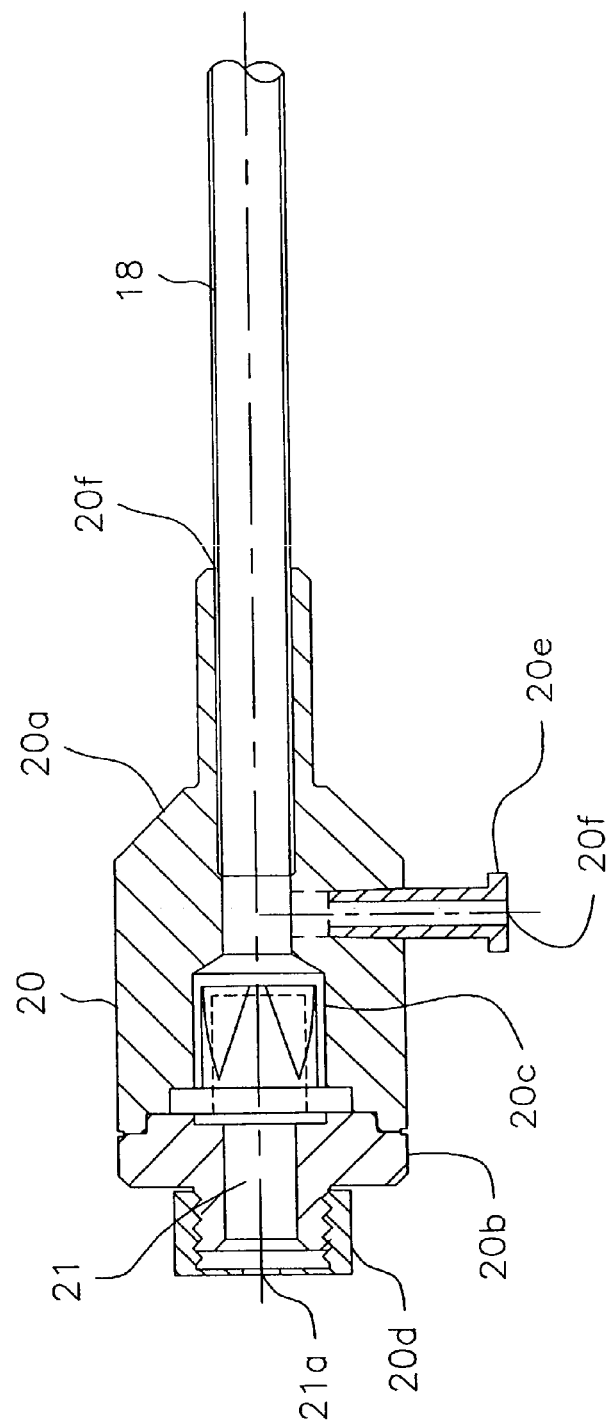
FIG. 7 is cross-sectional view of the cannula along lines 7-7 of FIG. 6.

Cannula 20 may be a typical type of cannula providing a sealable passage to tubing 18. For purposes of illustration, cannula 20 is shown in FIGS. 1-3, and in more detail in FIGS. 6 and 7. Cannula 20 has a housing 20a and a cap 20b which is received in housing 20a. Two seals 20c and 20d are provided in cannula 20 along a passage 21 from an opening 21a through which the shaft of an instrument may pass into tubing 18. Tubing 18 is received in an opening 20f which extends into housing 20a. Seal 20c may be a duck-bill seal as illustrated in FIG. 7. An optional auxiliary port 20e has a bore 20f which opens to passage 21 through which water, air, or vacuum may be provided through tubing 18. Although a cannula with two seals is described, the cannula may alternatively have a single seal. Seal 20d provides sealing about the shaft of an instrument, while seal 20c provides sealing when no instrument is located in the accessory tube 12.

Figure 34:
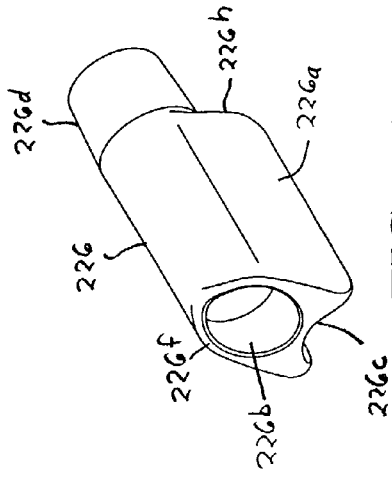
FIG. 34 is a perspective view of one of the tube guides of the accessory tube of FIG. 32.
Figure 34A:
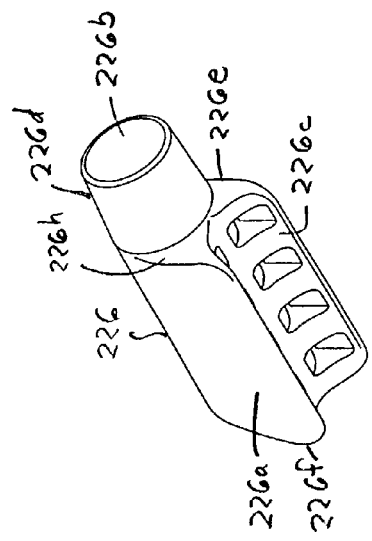
FIG. 34A is a side view of one of the tube guides of the accessory tube of FIG. 32 where dashed lines show the openings in the tube guide.
Figure 35:
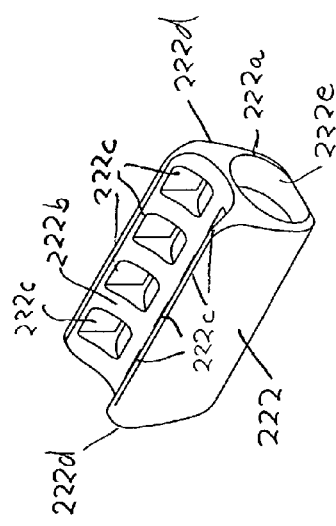
FIGS. 35 and 35A are front and back perspective views, respectively, of the attachment tip of the accessory tube of FIG. 32.
Figure 35A:
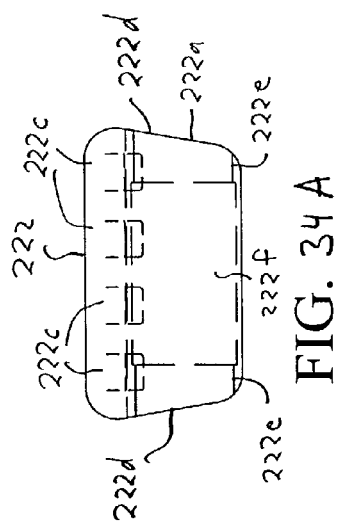

Referring to FIGS. 30, 30A, 30B, 31, 31A, 32, 33, 33A-C, 34, 34A, 35, 35A, and 36-45 another embodiment of the accessory tube in system 10 is shown. In this embodiment, an accessory tube 212 has tubing 218 similar to tubing 18, and a cannula 220 attached to tubing 218 through which instruments may pass through the distal end 212a of the accessory tube. Multiple tube guides 222 similar to tube guides 22 couple tubing 218 to shaft 14a of gastroscope 14. Each tube guide 222 has an opening 222a extending through the tube guide and a curved surface 222b, as best shown in FIGS. 34 and 34A. The curved surface 222b is illustrated with multiple opening or slots 222c. Such slots result when tube guides 222 are molded of plastic material and are optional. Similar to tube guides 22, the ends 222d of each tube guide 222 may have a sloped surface and rounded edges. The opening 222a at each end 222d may be of a narrower diameter at region 222e than the central region 222f of opening 222a located between regions 222e, or the diameter of opening 222a may be the same through the tube guide. Similar to tube guide 22, curved surface 222b abuts the outer curved surface of gastroscope shaft 14a. Tube guides 222 may be attached to shaft 14a by a band of tape 224 having an adhesive layer to fix the tube guide to shaft 14a. The diameter of opening 222a enables sliding of tubing 218 through opening 222a with flexing of shaft 14a, similar to that described for accessory tube 12. Six tube guides 222 are shown, but other numbers may be used to maintain tubing 218 substantially coaxial with shaft 14a.

Figure 36:
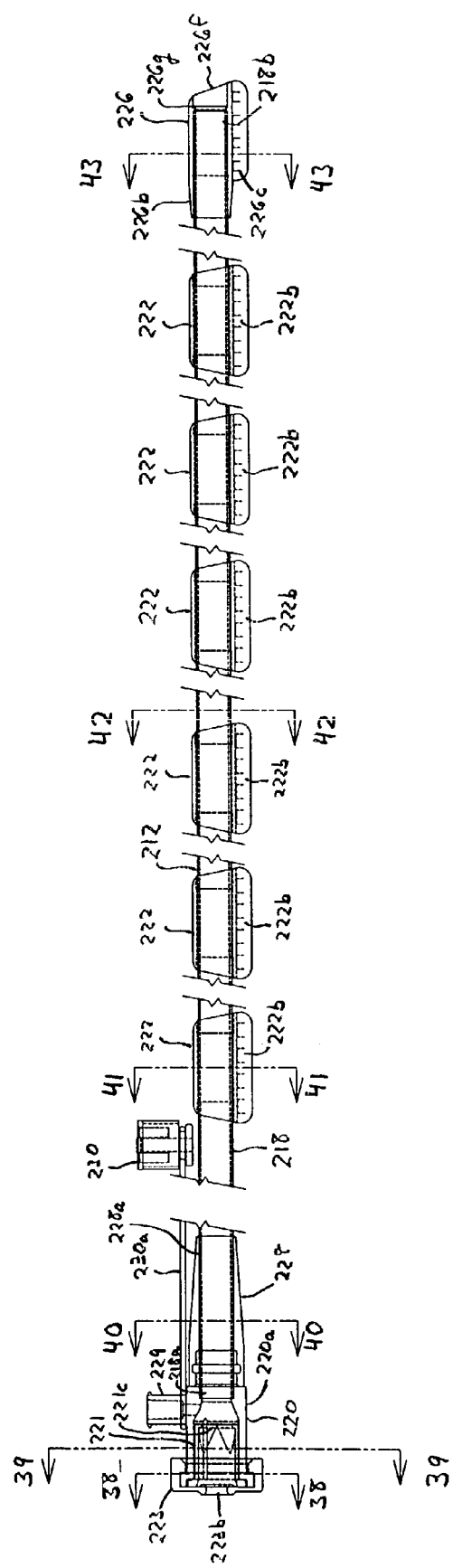
FIG. 36 is a schematic side view of the accessory tube of FIG. 32.
Figure 37:
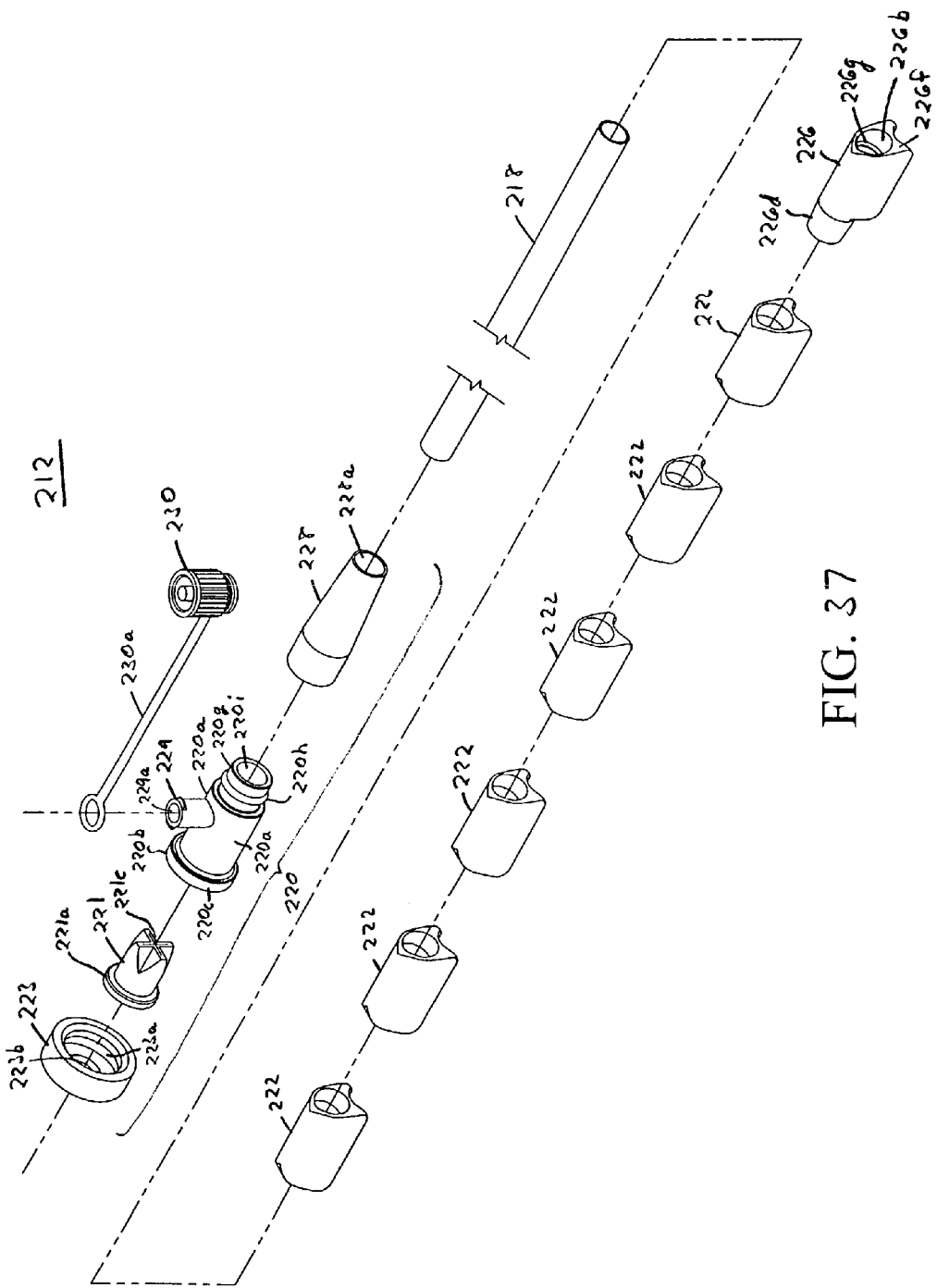
FIG. 37 is an exploded view of the accessory tube of FIG. 32.

The proximal end 218a of tubing 218 is attached to cannula 220, and the distal end 218b of tubing 218 to an attachment tip 226. The attachment tip 226 has a body 226a with an opening 226b there through, and a curved surface 226c similar to surface 222b of tube guide 222, as best shown in FIGS. 35, 35A, 36, and 37. At one end 226e of the tip 226, opening 226b extends through a tapering cylindrical extension 226d that extends from the wall 226h of the tip. In opening 226 near the other end 226f of tip 226 is an interior ring 226g extending from the interior surface of opening 226b (FIGS. 36 and 37). Ring 226g is of a diameter less than the diameter of tubing 218, and sufficient large to enable instruments passed in tubing 218 to extend through opening 226b of tip 226. The surface of end 226f may be sloped similar to end 222d of tube guide 222, and the edges along wall 226h and end 226f rounded. End 218b of tubing 218 is received through opening 226b of extension 226d until interior ring 226g, and attached by glue or insert molding to the tip 226. The distal end 14b of gastroscope 14 end is attached by tape 224 to surface 226c.

Figure 38:
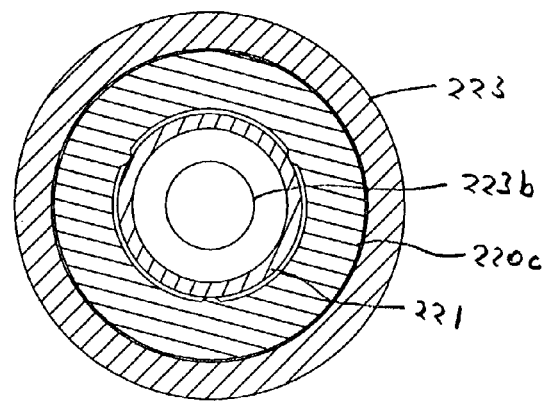
FIG. 38 is cross-sectional view along lines 38-38 of FIG. 36.
Figure 39:
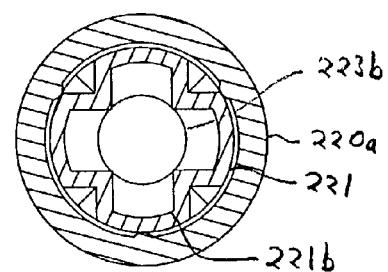
FIG. 39 is cross-sectional view along lines 39-39 of FIG. 36.
Figure 40:
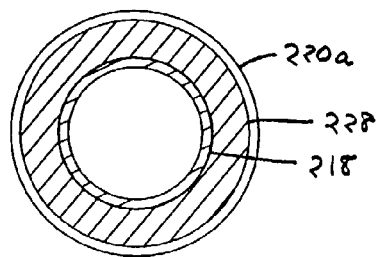
FIG. 40 is cross-sectional view along lines 40-40 of FIG. 36.
Figure 41:
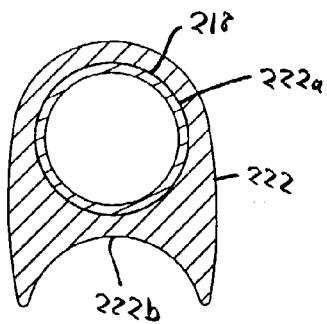
FIG. 41 is cross-sectional view along lines 41-41 of FIG. 36.
Figure 42:
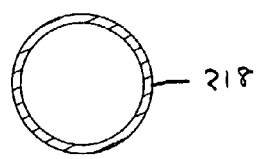
FIG. 42 is cross-sectional view along lines 42-42 of FIG. 36.
Figure 43:
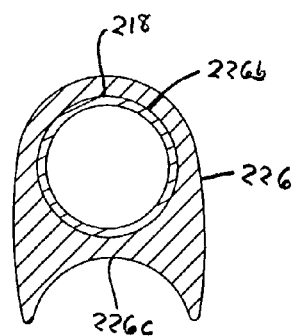
FIG. 43 is cross-sectional view along lines 43-43 of FIG. 36.
Figure 44:
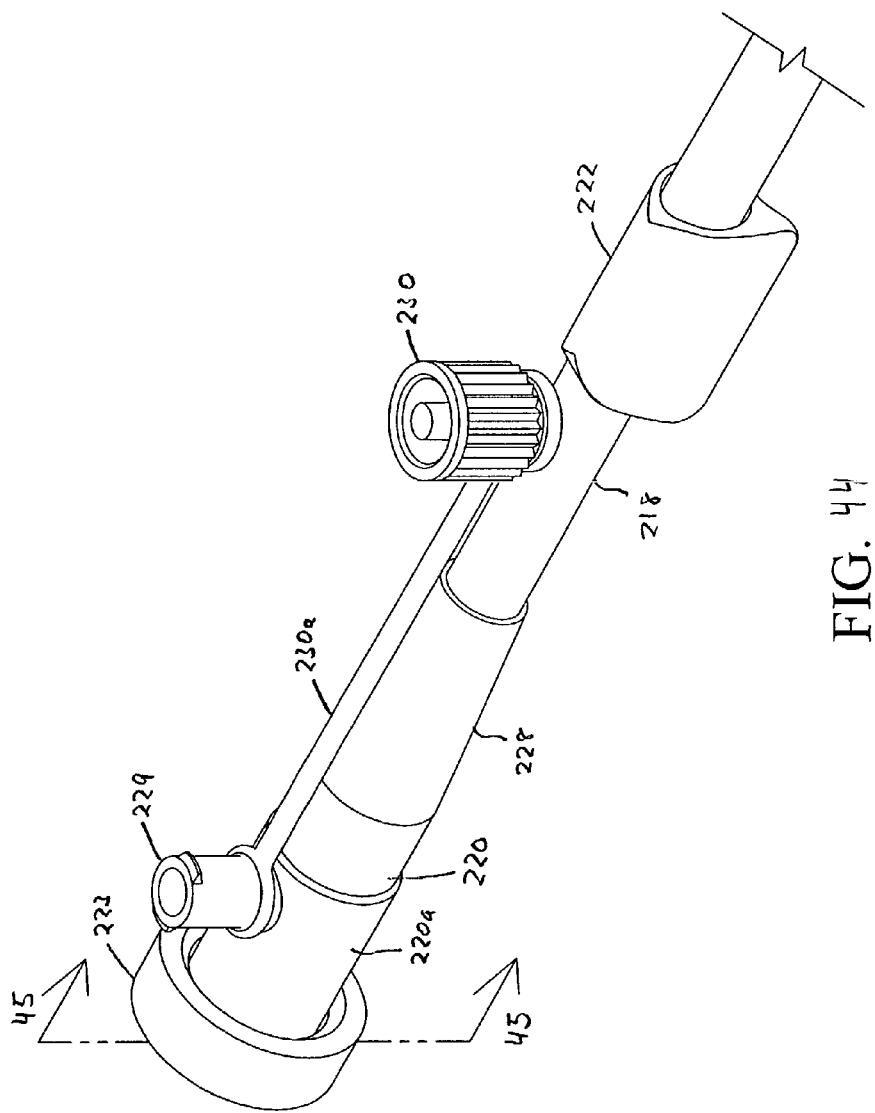
FIG. 44 is a perspective view of the proximal end of the accessory tube of FIG. 32.
Figure 45:
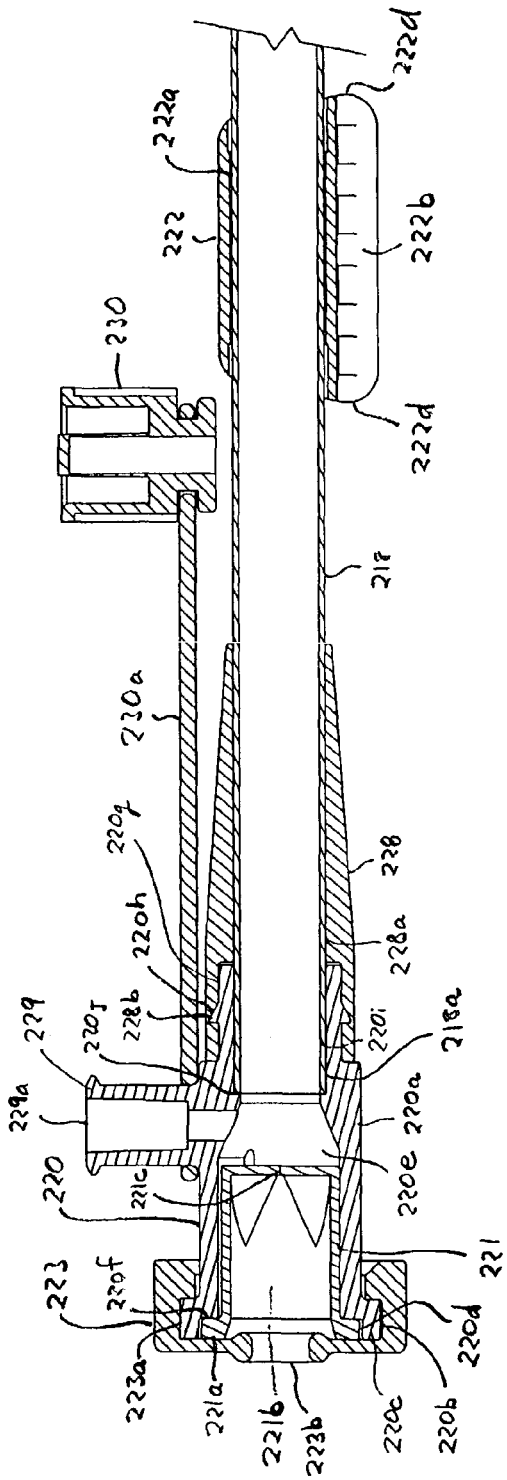
FIG. 45 is cross-sectional view along lines 45-45 of FIG. 44.

As best shown in FIGS. 37, 44, and 45, cannula 220 has a cylindrical housing 220a with a proximal end 220b having a ring 220c about an opening 220d to a cavity 220e. A sealing member 221 is received in cavity 220e through opening 220d. Sealing member 221 has a ring 221a which is disposed upon a recessed ledge 220f formed inside ring 220c. A cap 223 has an annular pocket 223a shaped to receive ring 220c of housing 220a and thereby sealingly locking member 221 therein. The housing 220a has a cap 223 with an opening 223b to a chamber 221b of seal member 221, where the walls of chamber 221b form a duckbill seal 221c opposite opening 222b. A cross-section through the cap 223 is shown in FIG. 38, and through part of seal member in FIG. 37. Seal member 221 is shown in more detail in FIGS. 33 and 33A-C. The seal 221c has a star-shaped configuration and the walls of cavity 221b forming the seal are of a deformable material, such that seal 221c opens in response to passage of an instrument inserted into cannula 220 through sealing member 221 and into tubing 218, and closes when the instrument is withdrawn. In this manner, a sealable passageway is provided by cannula 220 to tubing 218.

The distal end 220g of housing 220a has an opening 220i to the cavity 220e, in which the diameter of the cavity 220e tapers from sealing member 221 to opening 220i (FIG. 45). A cylindrical extension member 228 has a recessed opening 228a into which is received the end 220g of housing 220a. The end 220g has an outer diameter sized to engage recessed opening 228a of the extension member, and a ring or annular raised ridge 220h which is received into annular groove 228b in recessed opening 228a, thereby sealingly locking the extension member to housing 220a. After receiving end 220g of housing 220a, the diameter of opening 228a of extension member 228 is substantially identical to the diameter of opening 220i of housing 220a, such that the proximal end 218a of tubing 218 is received through opening 228a of extension member 228 and opening 220i of housing 220a until annular ledge of stop 220j at the end of opening 220i leading to cavity 220e. The tubing 218 attaches to cannula 220 by frictionally engaging the cannula in openings 220i and 228a, and/or by adhesive. The extension member 228 may have a distally tapering outer diameter.

An optional auxiliary port 229 has a bore 229a which opens to cavity 220e of housing 220a between the sealing member 221 and end 218a of tubing 218 when inserted in cannula 220. A cap 230 is provided to close the port 229 when not needed. The cap 230 is attached by a flexible strap 230a having holes at its ends for coupling to the outside of auxiliary port 229 to cap 230. For example, cap 230 may be a luer type cap.

The tube guides 222 and attachment tip 226 may be made of molded plastic or other biocompatible materials. The components 220a, 223, and 228 of cannula 220 may also be made of molded plastic and are assembled together with sealing member 221, such as by mechanically snap fit engagement to form a passageway with a deformable seal 221c between openings 223b and 228a. The optional port 229 may also be molded with housing 221a. Cross-sectional views through the accessory tube 220 are shown in FIGS. 38-43. Either cannula 220 or 22 may be used with accessory tube 220.

The assembly of the gastroscope 14 and accessory tube 12 or 212 when in the gastrointestinal or gastroesophageal tract of a patient provides the feature of enabling instruments, such as the suturing instrument, and the later to be described suture securing instrument, to be insertable and retractable about the distal end of the gastroscope, without requiring removal of the gastroscope. Further, normal functionality of the gastroscope in viewing is provided without any partial obstruction or loss of use of the working channel 28d. An illustration of the system 10 in a patient's body is shown in FIGS. 29A-29F which although illustrated with cannula 22, may similarly use cannula 220.

Figure 8:
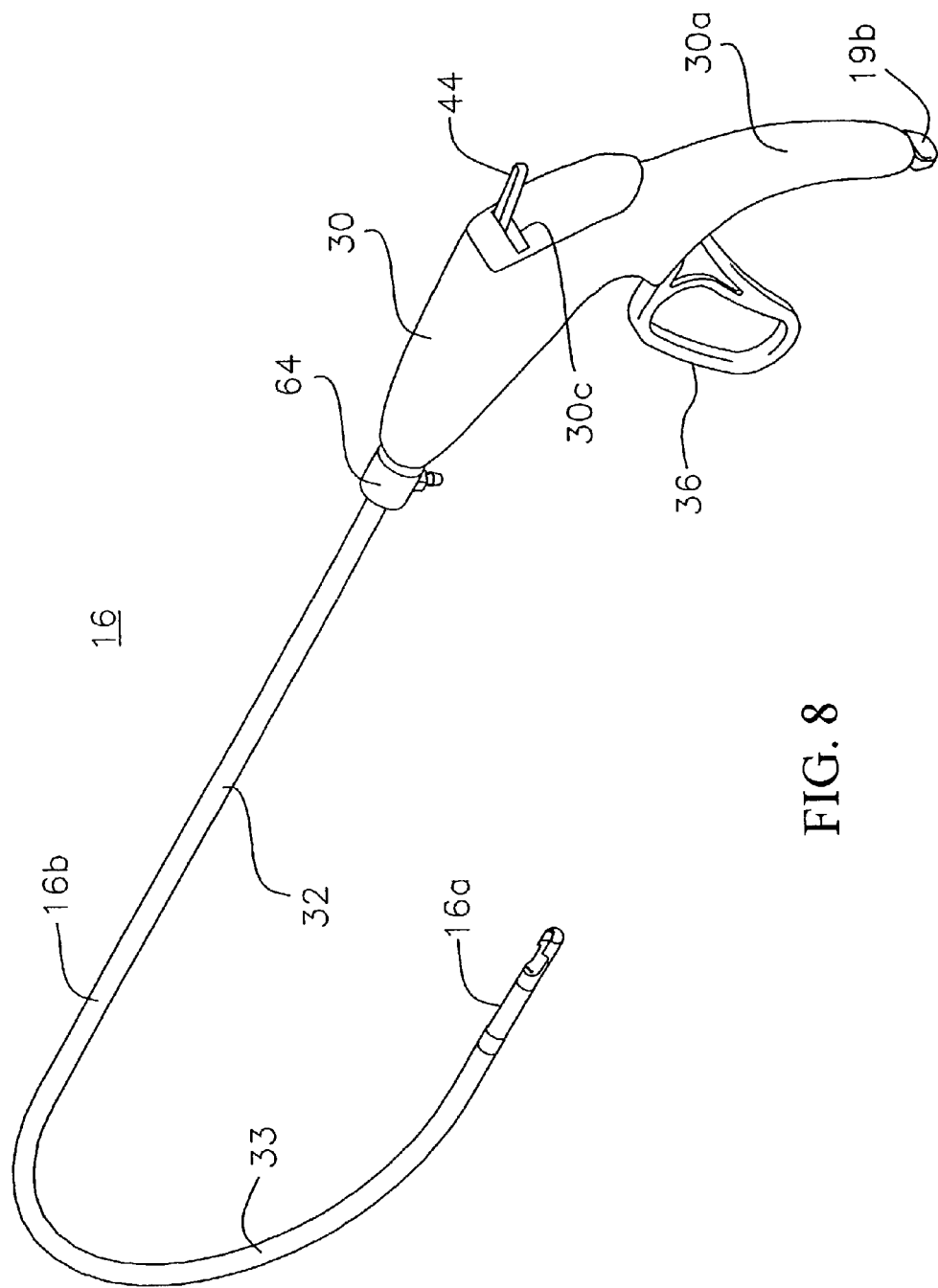
FIG. 8 is a perspective view of the suturing instrument of FIG. 1.
Figure 9:
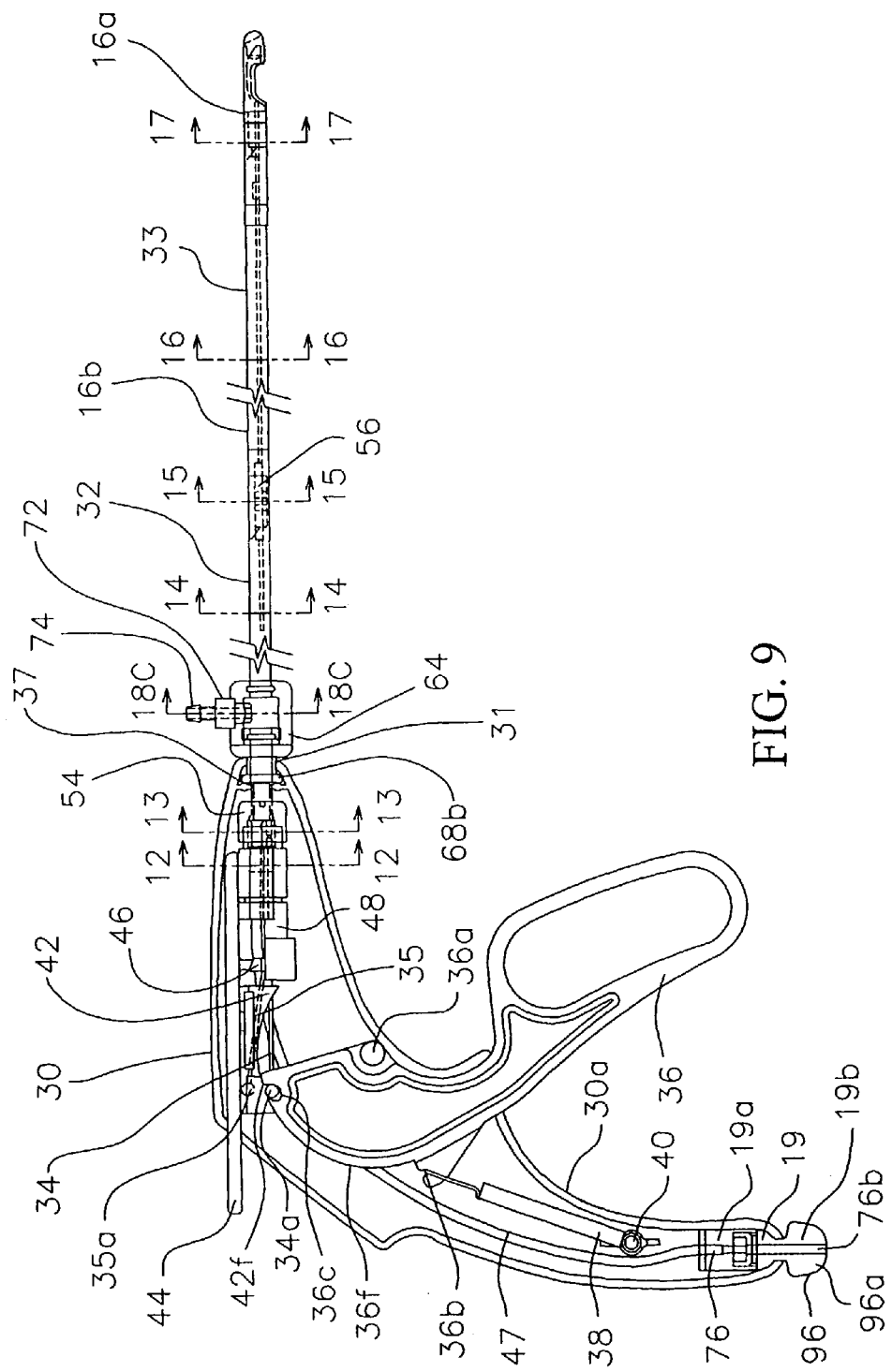
FIG. 9 is a side view of the suturing instrument of FIG. 1 in which the right cover of the housing of the instrument is removed.
Figure 10:
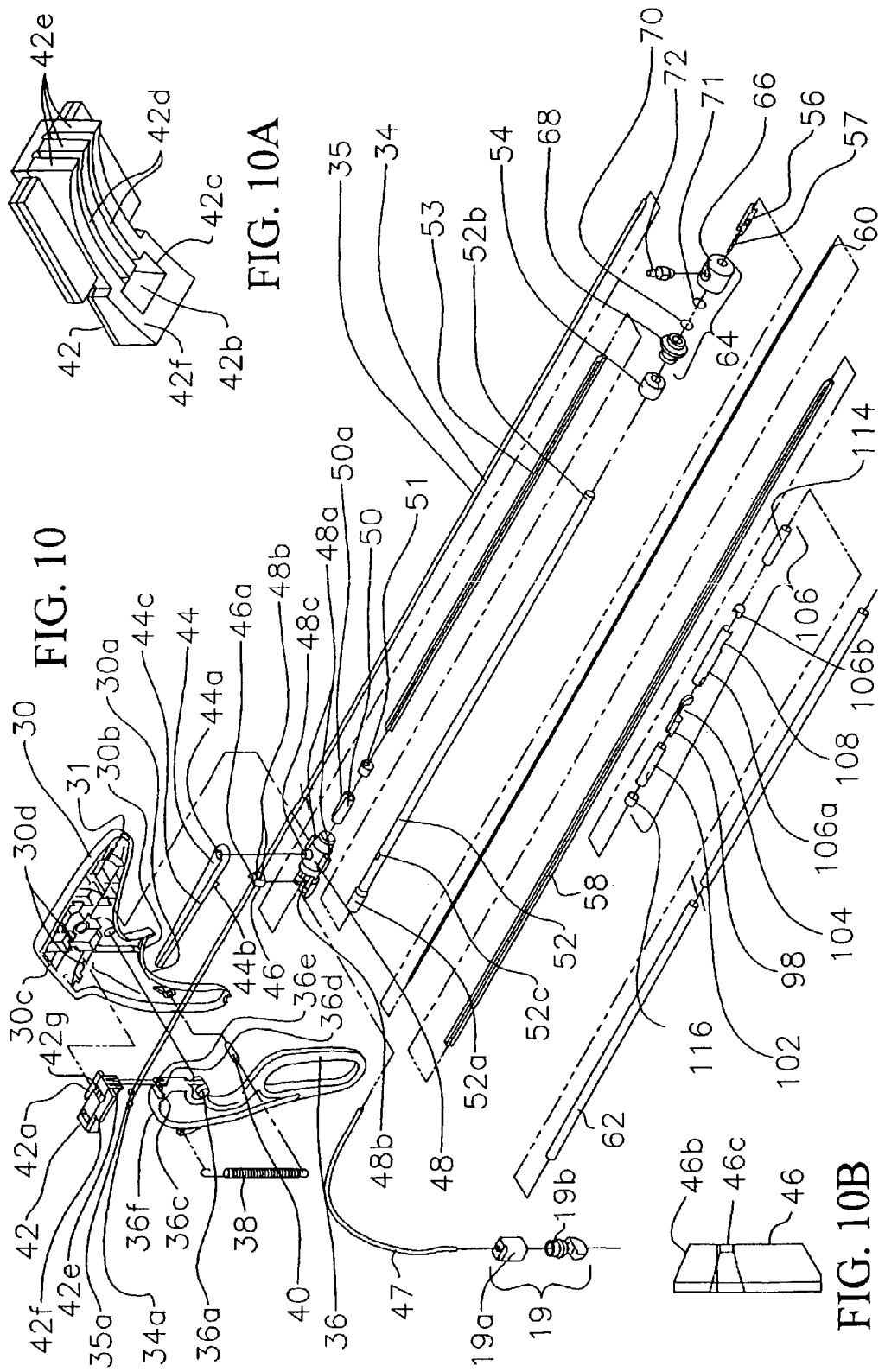
FIG. 10 is an exploded view of the suturing instrument of FIG. 1 in which the right cover of the housing is removed.

Referring to FIGS. 8-10, the suturing instrument 16 of system 10 is shown. Suturing instrument 16 represents the SEW-RIGHT® SR•5™ manufactured by LSI Solutions, Inc. (formally LaserSurge, Inc.) of Rochester, N.Y., which has been modified to have a longer and partially flexible shaft 16b extending from a housing 30, and means for selectably establishing suction to capture tissue at its tissue engaging end 16a. The tissue engaging end 16a and needles thereto may be similar to that shown in U.S. Pat. Nos. 5,431,666, 5,766,183, or European Patent No. EP 0669101, filed Feb. 23, 1995 and granted Oct. 14, 1998, which are herein incorporated by reference. The shaft 16b represents an assembly of components 51-62 described below. Shaft 16b is rigid along a first section 32 when it extends from opening 31 in housing 30 and then is flexible along a second section 33 until coupling to the tissue engaging end 16a. Thus, as shown in FIG. 8 for example, shaft 16b is substantially flexible at least along section 33 of the shaft.

The housing 30 has a body shaped like a pistol having a handle portion 30a, and may be made of a two-piece construction of molded plastic. A pair of needles 34 and 35 extends from housing 30 through the shaft 16b into the tissue engaging end 16a. Each needle 34 and 35 has a non-tissue engaging end in the housing having a spherical member 34a and 35a, such as a ball or bearing, respectively, attached thereto. Both needles 34 and 35 and spherical members 34a and 35a may be a made of metal, such as surgical stainless steel. The spherical member 34a and 35a may have a bore into which the non-tissue engaging ends of the needles 34 and 35, respectively, extend and joined thereto, such as by welding or brazing. The suturing instrument 16 includes an actuator member 36 representing a lever having two pins 36a extending into holes in the sides of housing 30 upon which the actuator member is pivotally mounted in the housing. Actuator member 36 has a portion which extends through an opening 30b (FIG. 10) in housing 30 to enable pivotal movement about pin 36a. An extension spring 38 is provided which hooks at one end in a notch 36b of actuator member 36 and is wound at the other end around a pin 40 located in holes in the sides of housing 30, such that the actuator member 36 is spring biased to retain actuator member 36 normally in a forward position, as shown for example in FIG. 9. The body of housing 30 has a front portion 31 (FIG. 10) providing a stop that limits the pivotal movement of the actuator member 36. A notch 36c is provided in the actuator member 36 which is shaped to received one of the non-engaging ends of needles 34 or 35, i.e., spherical members 34a or 35a, to be driven forward by an operator pulling actuator member 36 to pivot actuator member 36 towards handle portion 30a. Two grooves 36d (FIG. 10) are provided by three fingers 36e into which the needle 34 or 35 near the spherical members 34a or 35a, respectively, may lie.

A retainer member 42 is fixed in housing 30 by two flanges 42a above actuator member 36. As best shown in FIG. 10A, the retainer member 42 has a chamber 42b having a lower opening 42c to chamber 42b and two grooves 42d formed by fingers 42e which allow the spherical members 34a or 35a of needles 34 or 35, respectively, to be received in chamber 42b to restrict movement of the needle when held therein. The lower surface 42f of retainer member 42 is curved and faces correspondingly curved upper surface 36f of actuator member 36, such that the actuator member 36 is slidable along lower surface 42f responsive to the operator pulling the actuator member.

To select which of the needles 34 and 35 is to be driven by actuator member 36, the instrument 16 has a needle selection mechanism having a selector lever (or arm) 44 which is rotationally coupled with a cam member 46. The cam member 46 and selector lever 44 is supported by an adapter 48 in housing 30. Adapter 48 is mounted in housing 30 by two flanges 48a. The selector lever 44 is pivotally mounted by a pin 48c extending upwards from adapter 48 at a hole 44a through the lever. Selector lever 44 extends through an opening 30c in housing 30 and has a downwardly protruding member 44b which is received in a notch 46a of cam member 46 to rotate cam member 46 in a pocket 48b in the adapter 48 as the selector lever 44 is moved left or right. The cam member 46 may have a tapered surface 46b to facilitate its rotation in pocket 48b and two tapered apertures 46c through which needles 34 and 35 respectively extend, as shown in FIG. 10B. To select needle 34 to be driven, the selector 44 is moved right which rotates the cam member 46 to position needle 34 down and needle 35 up, such that end 34a is located in notch 36c and end 35a is located in chamber 42b of retainer member 42. To select needle 35 to be driven, the selector 44 is moved left which rotates the cam member 46 to position needle 34 up and needle 35 down, such that end 35a is located in notch 36c and end 34a is located in chamber 42b of retainer member 42.

The needle selector 44 may further have another downwardly protruding member 44c which rides in a slot 42g on the upper surface of retainer member 42. The slot 42g is contoured to have angled lower regions on either side of a raised region into which member 44c can be located to releasably lock to retain the position of lever 44 left or right.

The adapter 48 has a bore extending there through in which a needle spreader 50 is located. Needle spreader 50 has two channels 50b and 50c into which needles 34 and 35 are respectively located to increase the distance between the needles 34 and 35 as they extend toward cam member 46, such that the needles are properly aligned to apertures 46b in the cam member.

Figure 11:
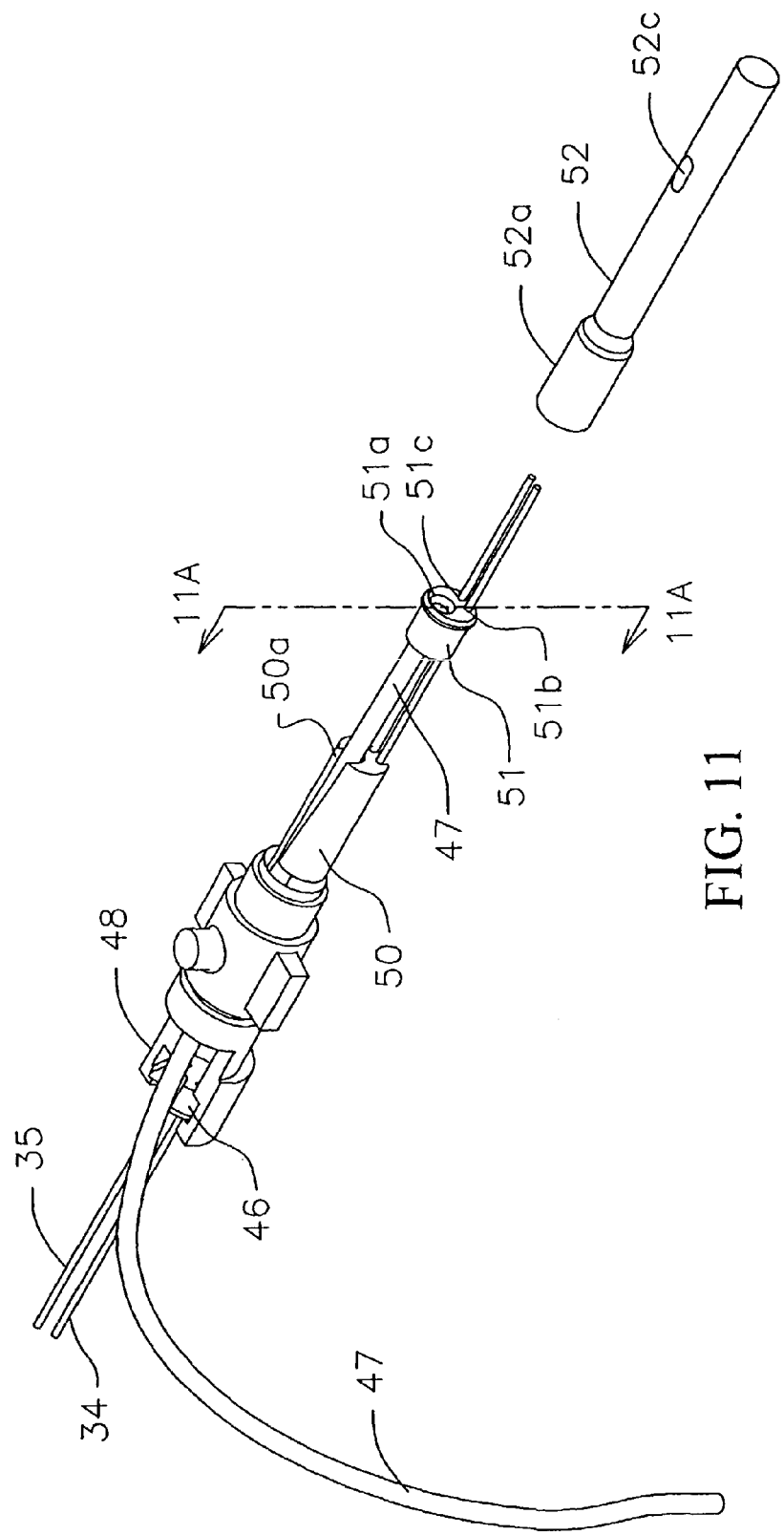
FIG. 11 is a partially exploded perspective view of the adapter, needle spreader, and gasket member of the suturing instrument of FIGS. 9 and 10.
Figure 12:
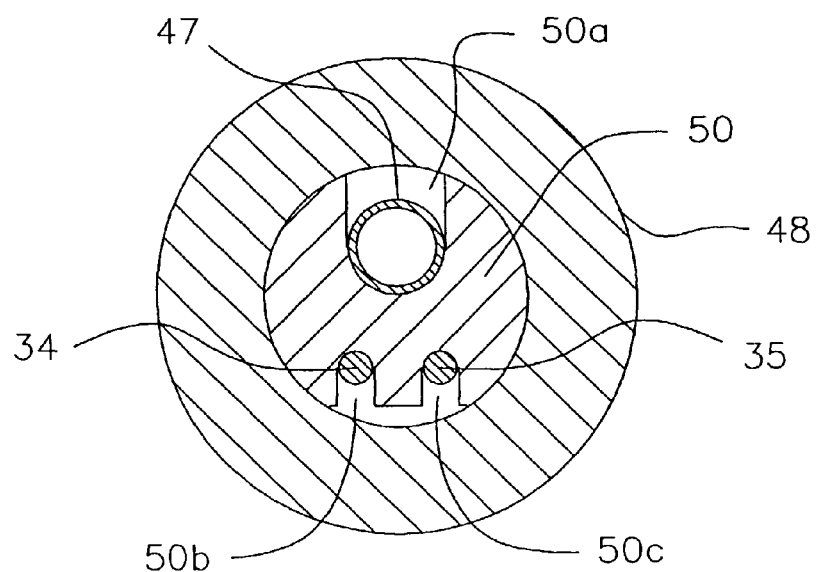
FIG. 12 is a cross-sectional view along lines 12-12 of the suturing instrument of FIG. 9.
Figure 13:
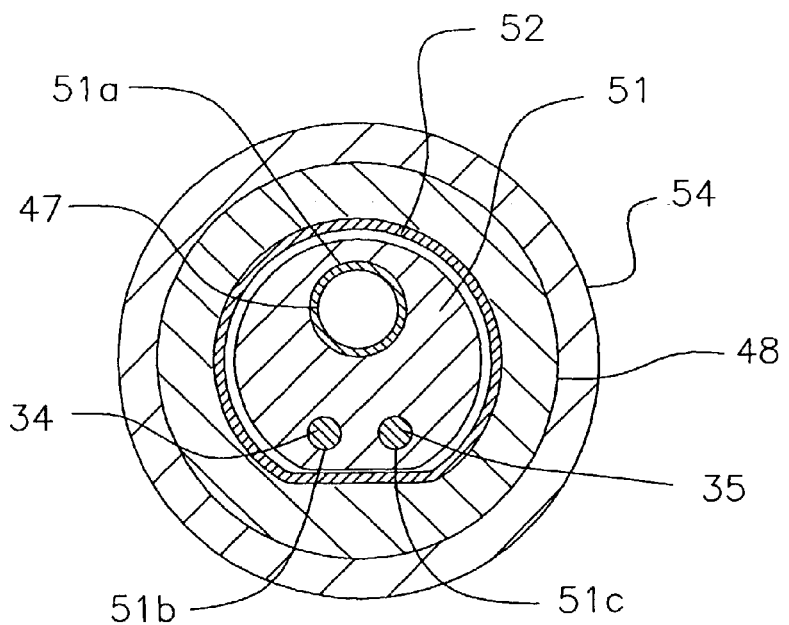
FIG. 13 is a cross-sectional view along lines 13-13 of the suturing instrument of FIG. 9.

A suture routing tube 47 is provided for suture thread in housing 30. Suture routing tube 47 has one end received in a valve assembly 19, described later below, at the bottom of handle 30a of housing 30 and then extends through notches 30d (FIG. 10) along the interior of the left side of housing 30, and a groove 50a along needle spreader 50 (FIGS. 10 and 11). A cross-section through needle spreader 50 and adapter 48 is shown in FIG. 12. The other end of the suture routing tube 47 is then mounted in a hole 51a through gasket member 51. Gasket member 51 further has two holes 51b and 51c through which needles 34 and 35, respectively extend. A cross-section of shaft 16b through gasket member 51 is shown in FIG. 13. The gasket member 51 may be made of medical grade rubber, such as Santoprene.

Figure 11B:
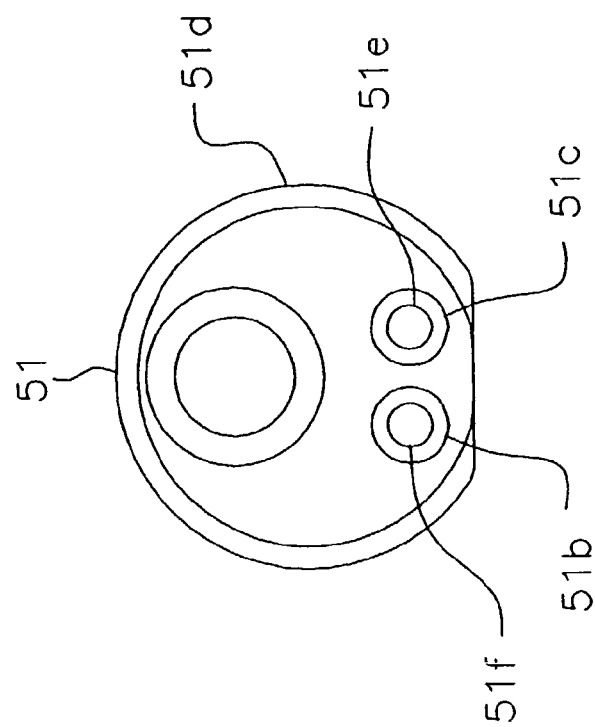
FIG. 11B is an end view of the gasket member of FIG. 11 without suture tube or needles.
Figure 11A:
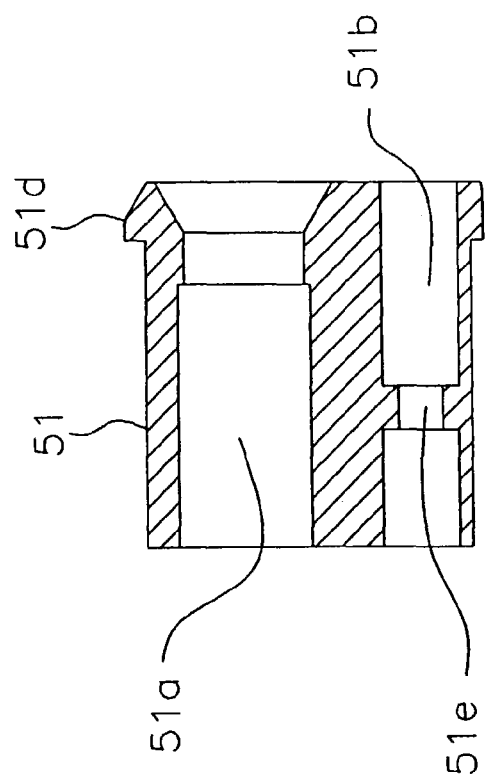
FIG. 11A is a cross-sectional view through lines 11A-11A of FIG. 11 showing the gasket member of the suturing instrument of FIG. 11 without the suture tube or needles.
Figure 14:
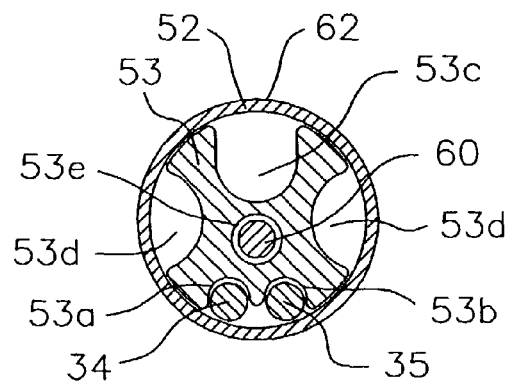
FIG. 14 is a cross-sectional view along lines 14-14 of the suturing instrument of FIG. 9.

A longitudinal guide member 53 is provided multiple tracks along its length, including two needle tracks 53a and 53b for needles 34 and 3-5, respectively, and a suture track 53c for suture thread extending from opening 51a of gasket member 51. A cross-sectional view of shaft 16b through guide member 53 is shown in FIG. 14. The guide member 53 may be made of extruded flexible material, such as Tecoflex®. A rigid tube 52 is provided which is D-shaped at one end 52a is registered into a corresponding shaped opening in adapter 48, and a threaded nut 54 having an opening which extends over mounting tube 52 and screws onto the end of the adapter 48 to secure tube 52 to housing 30. With the gasket member 51 loaded first into rigid tube 53, guide member 53 extends from the gasket member 51 through the rigid tube. In this manner, tracks 53a, 53b, and 53c each form a channel with the interior surface of rigid tube 52. Rigid tube 52 may be made of stainless steel, or other rigid material, and has for example, rigid tube 53 has an outside diameter of 0.205 inches. FIG. 11 shows the gasket member 51 prior to being positioned in abutment to needle spreader 50 and in end 52a of rigid tube 52. For inside rigid tube 52, gasket member 51 has a ring 51d which frictionally engages the interior surface of tube 52, hole 51a of the gasket member is of a diameter such that the suture tube 47 tightly fits therein and provides a seal around suture tube 47. The suture tube 47 may be held in place in hole 51a by friction, but adhesive may also be used. FIGS. 11A and 11B show gasket member 51 in more detail. Holes 51b and 51c are of a larger diameter than the needle, except for a small section of holes 51b and 51c where the diameter reduces to form flaps 51e and 51f, respectively of gasket material which seal around needles 34 and 35, respectively. This enables movement of the needles back and forth while maintaining a seal about each needle. One feature of the gasket member 51 is that it enables sealing the shaft 16b, such that negative pressure, i.e., suction, may be selectively applied down the shaft via a vacuum connection assembly 64, as described later below.

Figure 15:
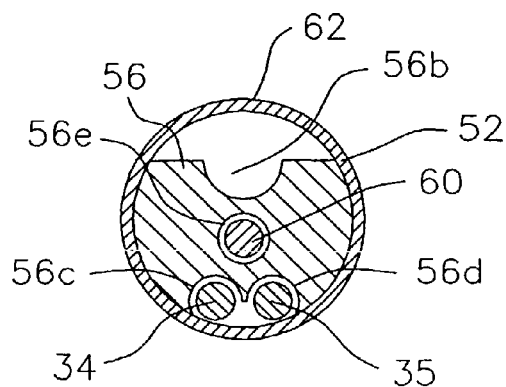
FIG. 15 is a cross-sectional view along lines 15-15 of the suturing instrument of FIG. 9.
Figure 16:
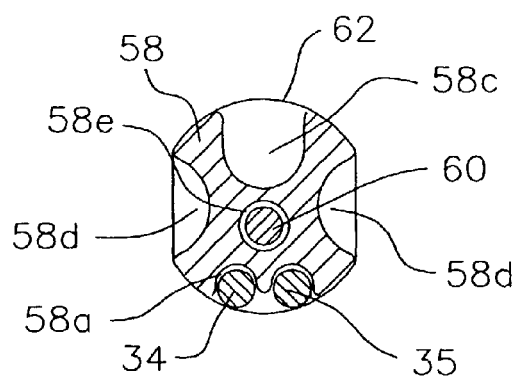
FIG. 16 is a cross-sectional view along lines 16-16 of the suturing instrument of FIG. 9.

At the other end 52b of rigid tube 52, a coupler member 56 is mounted in which two tabs 56a are received in two tracks 53d along two opposing sides of guide member 53. Coupler member 56 joins the non-flexible section 32 of the shaft 16b provided by rigid tube 52 with the flexible section 33 of the shaft 16b (FIG. 8). Coupler member 56 may be composed of stainless steel. A cross-section of shaft 16b through coupler member 56 is shown in FIG. 15. The coupler member has a track 56b for suture, tracks 56c and 56d for needles 34 and 35, respectively, and a central hole 56e. On the side of the coupler member 56 opposite guide member 53 is another longitudinal guide member 58 which extends through the flexible section of shaft 16b to the tissue engaging end 16a. Guide member 58, like guide member 53, is of an extruded flexible material, such as Tecoflex®. Guide member 58 has multiple tracks, including two needle tracks 58a and 58b for needles 34 and 35, respectively, and a suture track 58c for suture thread extending from track 56b of coupler member 56. A cross-sectional view of shaft 16b through guide member 58 is shown in FIG. 16. Two tabs 56f extend from the coupler member 56 into tracks 58d of guide member 58. A wire 60 extends from the tissue engaging end 16a through a central hole 58e of guide member 58 and the central hole 56e of coupler member 56, and then partly into a center hole 53e (FIG. 14) extending into guide member 53. The wire 60 extends partly through central hole 53e to facilitate registration of guide member 53 to coupler member 56 and guide member 58. The wire 60 is located in a central hole which extending into a sew tip 98 at the tissue engaging end 16a and attached thereto, such as by welding or brazing, passed through guide member 58 via hole 58e, and then extended through and in coupler member 56, where it is attached to the coupler member, via a tube coupler 57, such as by welding or brazing. This assembly is described in more detail below in connection with FIG. 17C. With the rigid tube 52, gasket 51, guide members 53 and 58 and central wire 60 in place, a plastic shrink wrap layer or tubing 62 is installed along shaft 16b from the vacuum connection assembly 64 until the tissue engaging end 16a, and shrunk in response to applied heat onto exposed surfaces of shaft 16b. About guide member 58, tracks 58a, 58b, and 58c each form a channel with the interior surface of shrink wrap layer 62.

Figure 17:
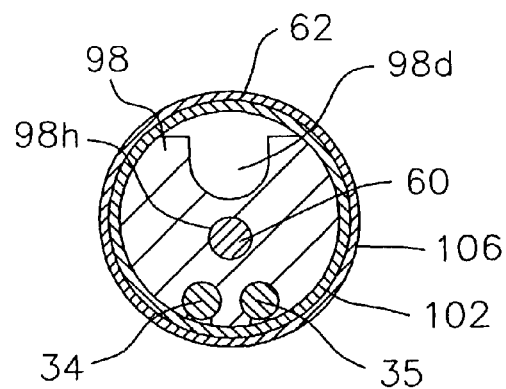
FIG. 17 is a cross-sectional view along lines 17-17 of the suturing instrument of FIG. 9.
Figure 17A:
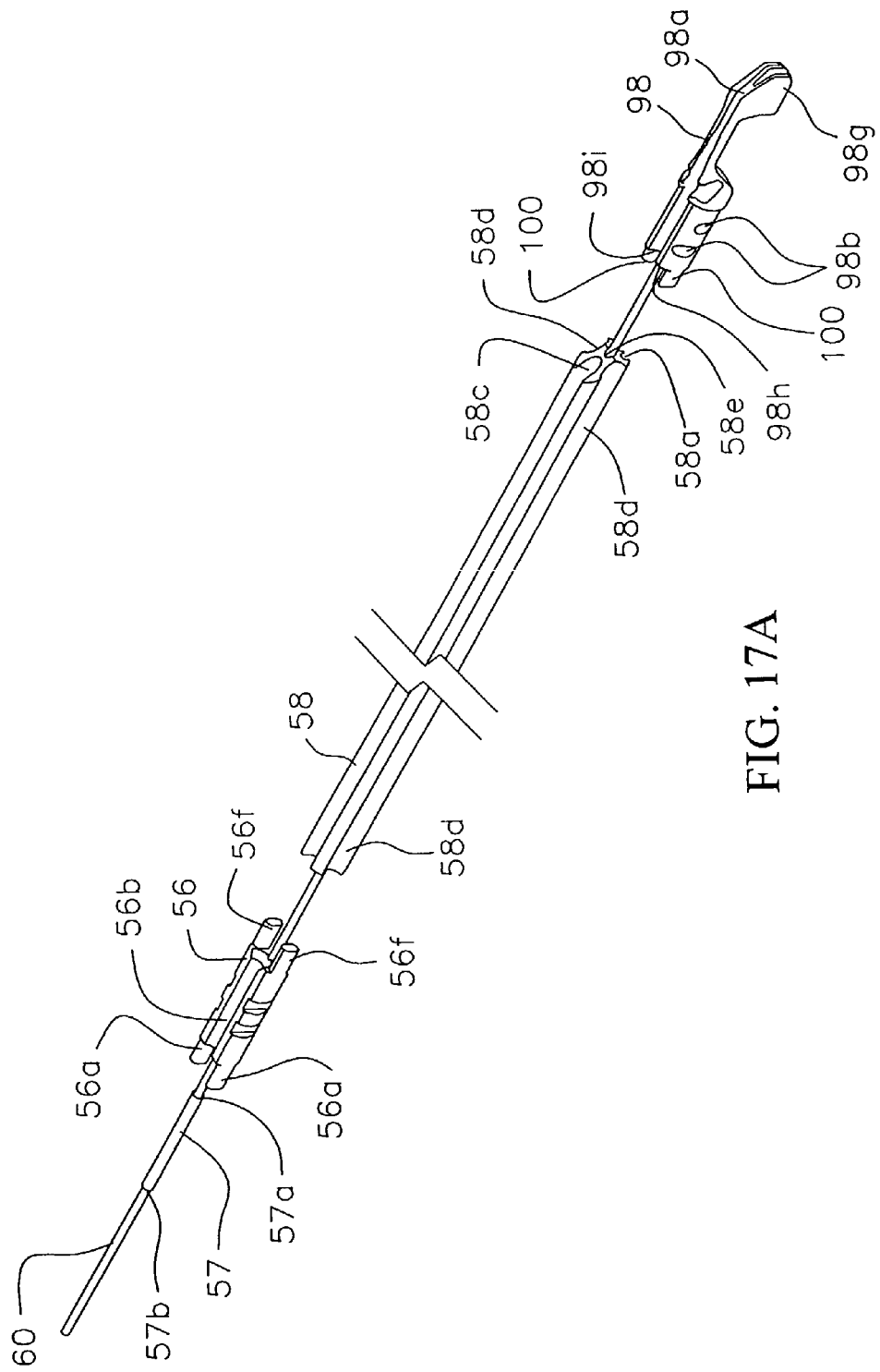
FIG. 17A is an exploded view of the coupler member, sew tip, and the guide member between the coupler member and sew tip, of the suturing instrument of FIGS. 9 and 10.

The connection of coupler member 56, guide member 58 and a sew tip 98 of the tissue engaging end 16a is best illustrated in FIGS. 17A and 17B in which tabs 56f of coupler member 56 are received in tracks 58d at one end of guide member 58, and tabs 100 from sew tip 98 are received in tracks 58d at the other end of guide member 58. Wire 60 extends through coupler member 56, guide member 58 into a hole 98h extends into the rear section 98i of the sew tip 98 (FIG. 21B). The guide member 58 with the shrink wrap enables the flexible section 33 of shaft 16b to bend and flex while maintaining the channels extending there through, while the wire 60 provide longitudinal support to the flexible section as it is attached to non-flexible section 30 at coupler member and the sew tip. Further, needles 34 and 35 are sufficiently flexible to bend without deformation within guide member 58. In order to translate rotational motion from the non-flexible section, tabs 56a and 56f of coupler member are registered into tracks 53d and 58d of guide members 53 and 58, respectively, and then tracks 58d of guide member 58 into tabs 100 of sew tip 98. Thus rotation occurring at the non-flexible section, such as by rotation of housing 30, is translated to tissue engaging end 16a.

FIG. 17C shows the attachment of wire 60, coupler member 56, and flexible section 33 of instrument 16 in more detail, such that possible damage to guide members from the heat of welding or brazing of metal components is avoided. The coupler member 56 has a recessed circular opening 56h to central hole 56e at the end 56g of coupler member 56 into which one end 57a of a wire coupler tube 57 is located. Wire coupler 57 represents a metal tube having an outer diameter sized to be received in recessed opening 56h and an inner diameter sized to receive there through wire 60. Prior to attachment of coupler member 56 to guide member 53, wire coupler 57 is first attached to coupler member 56, such as by welding or brazing, about recessed opening 56h prior to the assembly of the flexible section 33 components, i.e., sew tip 98, and guide member 58, to coupler member 56. Next, wire 60, which has not yet been passed through coupler member 56, is attached, such as by welding or brazing, into hole 98h (FIG. 21B) of sew tip 98. Wire 60 is then slid through central hole 58e of guide member 58 and hole 56e of coupler member 56, and the sew tip 98 at two tabs 100 frictionally engages into two tracks 58d of guide member 58 at one end of guide member 58. At the other end of guide member 58, tabs 56e of coupler member 56 frictionally engages into tracks 58d. With the coupler member 56 integrated with guide member 58, wire 60 is attached at end 57b of wire coupler 57, such as by welding or brazing, which integrates the assembly of coupler member 56 with flexible section 33 of the instrument 16, as shown in FIG. 17B. Thereafter, the coupler member 56 at its tabs 56f frictionally engages into tracks 53d of guide member 53, such that wire 60 partly extends into central hole 53e of guide member 53. The guide member 53 and coupler member 56 of the assembly are received into the rigid tube 52, such that guide member 53 abuts gasket 51, and coupler member is attached to rigid tube by mechanical fastening by forming small dents in the metal of the tube 52 with a press into recessed four pockets 56i (FIG. 17A), i.e., two on each side of the coupler member 56.

Figure 18:
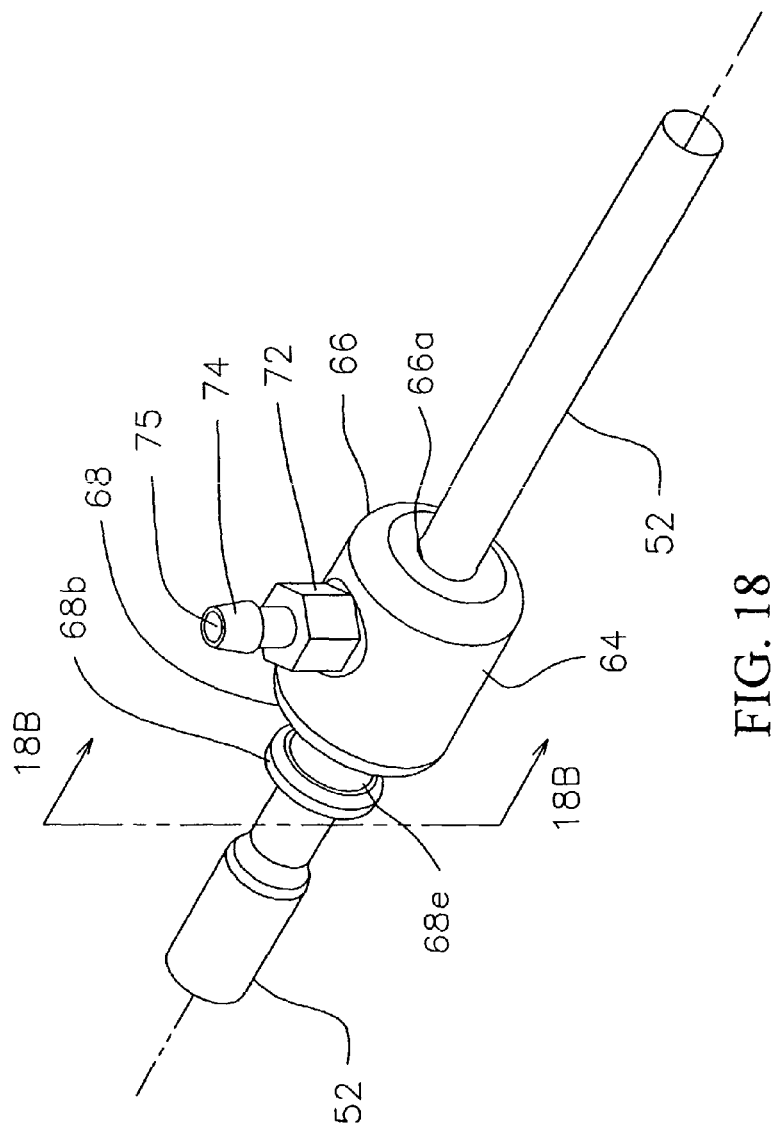
FIG. 18 is a perspective view of the vacuum connection assembly of the suturing instrument of FIGS. 9 and 10 for application of a vacuum or partial vacuum.
Figure 18A:
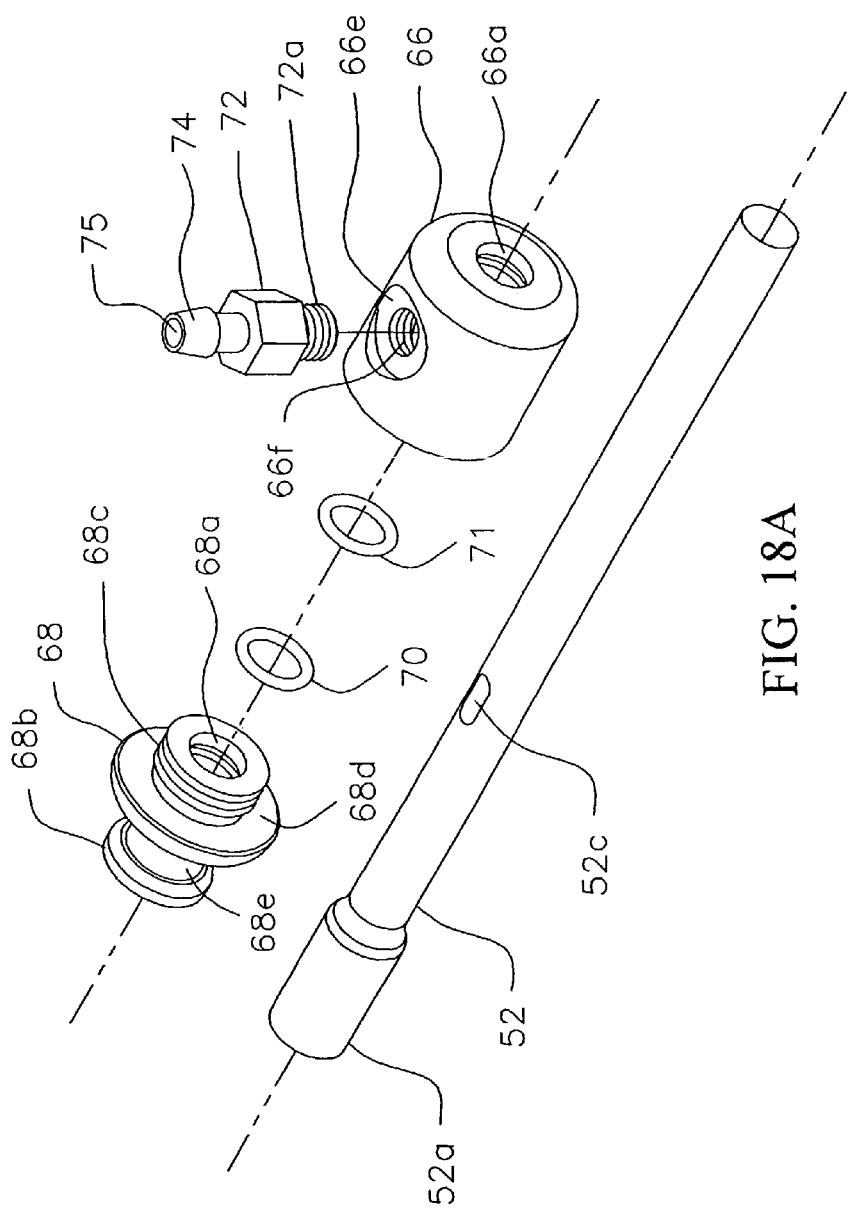
FIG. 18A is an exploded view of the vacuum connection assembly of FIG. 18.

Referring to FIGS. 18 and 18A-C, a vacuum connection assembly 64 for suturing instrument 16 is shown. Vacuum connection assembly 64 includes a front housing member 66 which has a circular opening 66a to an interior chamber 66b, and a rear housing member 68 having a circular opening 68a extending there through. Rear housing member 68 has a first extension toward housing 30 providing a shaft 68e having an annular flange 68b and a second extension toward front housing member 66 providing a threaded shaft 68c. Shaft 68c is screwed in a threaded opening 66c (FIG. 18B) to chamber 66b of front housing member 66, whereby surface 68d of the rear housing member tightly fits (mates) along surface 68d of the front housing member 66. Circular opening 66a is coaxial with circular opening 68a through their respective housing members. A rubber O-ring 71 is provided in an annular groove in opening 66a of the front housing member 66, while another O-ring 70 is provided in an annular groove in opening 68a of rear housing member 68, as illustrated in FIG. 18B. A fitting member 72 is received in front member 66 in a recessed pocket 66e to a threaded opening 66f extending to chamber 66b, such that a port 74 is provided having a bore 75 to chamber 66b. Fitting member 72 is threaded along its surface 72a to enable the fitting member to screw into threaded opening 66f of front housing member 66. Except for O-rings 70 and 71, the components of vacuum connection assembly 64 may be made of stainless steel.

The vacuum connection assembly 64 is placed on rigid tube 52 so that the tube extends through openings 66a and 68a, O-rings 70 and 71, and chamber 66b, and an opening 52c in the rigid tube lies in chamber 66b and faces bore 75 of the fitting member. The diameter of appertures 66a and 68b are slightly larger than the outer diameter of rigid tube 52 about opening 52c. O-rings 70 and 71 engage the outer surface of rigid tube 52 to seal chamber 66b, but for bore 75 and opening 52c to suture track 53c (FIG. 18C). Flange 68b from rear housing member 68 is received in a pocket 37 (FIG. 9) formed when the left and right sides of housing 30 are mated to each other. A vacuum source may be applied via tubing (not shown) to port 74, such that negative air pressure is provided in chamber 66b which may be communicated via an opening 52c of rigid tube 52 along a suture channel formed by suture track 53c of guide member 53 to suture track 58d of guide member 58 through track 56b of coupler member 56, down to the tissue engaging end 16a. Vacuum connection assembly 64 may alternatively be coupled at port 74 to a source for air to provide positive air pressure along the same suture channel, i.e., to drive air down to the tissue engaging end 16a.

A valve 19 is provided at the bottom of handle 30a, as shown in FIGS. 9 and 10, having a valve seat 19a and a valve controller 19b, shown as separate components in FIGS. 19A and 19B. Valve seat 19a is composed of medical grade rubber, such as Santoprene®, and has a hole 76 extending into an interior chamber 78. One side 79 of this chamber 78 has a lip 80 about an opening 81. Protruding into the chamber 78 facing opening 81 is a raised member 82 of the valve seat 19a through which the hole 76 extends to an opening 84, which is recessed near a surface 82a of the raised member 82. The recess of opening 84 forms the shape of an eye having two opposing corners 86 when valve 19 is open. Two opposing fingers 88 of the raised member 82 extend from the top and bottom of the eye of opening 84. A valve controller 19b composed of molded plastic, or other rigid material, has a circular section 90 having an opening 92 to an interior surface forming a cam 94, and a recessed retainer ring 95. Circular section 90 is received through opening 81 such that retainer ring 90 is captured by lip 80 to retain valve controller 19b in valve seat 19a. Fingers 88 and corners 86 of the raised member 82 of the valve seat lie against the surface of cam 94 of the valve controller 19b. The cam surface is wider along one dimension and narrower along a perpendicular dimension, such that when the fingers 88 lie along the narrower dimension, they compress the recess of opening 84 into a closet slit to close valve 19, and when fingers 88 lie along the wider dimension, the recess of opening 84 returns to its normal shape and the valve 19 is open. Adjusting the dimensions of the cam surface 94a controls the amount of pressure applied to compress opening 84, and thus the integrity of the closed valve's seal. Another hole 76b (FIG. 9) extends through opening 92 to the bottom 96a of turn knob 96 of the valve controller. The suture routing tube 47 is received in hole 76 of valve seat 19a, as shown in FIG. 9, such that suture material from the tube can pass through openings 76 and 84 of the valve seat and then through hole 76b of the valve controller.

As shown in FIG. 20A, the valve 19 is open when the finger 88 align along surface 94a and 94b of the cam 94, and corners 86 are each received in corresponding detents 94c and 94d of cam 94. To close valve 19, a turn knob 96 of the valve controller 19b is rotated as shown in FIG. 20B. This starts compressing fingers 88 against the surface of the cam 94 until-the fingers 88 lie in detents 94c and 94d compressing opening 84 of the valve seat to close the valve, as shown in FIG. 20C. To open the valve 19, the turn knob 96 is again rotated until the corners 86 lie in detents 94c and 94d. The turn knob 96 may be rotated clockwise or counterclockwise to open and close valve 19. Valve 19 may be closed to seal the suture tube 47 when suction is applied via vacuum connection assembly 64, but allows suture to be drawn under slight tension through the valve.

Other types of valve 19 may alternatively be used, such as shown in FIG. 19D, which provides a seal, but enables the suture to be drawn under slight tension through the valve. In FIG. 19C, the bottom of handle 30a is shown in which the suture tube 47 is received in a duckbill valve 128 providing a chamber 128a and two flaps 128b extending into the chamber along the length of suture 105 which extends through suture tube 47 between flaps 128b and through an opening 129 in housing 30. In response to negative air pressure in suture tube 47, the two flaps 128b meet along edges 128c providing a seal about the suture 105 in chamber 128a. FIG. 19C illustrates the valve when closed, when open flaps 128b at edges 128c may separate from each other.

Figure 21:
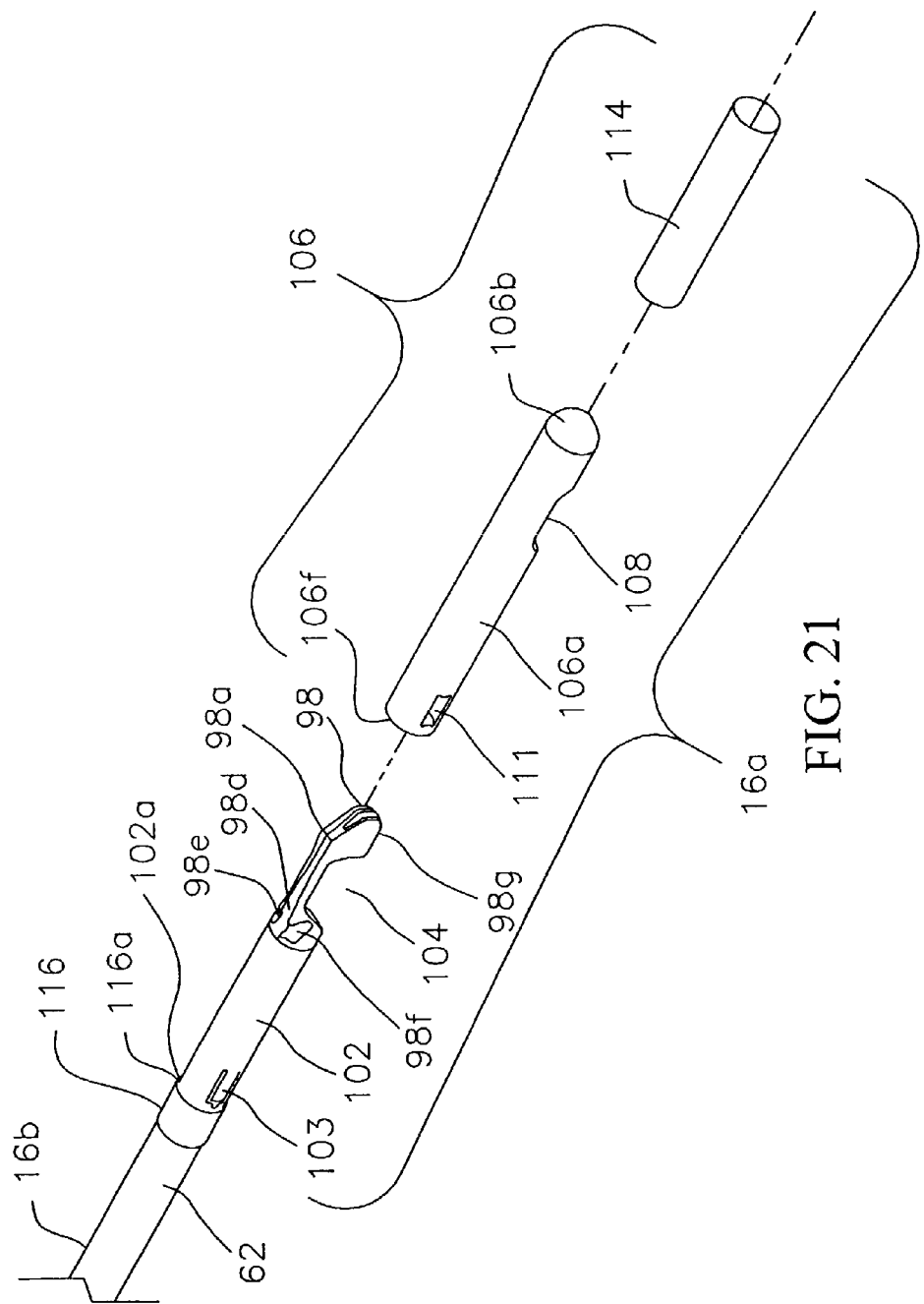
FIG. 21 is an exploded view of the distal end of the suturing instrument of FIG. 9.
Figure 21A:
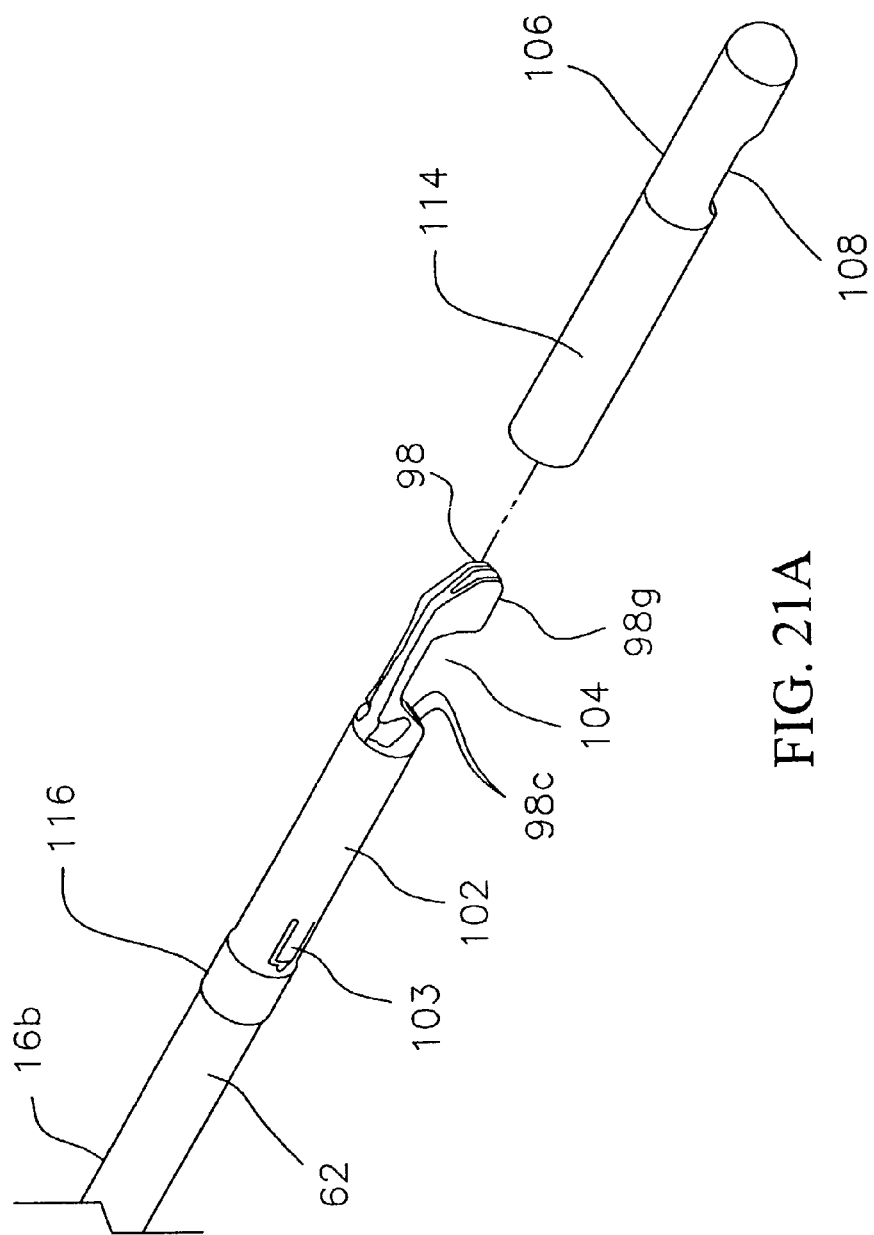
FIG. 21A is an exploded view of the distal end of the FIG. 9 showing the sleeve into which the tissue engaging end of the suturing instrument is received.
Figure 21B:
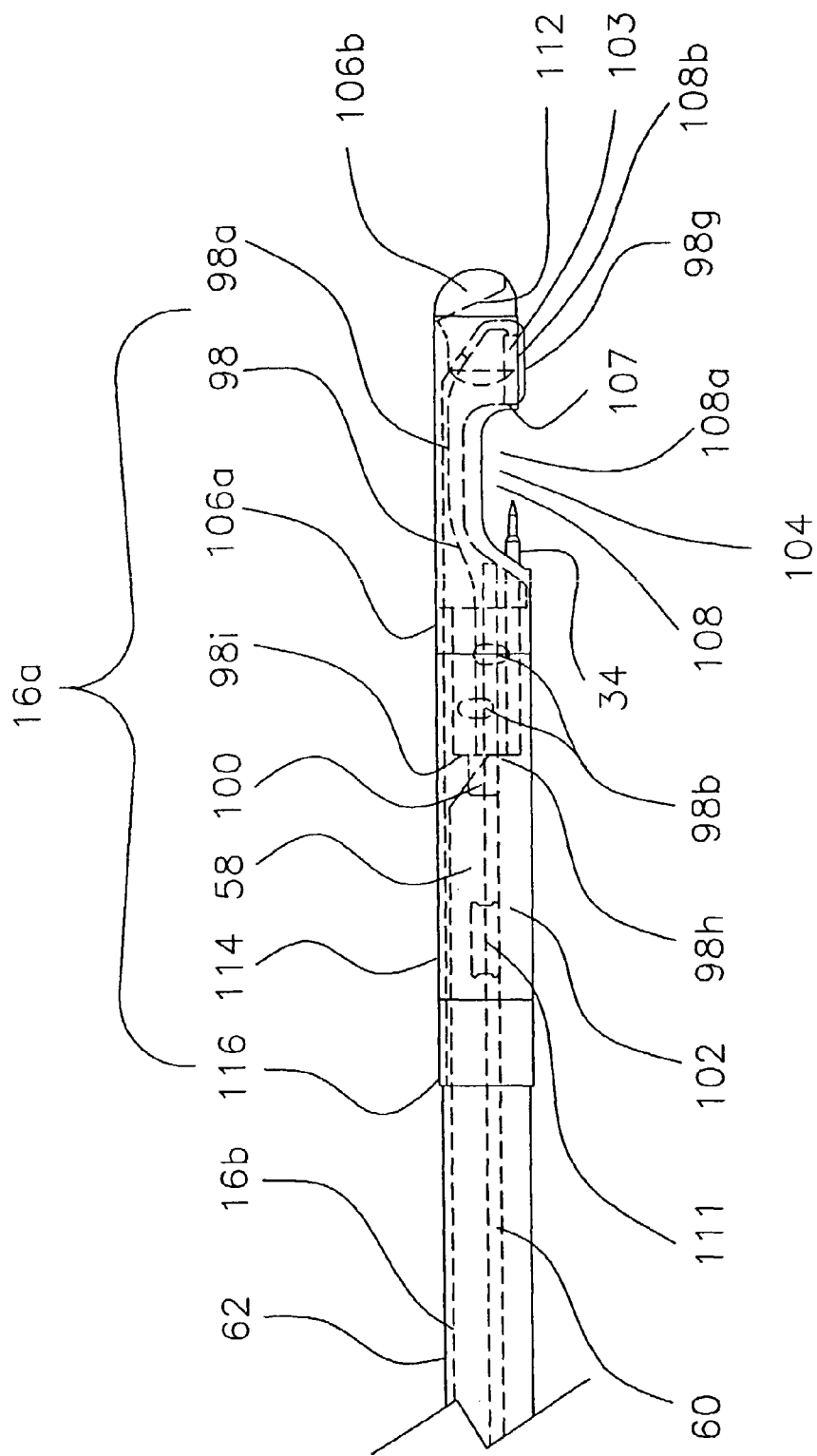
FIG. 21B is a side view of the tissue engaging end of the suturing instrument with the sleeve of FIGS. 21 and 21A.

Referring to FIGS. 21, 21A and 21B, the tissue engaging end 16a of the suturing instrument 16 is shown having the sew tip 98 which is mounted in a tip tube 102, such that the front section 98a of the sew tip extends from tube 102. The mounting of the tip tube 102 to the sew tip 98 may be achieved by mechanical fastening by forming small dents in the metal of the tip tube 102 with a press into recessed four pockets 98b, i.e., two on each side of the sew tip (FIG. 17A). The sew tip 98 has a gap 104 in a C-shaped jaw having two openings 98c at one side of the gap through which each of needles 34 and 35 may extend to capture ferrules 103 having one end of suture material 105 located in openings 107 at the other side of gap 104, and after each needle captures a ferrule, the needle retracts back into their respective opening 98c carrying the suture material on its tip. A channel 98d is provided in the sew tip which aligns with suture track 58c of guide member 58, as shown in FIG. 17B. The channel 98d extends along the length of the sew tip and then fork into two channels, each leading to one of the two openings 107 having ferrules 103 to which the end of the suture thread is attached. Openings 107 retain ferrules 103 but are slotted to enable release of suture after a ferrule 103 is captured. The operation of sew tip 98 will be described in more detail below in connection with FIGS. 22A-22I.

A vacuum sleeve 106 is provided having a tube 106a, and a rounded cap 106b which closes one end of tube 106. The cap 106b has an edge 106c which mates with the edge 106d of tube 106a and two extending flanges 110 which are received in tube 106a to hold the cap in place (FIGS. 21C and 21D). Between flanges 110 the interior surface of the cap is angled to provide a ramp 112 (FIG. 21B). The sew tip 98 in tip tube 102 is received through the open end 106f of tube 106b, such that an opening 108 of tube 106b is located over gap 104 of the sew tip. The two flanges 110 of cap 106d register with the two sides of the forward part 98g of the sew tip 98 to properly align sew tip 98 and tip tube 102 in the vacuum sleeve 106. The opening 108 represents a cut into tube 106a to provide a oval shaped window 108a and a forward slot 108b which extend from window 108a to the end of tube 106a meeting cap 106b, such that the forward (ferrule carrying) part 98g of the sew tip 98 partially extends through slot 108b (FIG. 21B). Cap 106b has a notch 106e located adjacent slot 108b at edge 106d of tube 106a (FIG. 21D). The ramp 112 is negatively sloped at an angle towards slot 108b, as shown in FIG. 21B, to facilitate the suturing process, as will be described later. Two fingers or prongs 103 extend from the sides of the tip tube 102 and are received in two corresponding openings 111 of the vacuum sleeve 106 to latch the sleeve in position over the sew tip. Guide member 58 extends into tip tube 102 as shown in FIGS. 18B21B. Shrink wrap or tubing 114 is then applied over tube 106a, such that openings 111 are sealed closed, to complete the assembly of the vacuum sleeve 106, as shown in FIG. 21A. A short metal ring 116 is placed over the end 102a of the tip tube 102 and the edge of the shrink wrap 62 extending along shaft 18b. In placing ring 116, shrink wrap 62 is first applied over shaft 18b and tube 102, and then cut back to an edge 106a of ring 116. Tubes 102 and 106a are both made of metal, such as stainless steel, and cap 106a may be made of molded plastic. A cross-section of tissue engaging end 16a through the sew tip 98, tip tube 102, and vacuum sleeve 106, is shown in FIG. 17. This vacuum sleeve 106 enables a vacuum or partial vacuum to be applied to the path of the suture following gasket member 51, via the vacuum connection assembly 64, to channel 98d of the sew tip 98, such that the upflow of air into the gap 104 of the sew tip through opening 108 of vacuum sleeve 106 can pull the tissue into the gap. The suction from the vacuum or partial vacuum is applied to gap 104 of the sew tip 98 via two openings 98e in channel 98d to two cavities 98f each located on opposite sides of the sew tip in the space between the sides of sew tip 98 and vacuum sleeve 106 near gap 104 (FIG. 21). Although cap 106b as described herein is preferred, cap 106b may be provided by a metal cap 118, such as of stainless steel attached to the end of tube 106a, and provides a small ramp 118a.

The tissue engaging end of suturing instrument 16 may be as described in U.S. patent application Ser. No. 09/686,420, filed Oct. 11, 2000, which is herein incorporated by reference. This patent application describes the loading of a length of suture material, i.e., thread, whose ends are affixed to ferrules in the sew tip 98. Before such loading, the vacuum sleeve 106 is removed from tube tip 102 by pushing in fingers 103 to release them from openings 111 and then simultaneously pulling the vacuum sleeve 106 away from tube tip 102. After loading, the vacuum sleeve 106 is replaced and latched back (i.e., fingers 103 in openings 111) onto the tube tip 102 and the loop of suture extends from the ferrules through the suture tracks 53a and 58a of guide members 53 and 58 to suture routing tube 47, via track 56b of the coupler member 56 and opening 51a of the gasket member 51, out holes 76 and 76a of valve 19. Proper orientation of the vacuum sleeve 106 over tube tip 102 and sew tip 98 is provided by flanges 111 of cap 106b, as described earlier, and also by ramp 112 being angled such that it prevents upside down misalignment of the vacuum sleeve over the sew tip. The forward section 98g of the sew tip will be stopped by ramp 112 before fingers 103 reach to the tube tip openings 111, preventing the vacuum sleeve 106 from latching. For example, the suture material may represent monofilament suture material or braided suture material.

Figure 22A:
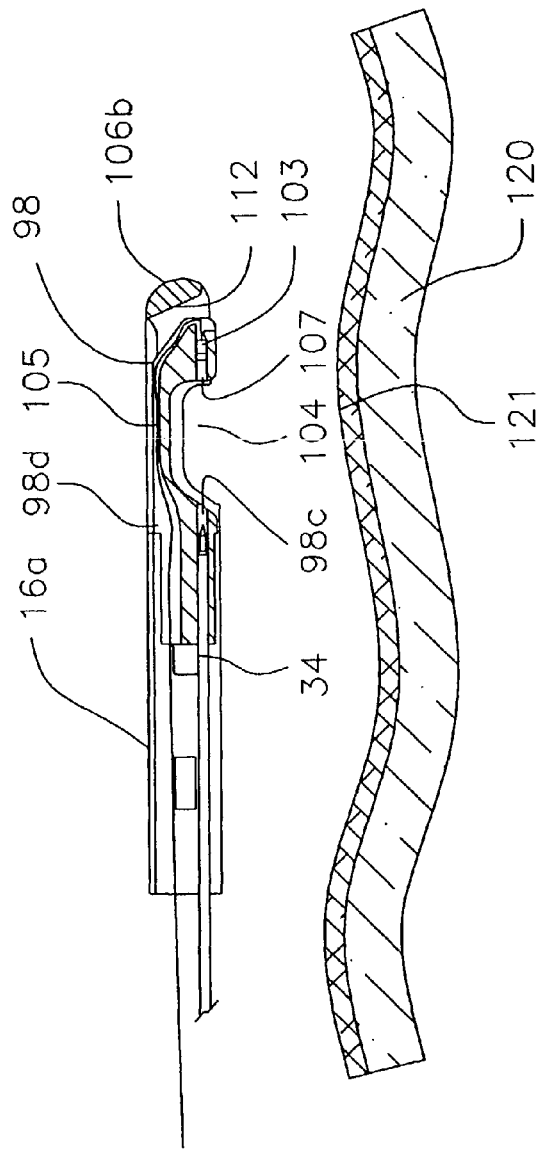
FIGS. 22A-22H illustrates at the tissue engaging end of the suturing instrument the process of applying one end of a loop of suture through tissue with either one the two needles of the instrument.
Figure 22B:
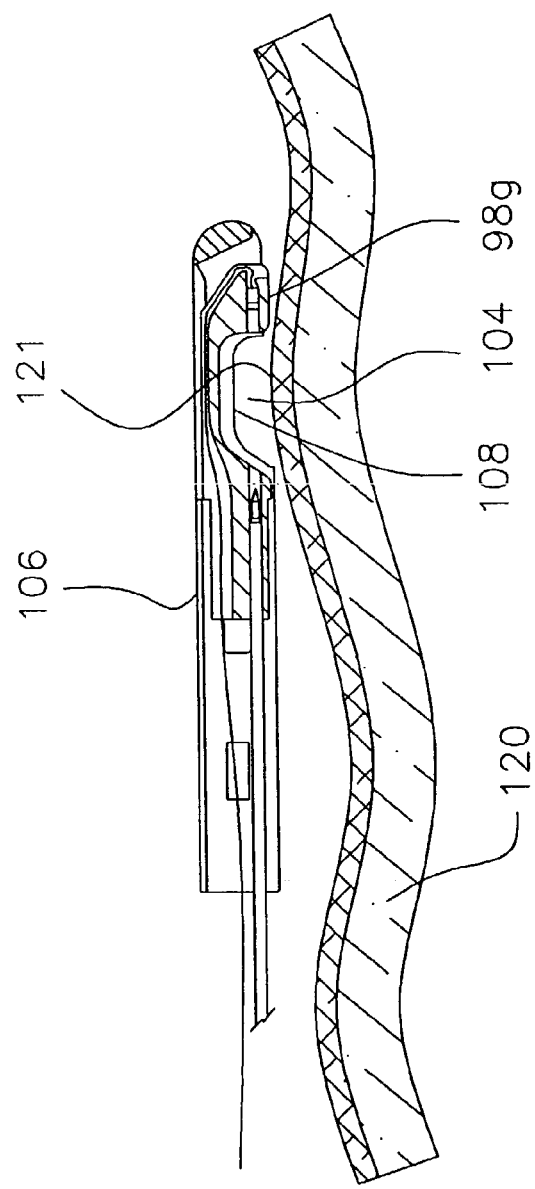
Figure 22C:
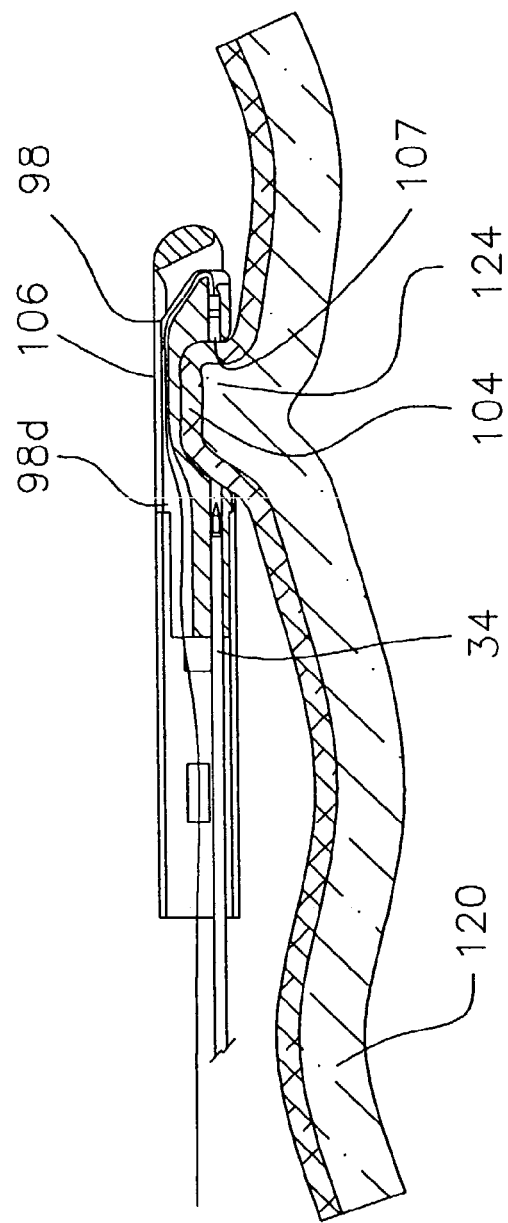
Figure 22D:
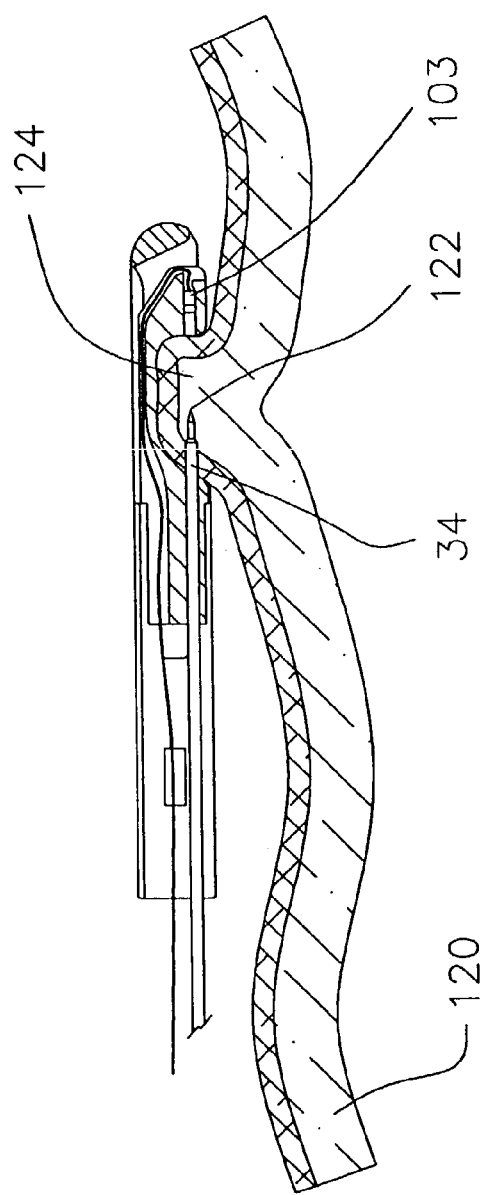
Figure 22E:
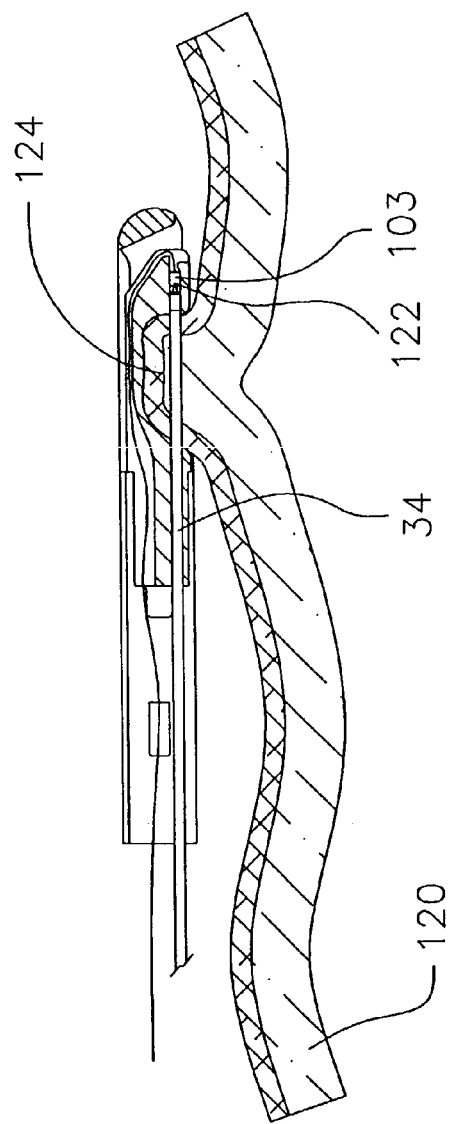
Figure 22F:
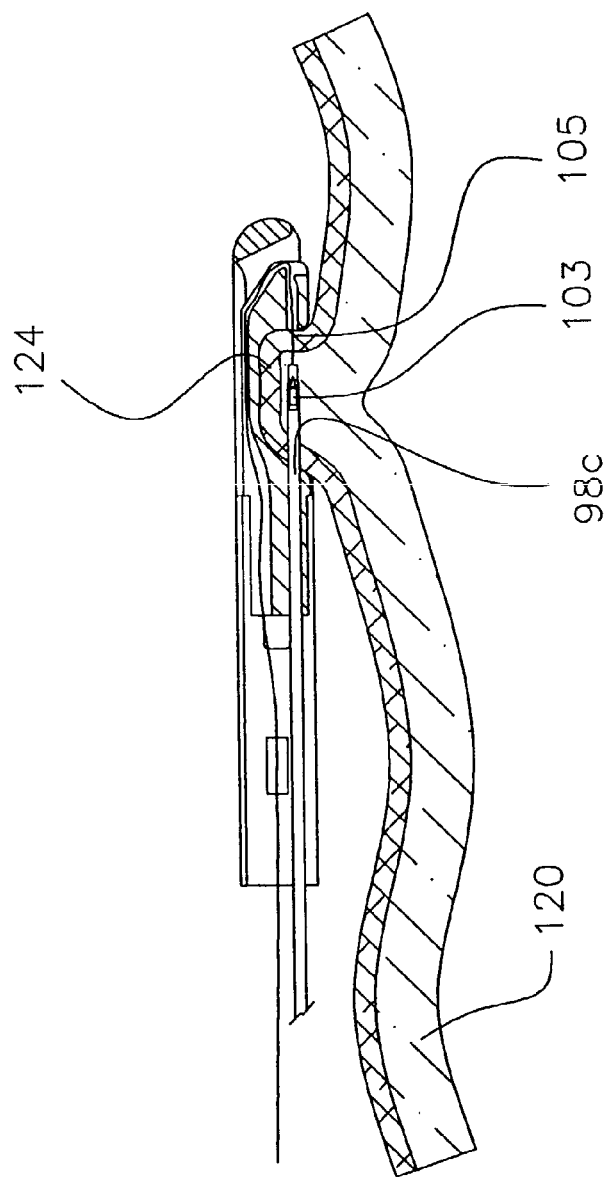
Figure 22G:
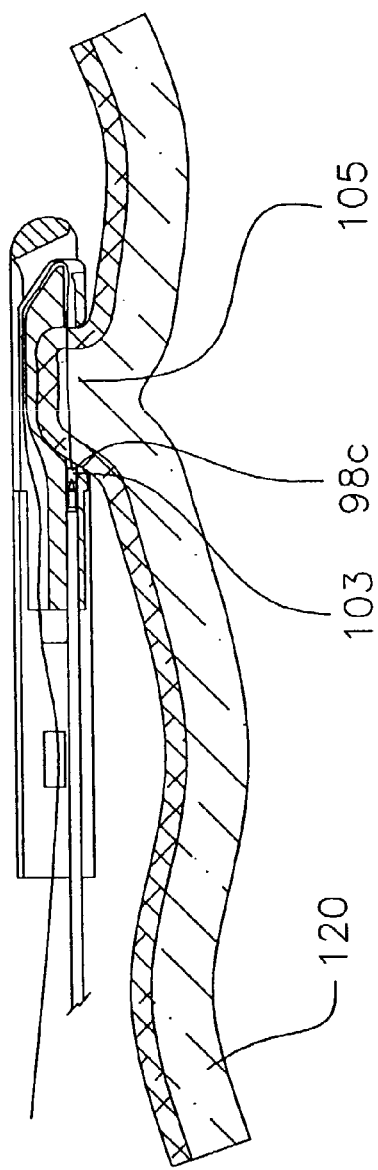
Figure 22H:
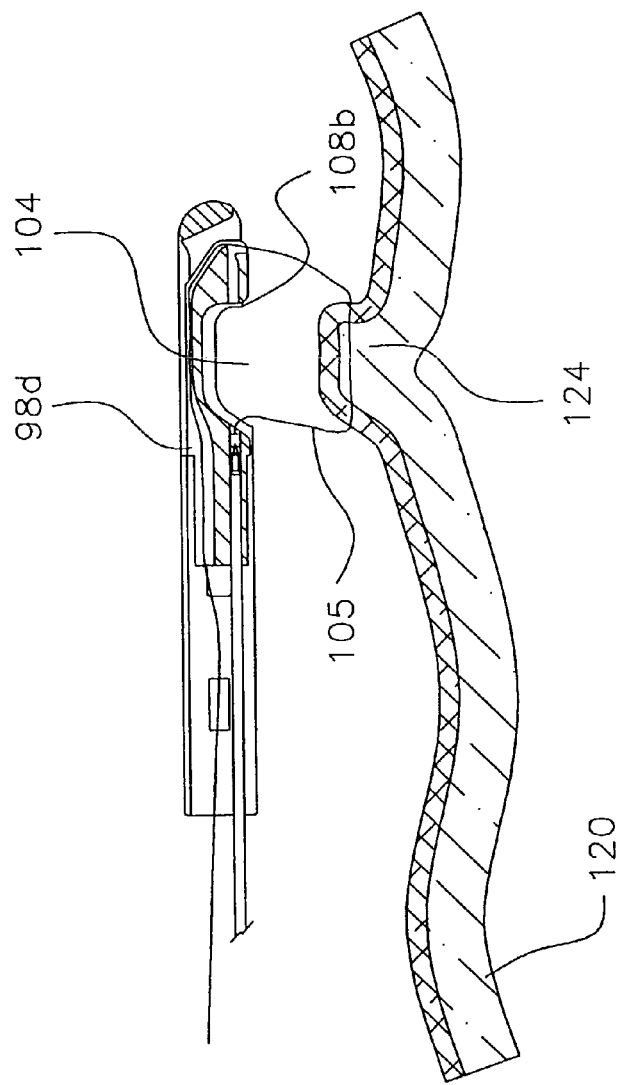
Figure 22I:
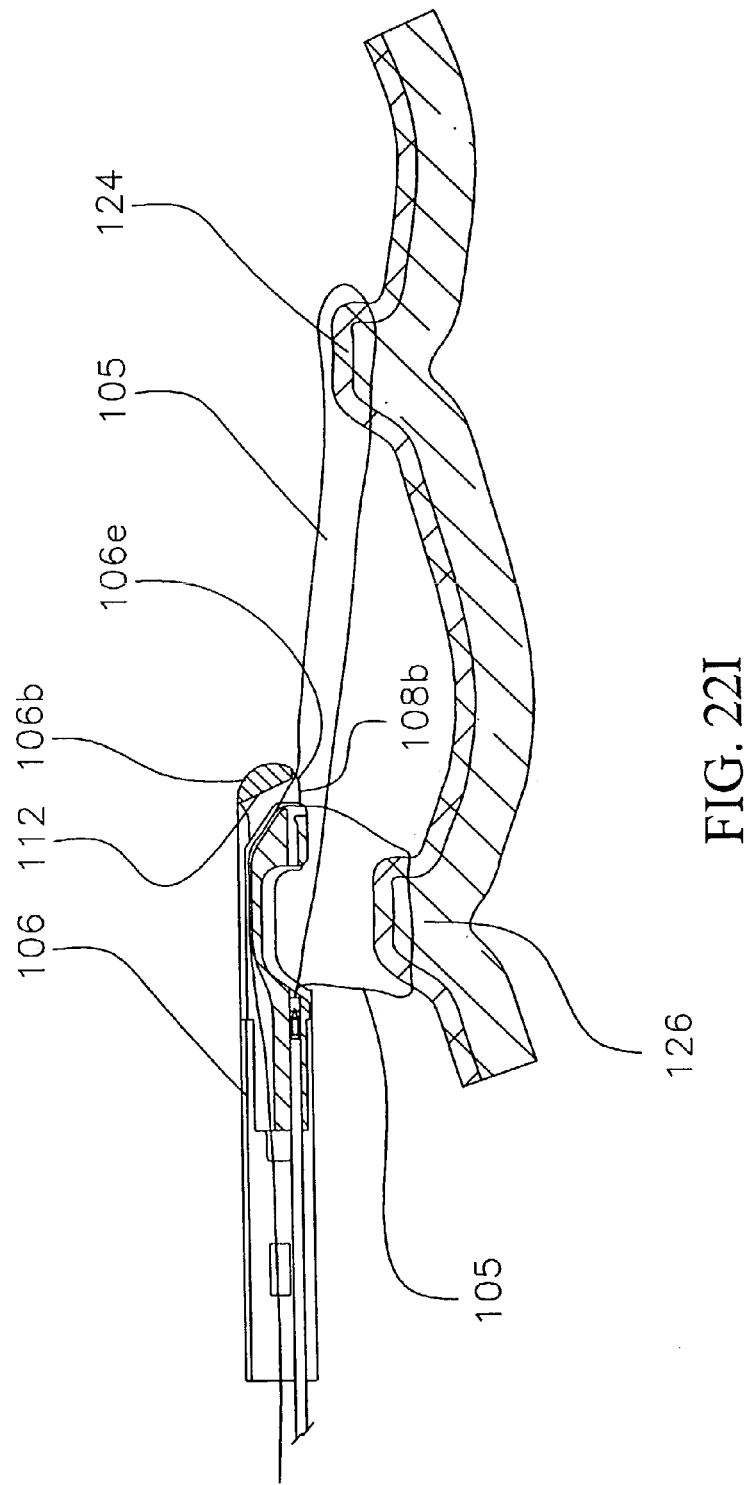
FIG. 22I illustrates at the tissue engaging end of the suturing instrument after both of the needles of the instrument have applied the two ends of the suture loop in the tissue, such that removal of the instrument leaves the suture loop through the tissue.

Referring to FIGS. 22A-22I, the operation of the suturing instrument 16 at the tissue engaging end 16a is shown after the suturing instrument is located, via accessory tube 12, near the tissue to be sutured. FIGS. 22A-22H show the process of applying one end of the suture through tissue 120 with needle 34, the same process is repeated for the other end of the suture for needle 35. Suturing with needles 34 and 35 may be provided in any order. In FIG. 22A, the tissue engaging end 16a is shown with suture material 105 loaded in the sew tip 98, such that the two free ends of the loop of suture extend from the suture track 58a of tube guide 58, via a passage 98d of the sew tip 98, to two ferrules 103 coupled to the two suture ends in the sew tip 98. Opening 98c at one end of gap 104 face ferrules 103 in openings 107 for respectively needles 34 and 35. The tissue engaging end 16a is placed adjacent a first target area 121 in tissue 120 where the first end of the suture will be placed (FIG. 22B). Suction is then applied to pull the target area 121 of tissue 120 via gap 104 of the sew tip through opening 108 in the vacuum sleeve 106 to capture a fold 124 of tissue 120 at target area 121 (FIG. 22C). To apply suction, valve 19 is closed and a vacuum source, such as a vacuum pump 200 (FIG. 29B), provides suction to shaft 16b, via tubing, to port 74 of the vacuum connection assembly 64. The vacuum is communicated into gap 104 via opening 52c of rigid tube 52 to the suction channel in shaft 16b formed by suture track 53c of guide member 53, track 56b of coupler member 56, and then suture track 58d through coupler member 56 to channel 98d and cavities 98f of the sew tip 98. Principally, the suction is applied to cavities 98f, however the suction may occur elsewhere about gap 104, such as the space between the sew tip 98 and the interior surface of the vacuum sleeve 106, or via openings 107. With the suction maintained, and needle 34 selected by an operator using selector lever 44, and the actuator member 36 is pulled by the operator towards handle 30a (FIG. 8), the needle passes through the tissue (FIG. 22D) and then into ferrule 103 (FIG. 22E), such that the tip 122 of the needle is captured in the ferrule. Although valve 19 is closed, the suture may be drawn through the valve seat 19a. The actuator member 36 rotates against the bias of spring 38 until needle tip 122 engages ferrule 103. The amount of rotation of actuator member 36 depends on the distance the needle must transverse before engaging a ferrule, such distance may vary depending on the degree of flexing of shaft 16b along its flexible section 33. The needle 34 is then retracted by the operator releasing actuator member 36, to pass the needle and captured ferrule 103 back through the tissue (FIG. 22F) and into opening 98c (FIG. 22G). The suction generates negative air pressure near the tissue 120 sufficient to pull the tissue into gap 104 of the sew tip 98 without damaging the tissue. The suction is then discontinued, such as by turning off the vacuum source 200, and the valve 19 opened to release the tissue from gap 104 of the sew tip (FIG. 22H). The end of the suture thread extends from the captured ferrule on the needle tip through tissue 120 to channel 98d. The suture releases through the slot extending along opening 108b and the suture extends from captured ferrule through the tissue to channel 98d. The process of FIGS. 22A-22H is then repeated at a second target area in the tissue with needle 35 selected to place the second end of the suture in the tissue. FIG. 22I shows the result after both suture ends are placed through tissue, where one suture end extends through tissue fold 124 and the other through fold 126. For example, the second target area may be located directly after placing the first suture end through the tissue by rotating the housing 30 of the instrument 180 degree to rotate the tissue engaging end 180 degrees. The entire operation is observed by the operator via the gastroscope, and in this manner, the first and second target located by the operator in the tissue. The operator may be a surgeon, gastroenterologist, or other skilled physician.

Figure 23:
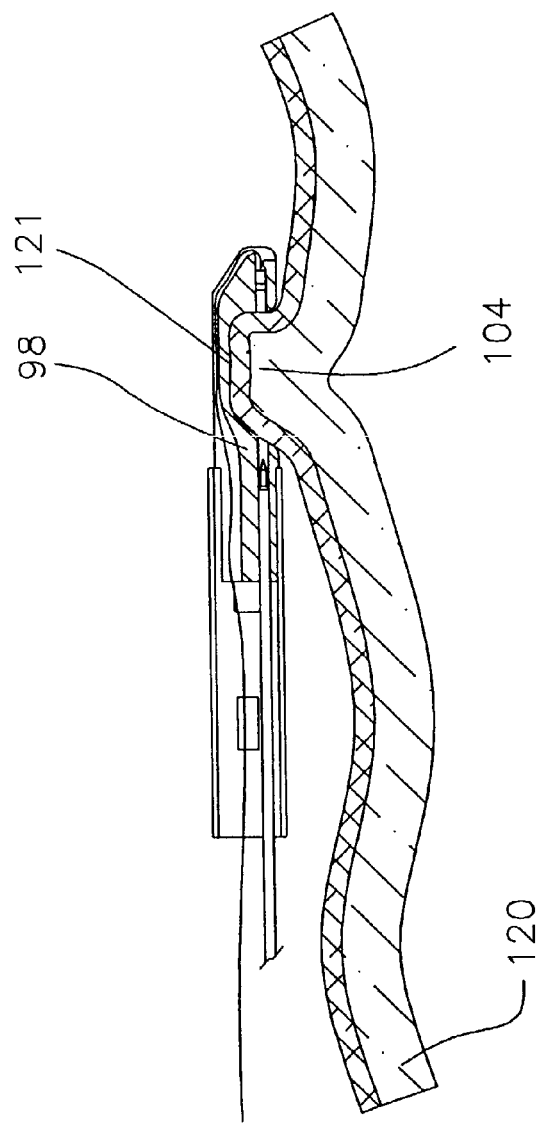
FIG. 23 illustrates the operation of the tissue engaging end of the suturing instrument in accordance with another embodiment of the instrument without the outer sleeve of the tissue engaging end, where suction is not needed to capture tissue in applying a suture.

Alternatively, the suturing instrument may operate to apply a suture without suction if the target area of tissue can be sufficiently received in gap 104 of the sew tip 98. For example, the target area may represent a raised portion of tissue to be sutured. Further, the suturing instrument operating without section, may be used with the vacuum sleeve 106 removed from the tissue engaging end 16a, such as shown for example in FIG. 23.

After two ends of the suture have been placed through the tissue, as illustrated in FIG. 22I, the suturing instrument 16 is removed from the accessory tube 12, which pulls the loop of suture, which extended from housing 30, down to tissue 120. As the suture passes through the tissue engaging end 16a, the suture follows from channel 98d of the sew tip over the ramp 112 and notch 106e of cap 106b. The suture may then be secure by a suture securing instrument 130 described below.

Referring to FIGS. 30, 30A, 46, 46A, 47, 48, 48A, 49-63, 59A, 63A, 64, 64A, 65, 65A and 65B, another embodiment of the suturing instrument of system 10 is shown. In this embodiment, the suturing instrument 216 has the same components as suturing instrument 16 at housing 30 and through the rigid section 32 of the shaft 216a of the instrument, and such components have identical reference numbers. The components of the flexible section 233 of shaft 216a extending to the distal tissue engaging end 216b, vacuum housing assembly 256, and the tissue engaging end 216 including the sew tip 248 assembly, are described below for suturing instrument 216.

Needles 234 and 235 extend through needle guide tubes 234a and 235a, respectively. The proximal ends 234b and 235b of needle guide tubes 234a and 235a, respectively, frictional engage in holes 51b and 51c, respectively, of gasket 51 (FIGS. 11 and 13). Needle guide tubes 234a and 235a maybe of flexible stainless steel tubing and are of a diameter larger than the needles such that the needles are extendible and retractable through their respective guide tube. Needle guide tubes 234a and 235a may also be made of flexible reinforced plastic, pebex, polyurethane tubing, or nickel titanium tubing, such as nitnol. The needles 234 and 235 are each of unitary construction. The components along the shaft's flexible section 233 of suturing instrument 216 (e.g., at least needle guide tubes 234a, 235a and needles 234, 235) are substantially flexible so as enable flexure or bending as shown for example in FIG. 46.

Figure 51:
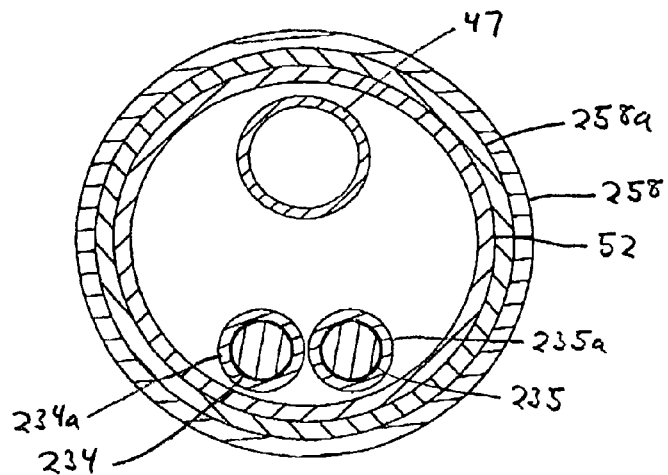
FIG. 51 is cross-sectional view along lines 51-51 of FIG. 48.
Figure 52:
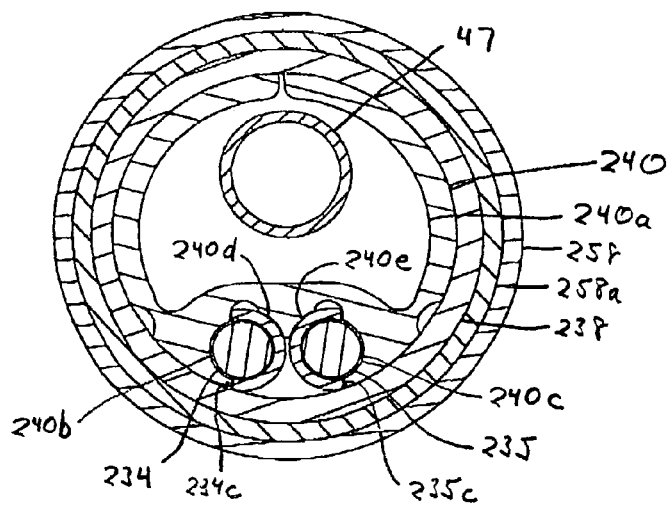
FIG. 52 is cross-sectional view along lines 52-52 of FIG. 48.

The rigid tube 52 is coupled by a proximal coupler 240 to a flexible body 238, which extends along the entire length of the shaft's flexible section 233. The flexible body 238 may be a tube of plastic, polyurethane, or other flexible material with a metal mesh or braiding along its length. The outer diameter of the flexible body 238 is substantially the same as the outer diameter of rigid tube 52. The proximal coupler 240, shown in cross-section in FIG. 52, has a cylindrical body with a first opening 240a for the suture guide tube and openings 240b and 240c for the needles 234 and 235 in their respective needle guide tubes 234a and 235a. Each needle guide tube 234a and 235a has a longitudinal opening or window 234c and 235c, respectively, cut along a segment of its lengths, which engages a semicircular longitudinal slot 240d and 240e, respectively, cut in the diameter of openings 240b and 240c, respectively, and thereby locking the needle guide tubes to the proximal coupler 240. The proximal coupler 240 extends about half its length into the end 52b of the rigid tube 52 and is attached to the rigid tube, such as by staking (i.e., pressure deforming the tube) into two indents or holes on each side of the proximal coupler. End 238a of flexible body 238 is pressed over the other half of the proximal coupler 240 in abutment to the rigid tube 240a, such that the flexibly body frictionally engages the outer cylindrical surface of the proximal coupler having a diameter which enable such press fit. Once assembled, shrink wrap layer or tubing 258a may be applied to cover the interface of the rigid tube 52 and flexible body 238 and extends partially along the rigid and flexible sections 32 and 233 of shaft 216a. FIG. 51 shows a cross-section of shaft 216a prior to proximal coupler 240, and FIG. 52 shows a cross-section through the proximal coupler 240 and flexible body 238.

Figure 53:
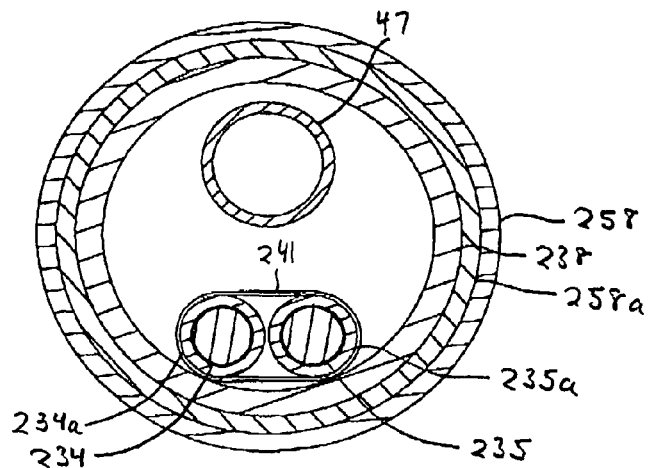
FIG. 53 is cross-sectional view along lines 53-53 of FIG. 48.
Figure 54:
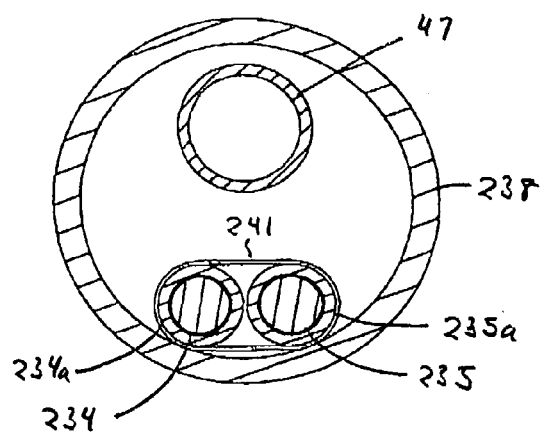
FIG. 54 is cross-sectional view along lines 54-54 of FIG. 48.
Figure 55:
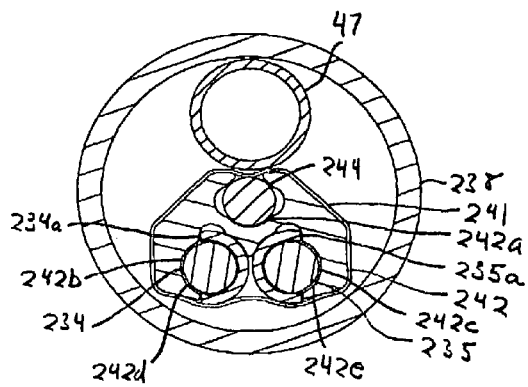
FIG. 55 is cross-sectional view along lines 55-55 of FIG. 48.
Figure 56:
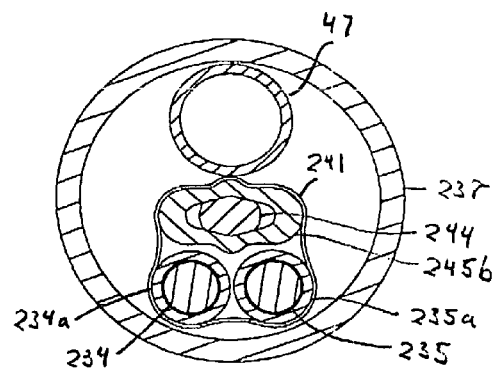
FIG. 56 is cross-sectional view along lines 56-56 of FIG. 48.
Figure 57:
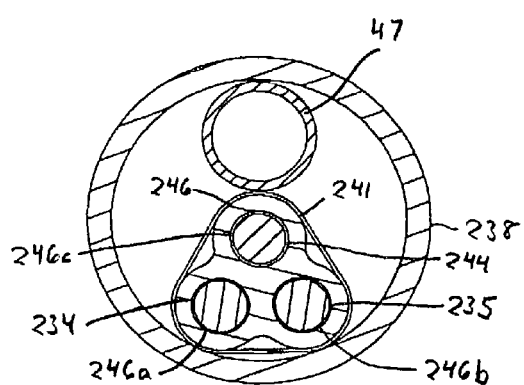
FIG. 57 is cross-sectional view along lines 57-57 of FIG. 48.
Figure 58:
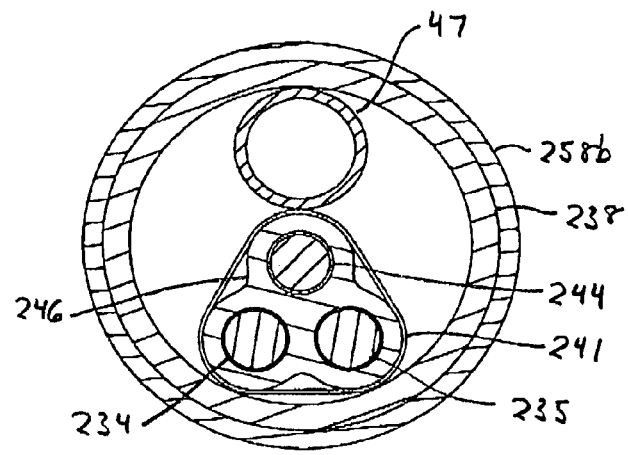
FIG. 58 is cross-sectional view along lines 58-58 of FIG. 48.

After the proximal coupler 240, the needles 234 and 235 extend in their respective needle guide tubes 234a and 235a until a middle coupler 242. Cross-sections of shaft 216a between the proximal and middle couplers are shown in FIGS. 53 and 54. Middle coupler 242 has a first opening 242a for a cable or braided wire 244 to extend therethrough and then longitudinally fixed in the coupler by two ferrules or metal tubes 245a and 245b, which are crimped (i.e., pressure deformed) over the cable 244 on either side of middle coupler 242. Two longitudinal openings 242b and 242c are provided in coupler 242 for needle guide tubes 234a and 235b having needles 234 and 235, respectively. Each needle guide tube 234a and 235a has another longitudinal opening or window 234d and 235d, respectively, cut along a segment of its length, which engage a semicircular longitudinal slot 242d and 242e cut in the diameter of each opening 242b and 242c, respectively, and thereby locking the needle guide tubes to middle coupler 242. The needle guide tubes 234a and 235b extends slightly distally after middle coupler 242, while the cable 244 extends slightly proximally before the middle coupler to engage ferrule 245a. A cross-section of shaft 216a through middle coupler 242 is shown in FIG. 55, and through crimped ferrule 245b in FIG. 56. Cable 244 may be of stainless steel wire(s).

Figure 60:
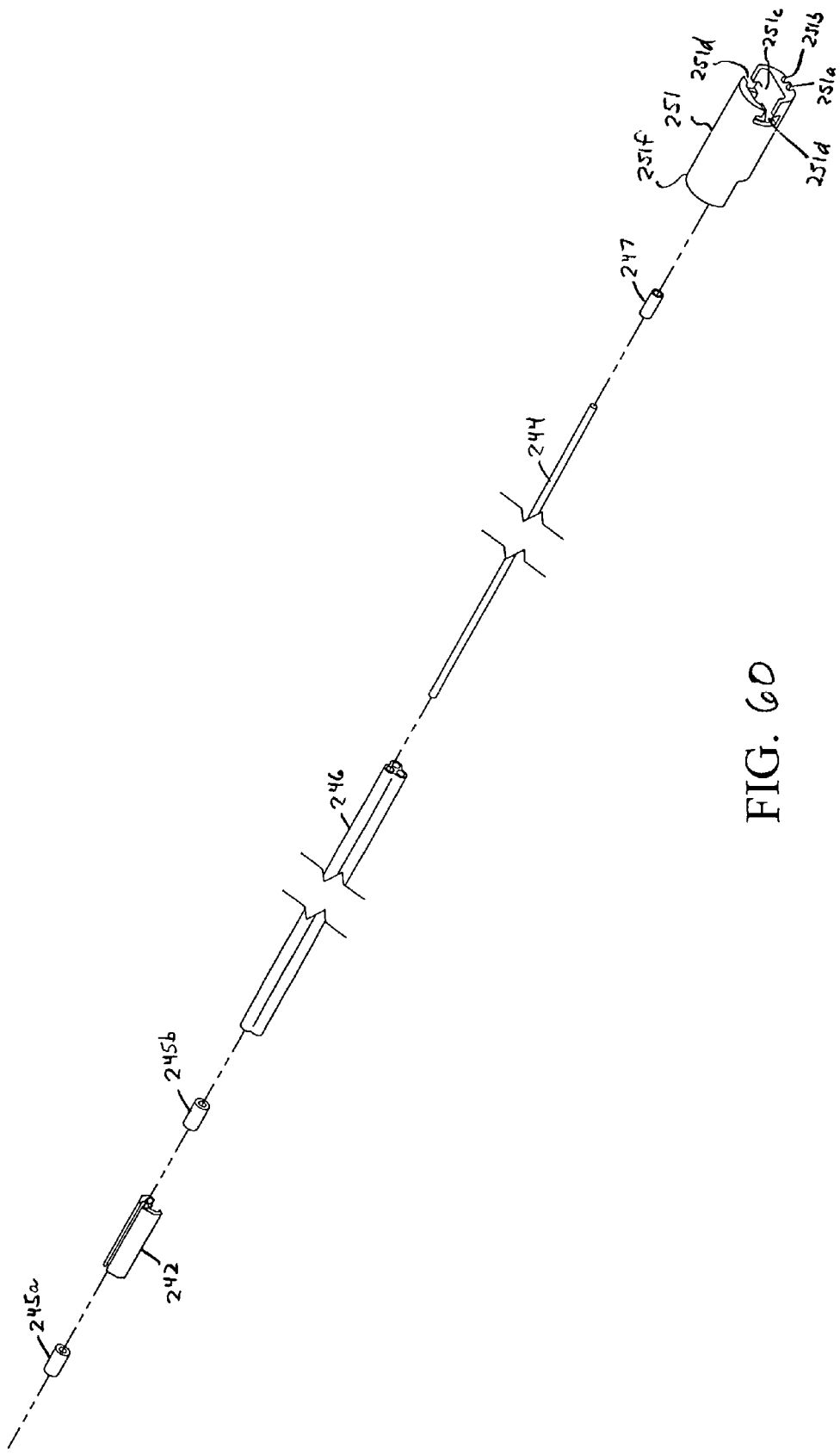
Figure 62:
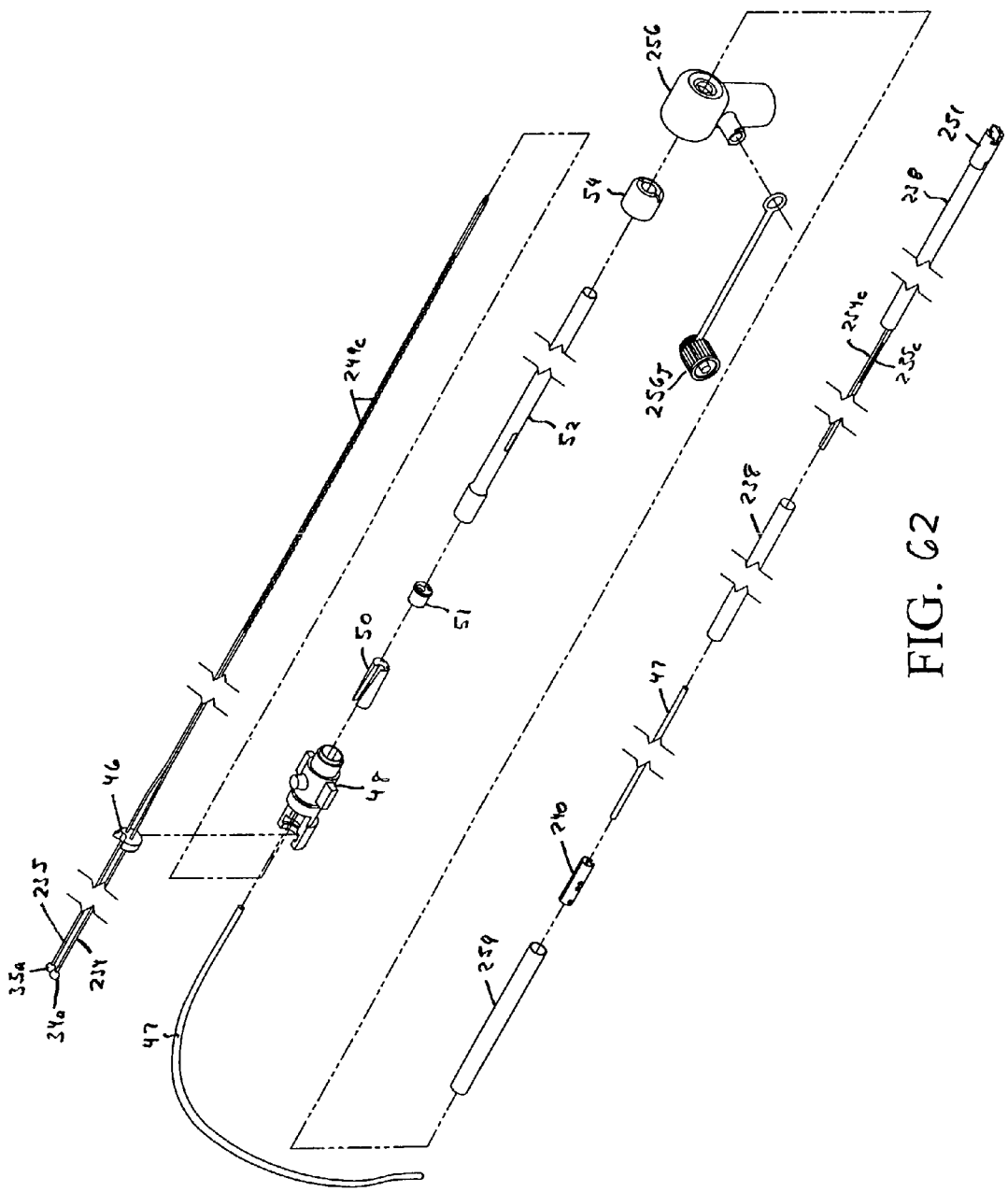
Figure 63:
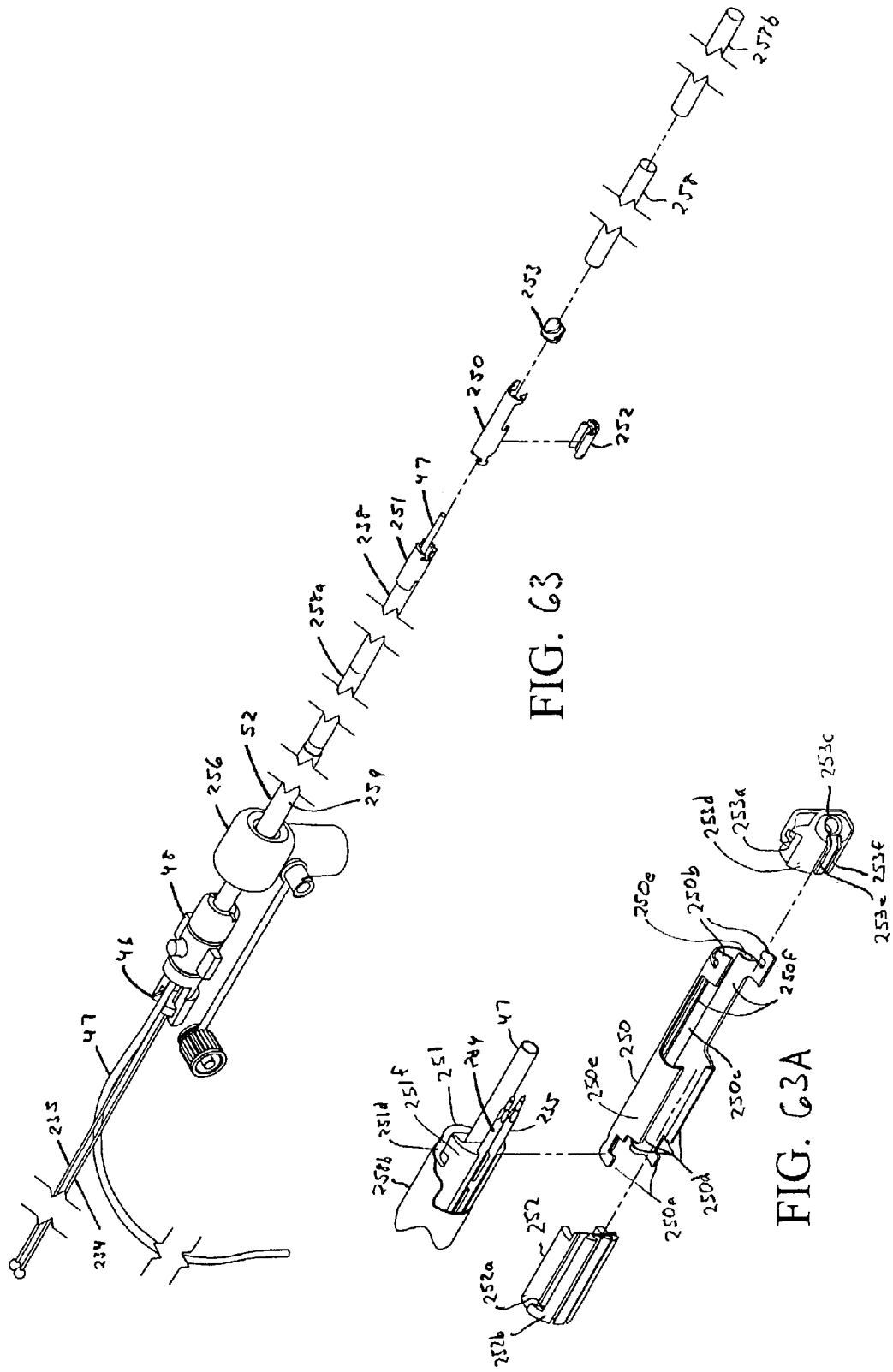

Needles 234 and 235 exit from their respective needle guide tubes 234a and 235a and pass through channels or openings 246a and 246b, respectively, of a flexible guide member 246. Cable 244 extends through channel or opening 246c of guide member 246. The flexible guide member 246 may be made of extruded flexible material, such as Tecoflex®. An internal plastic shrink-wrap layer or tubing 241 is applied over the needle tube guides 234a and 235a after they exit the proximal coupler 242, and over middle coupler 242, ferrules 245a and 245b, and flexible guide tube 246, as illustrated in FIGS. 53-58. Once applied, such tubing 241 is of heat shrinkable material, such that it is secured in place by application of heat. FIG. 60 shows an exploded view of the ferrules 245a and 245b, middle coupler 242, and distal coupler 251 without the internal shrink-wrap layer.

Figure 64A:
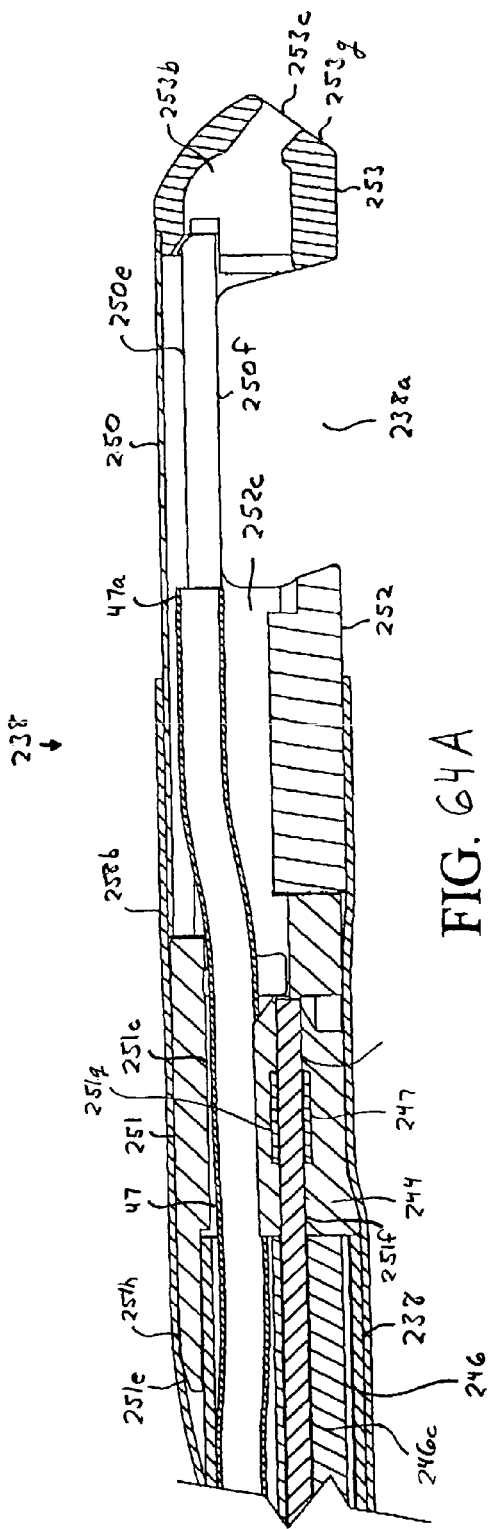
FIG. 64A is a cross-sectional view along lines 64A-64A of FIG. 64.

The flexible guide member 246 extends through the flexible body 238 until the distal end 238b of the flexible body, which abuts surface 251i of a distal coupler 251. The distal end 238b of the flexible body 238 also abuts the distal coupler 251 under its ledge 251h, which has a curved interior surface substantially matching the curved outer surface of flexible body 238 (FIG. 64A). The flexible body 238 may be attached to the distal coupler 251 by adhesive under ledge 251h, or by other bonding means.

The distal coupler 251 is a cylindrical shaped body with two channels 251a and 251b for receiving needles 234 and 235, respectively, exiting flexible guide member 246, an opening 251c for suture tube 47, and two key slots 251d. Near distal end 244a of cable 244, the cable is crimped (i.e., pressure deformed) to a metal tube or ferrule 247. To attach the cable 244 to the distal coupler 251, the wire with crimped ferrule 247 are insert molded when the distal coupler is molded of plastic or other biocompatible material. Once molded, the cable 244 extends through opening 251f of distal coupler 251 and the ferrule is captured is a pocket 251g of the distal coupler 251, thereby attaching the distal coupler to the cable 244. Such attachment to distal coupler 251 occurs prior to passage of cable 244 through guide member 238 and middle coupler 242.

The distal coupler 251 is attached to sew tip 248 of the instrument. The sew tip 248 is composed of a frame body 250 into which a needle track section 252 and ferrule holder section 253 is attached, as best shown in FIG. 63A. Although the sew tip 238 is composed of multiple integrated components, the sew tip 238 may be provided by a single body. The needle track section 252 slides into the back of frame body 250 in which an undercut provided along edges 252a of each side of the needle track section mates with edges 250d of the frame body. To attach the sew tip to the distal coupler 251, two key or tabs 250a which extend from the sides of frame 250 are located in key slots 251d of the distal coupler, thereby aligning the channels 251a and 251b with channels 252a and 252h of the needle track 252. Similarly, two keys 250b extend from the sides of frame body 250 and located in key slots 253a in ferrule holder section 253 to attach the ferrule holder section to the frame body. Once assembled, the outer surfaces 250e, 252e, and 253d of the frame body, needle track section, and ferrule holder section, respectively, are substantially continuous. The proximal coupler 240, middle coupler 242, frame body 250, needle track 252, and ferrule holder 253 may be made of metal, such as stainless steel, and manufactured using electrical discharge machining (EDM) processes, but other materials such as molded plastic, or other biocompatible material, may be used.

Figure 64:
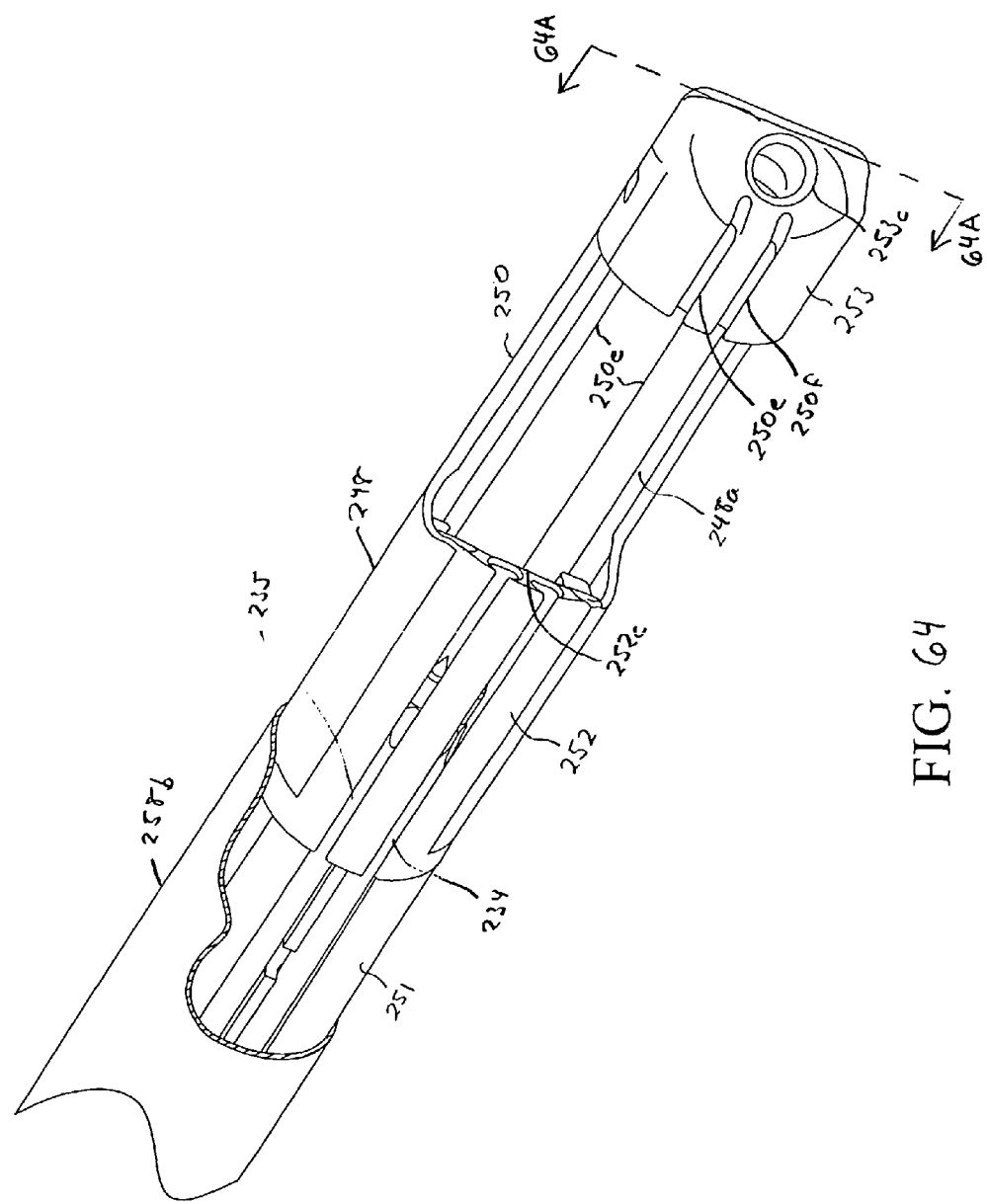
FIG. 64 is a partial broken view of the sew tip of the suturing instrument of FIG. 46.

The assembled sew tip 248 coupled to the distal coupler 251 defines the distal end 216b of instrument 216, as shown in FIGS. 48A, 64, and 64A. An outer shrink-wrap layer or tubing 258b is provided at the distal end prior to gap 248a and extends partially along the flexible shaft section 233. Once applied, tubing 258b is of heat shrinkable material such that it is secured in place by application of heat. In regards to outer shrink wrap tubing 258, such tubing extends along the shaft 216a from the vacuum housing 256 (or spaced 1-3 inches from the housing) over shrink wrap tubing 258a and ends along the flexible shaft section 233, for example, at a point before middle coupler 242, then no outer shrink wrap tubing is present (FIGS. 54-57) until shrink wrap tubing 258b (FIGS. 58-59), which may extend for about three inches until just before gap 248a of the instrument 216. Optionally, a single shrink-wrap tubing may be used rather than two tubings 258 and 258b from about the vacuum housing 256 along shaft 216b and ending prior to gap 248 at the distal end 216b. For purposes of illustration, FIGS. 60-63 show shaft 216a of suturing instrument 216 being assembled from the distal coupler 251 back through the shaft. However, other assembly order may be used.

The suture tube 47 extends from valve 19 through housing 30 and rigid tube 52, as described earlier, through opening 240a of proximal coupler 240, the interior of flexible body 238, and opening 251c of the distal coupler 251, and then into sew tip 248 where the distal end 47a of the suture tube 47 is received in a cavity 252c defined by the interior surface 250c of the frame body 250 and the needle track section 252. The ends of a loop of suture each extend through the suture tube 47, and then after exiting the suture tube, extends through gap 248a of the sew tip 248 into a cavity 253b of ferrule holder section 253, and then through a hole or opening 253c of the ferrule holder section 253 extending from cavity 253b, and attach to a sleeve member or ferrule in the ferrule holder section 253. Such sleeve member or ferrule is described earlier in connection with suturing instrument 16. The ferrules are aligned in openings 253e and 253f with needle channels 252a and 252b, respectively, at the opposite side of gap 248a to enable capture of each ferrule by their respective needle when extended across the gap. Openings 253e and 253f are slotted to enable release of suture when the suturing instrument 216 is withdrawn after capture of the ferrules on the respective needles, such that loop of suture is drawn through the suturing tube 47 and hole 253c of the sew tip 248 through the sutured tissue. Also, the hole 253c may be funnel shaped at surface 253g of the ferrule holder section 253 to facilitate loading of suture, where loading of a length of suture material, i.e., thread, whose ends are affixed to ferrules in the sew tip may be as described in above incorporated U.S. patent application Ser. No. 09/686,420.

Figure 65:
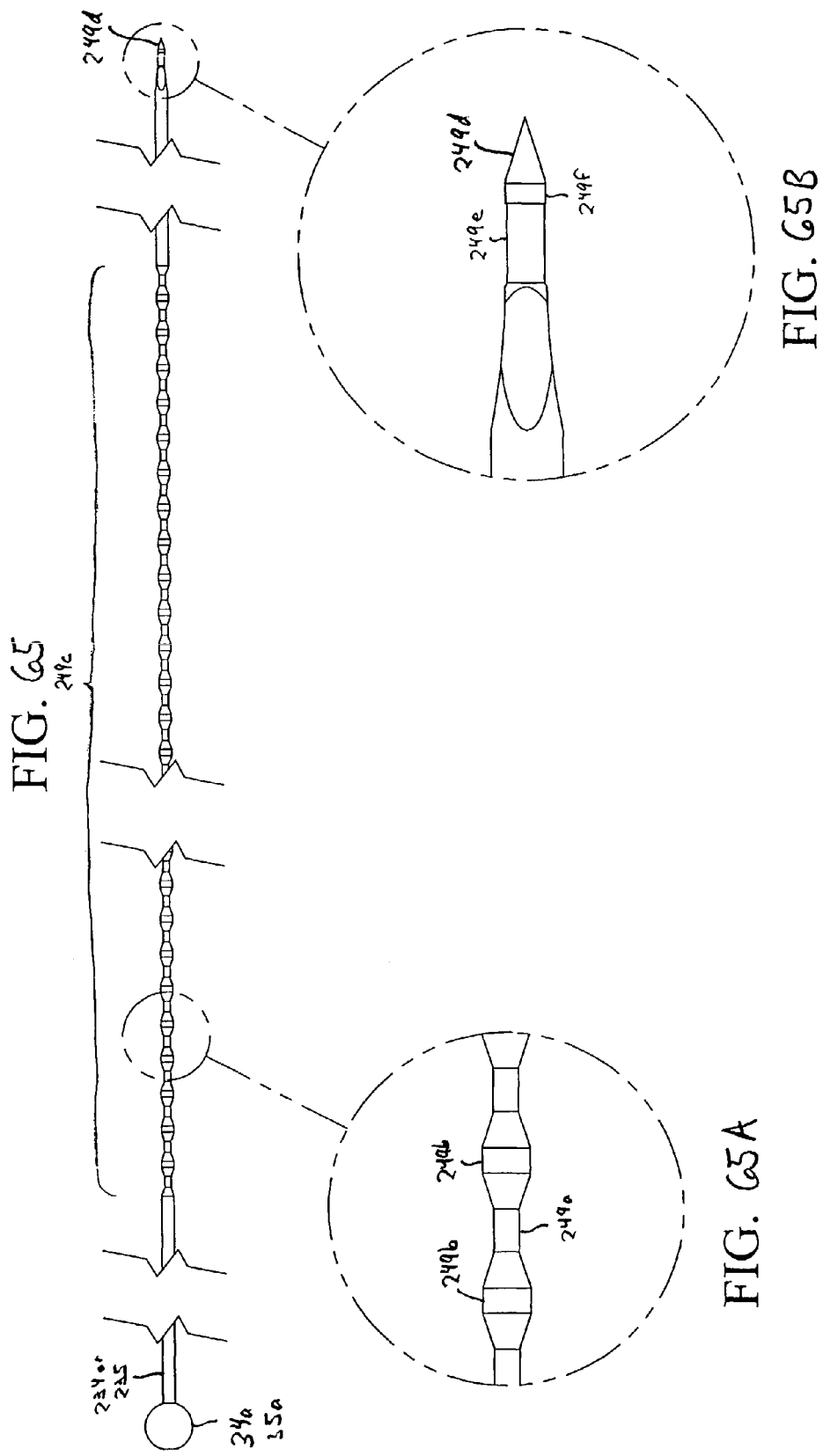
FIG. 65 is a detailed view of one example of the needles of the suturing instrument of FIG. 62.

Referring to FIGS. 65, 65A and 65B, the flexibility to the needles 234 and 235 is enhanced by providing over a section 249c of each needle a series of undulating narrow diameter regions 249a alternating with larger diameter regions 249b. For example, larger diameter regions may each be 0.032 inches and narrow diameter regions 0.017 inches in diameter, and each region 249a and 249b are 0.018 inches in length, and taper between adjacent regions 249a and 249b is about 0.02 inches in length. Section 249c may extend over the entire length of flexible section 233 of shaft 216a or a portion of its length depending on the extent of flexibility needed from such needles. Although the diameter changes along the needle, the needles can be compressed when driven forward. For example, the section 249c of each needle may extend about 6-7 inches in the vicinity between the middle coupler 242 and distal coupler 251 to provide enhanced flexibility to the shaft 216*b* over this extent. Section 249*c* may be achieved on each needle by grinding the diameter of the needle 234 and 235 down to provide such regions 249*a* between regions 249*b*. Near the tip 249*d* of each needle 234 and 235, the outer diameter of the needle is shaped to assist in capture of ferrules, as shown in FIG. 65B, in which section 249*e* of each needle is of a smaller diameter than section 249*f* of each needle before sharpening to tip 249*d*. Each ferrule is of a tubular diameter to snap fit onto section 249*f* when captured upon their respective needle.

Figure 46:
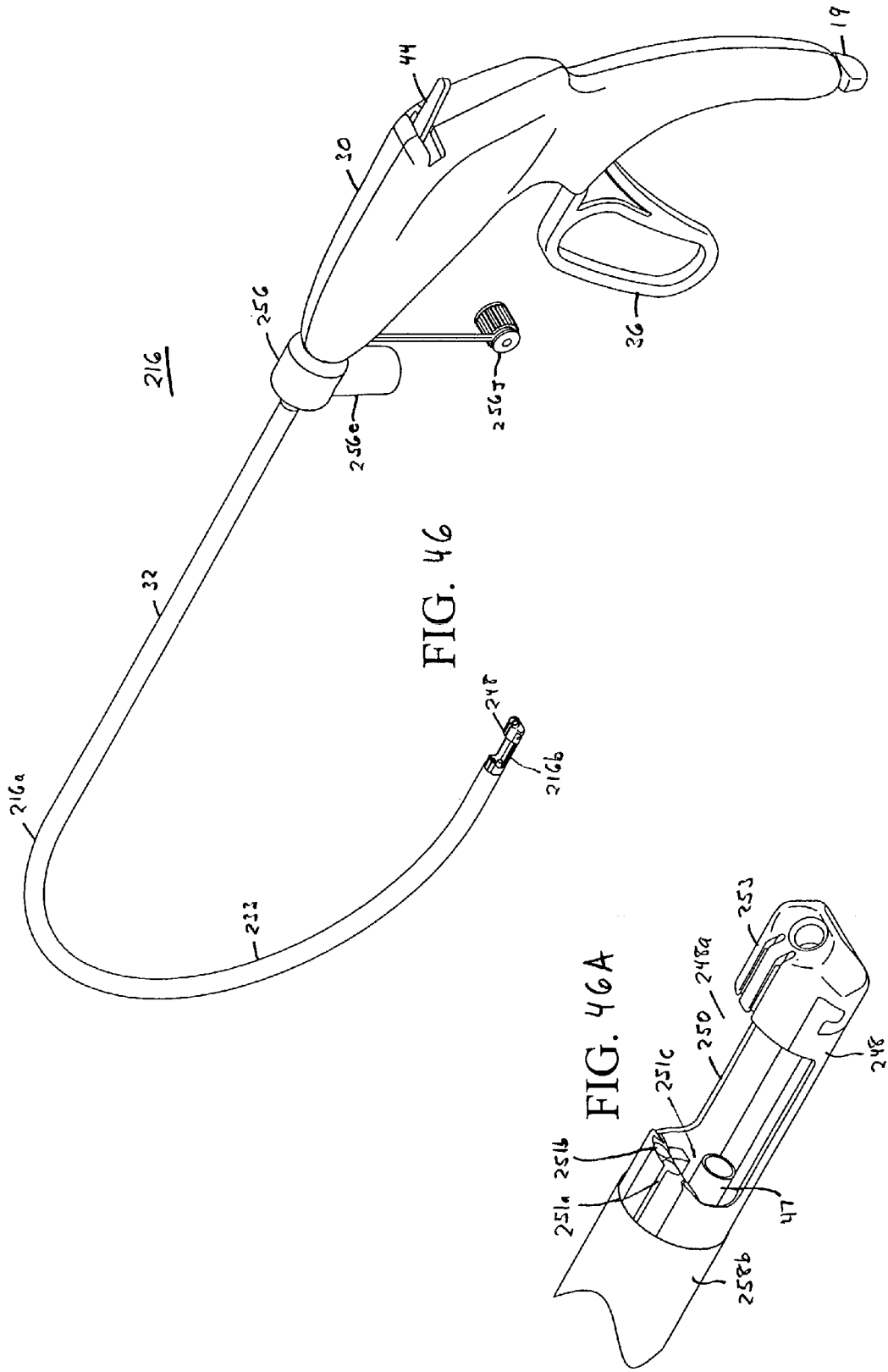
FIG. 46 is a perspective view of the embodiment of the suturing instrument of FIG. 30.
Figure 47:
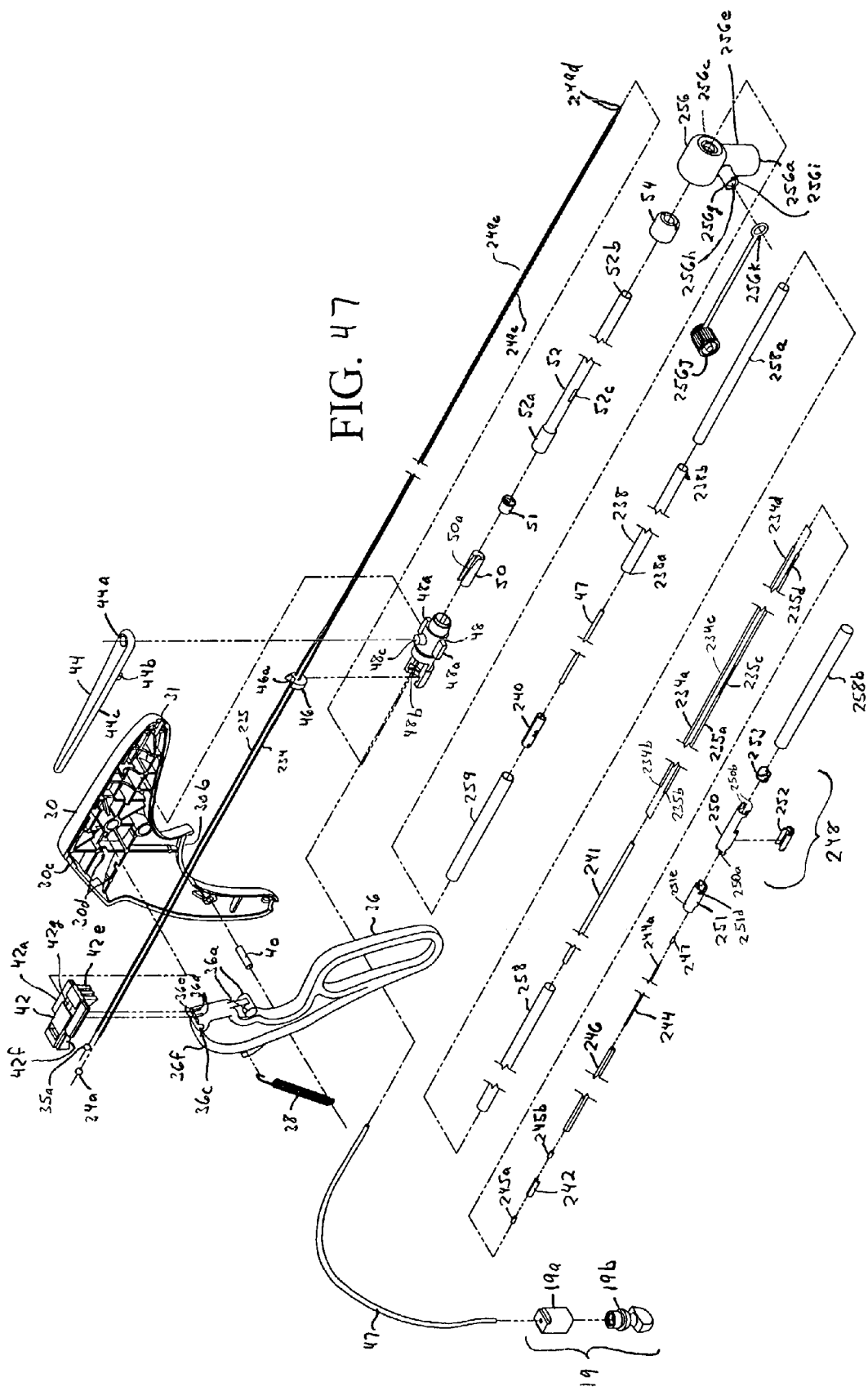
FIG. 47 is an exploded view of the suturing instrument of FIG. 46 in which the right cover of the housing is removed.
Figure 48:
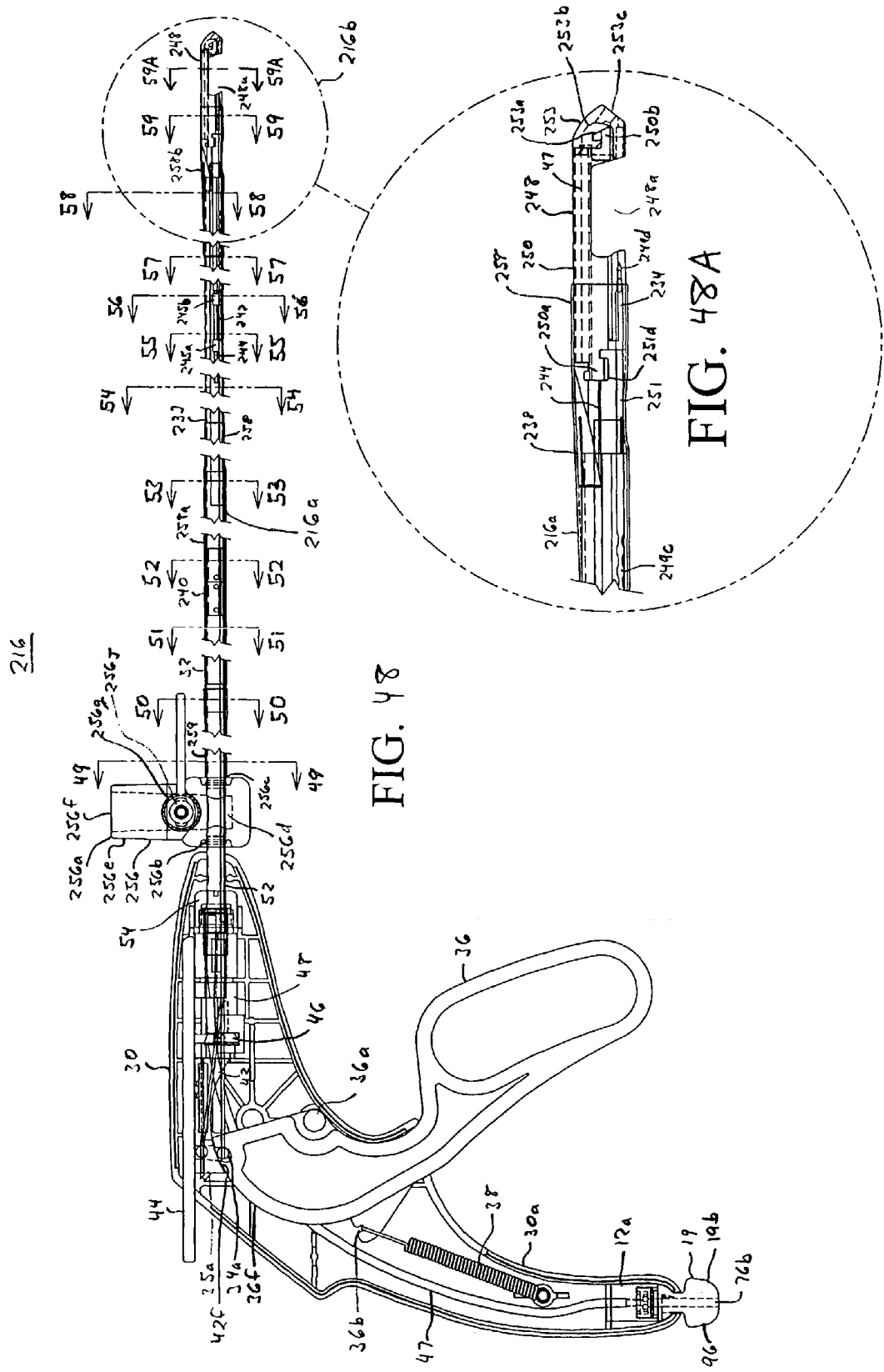
FIG. 48 is a side view of the suturing instrument of FIG. 46 in which the right cover of the housing of the instrument is removed.

Referring to FIGS. 46-48, suction can be communicated via port 256*a* of a cylindrical vacuum housing 256 coupled to shaft 216*a* to the tissue engaging end 216*b*. The vacuum housing 256 is coupled to rigid tube 52, and has two openings 256*b* and 256*c* to a chamber 256*d* through the rigid tube 52 extends. The diameter of openings 256*b* and 256*c* is smaller than the outer diameter of rigid tube 52, such that material about these openings sealingly engages the rigid tube. The vacuum housing 256 also has an extension 256*e* with an opening 256*f* to chamber 256*d* for receiving a fitting member 72, described earlier, such as a valve or stop cock, having a port 74 with a bore 75 to chamber 256*d*. Opening 256*d* may be threaded for attaching to the fitting member. Vacuum housing 256*a* has another extension 256*g* to an opening 256*h* of a port 256*i*. A cap 256*j*, such as a luer cap, is provided upon port 256*i* so as to close this port 256*i* when not needed. A ring 256*k* may couple the cap 256*j* to port 256*j*.

Figure 49:
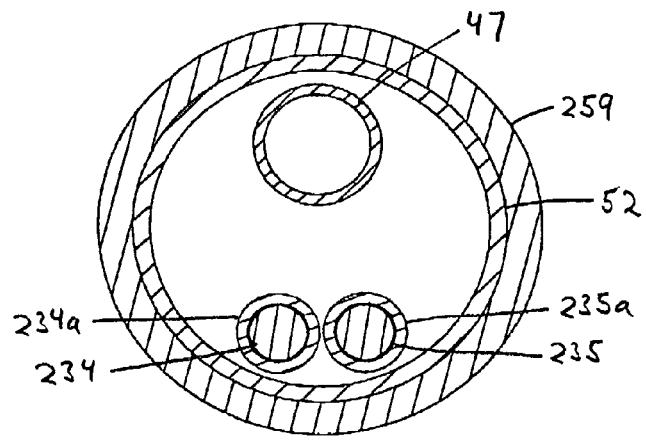
FIG. 49 is cross-sectional view along lines 49-49 of FIG. 48.
Figure 50:
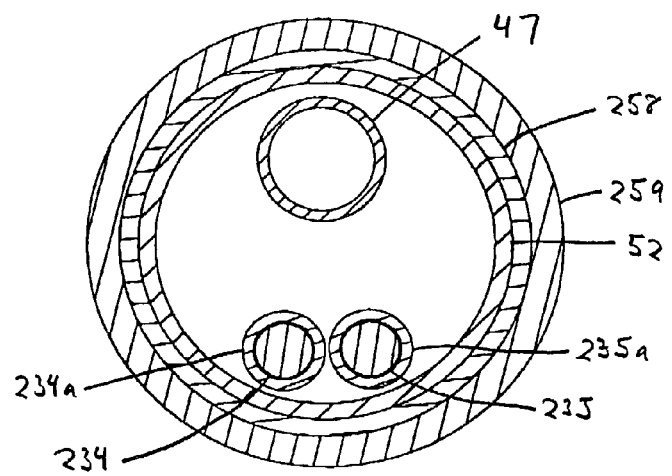
FIG. 50 is cross-sectional view along lines 50-50 of FIG. 48.

The rigid tube 52 has an opening 52*c* (or two openings along opposite tube sides) to the interior of tube 52 which are in communication with chamber 256*d*. The vacuum housing 256 may be rotatable around the rigid tube 52, but limited in longitudinal movement along shaft 216*a* by housing 30, and a stop tube 259 disposed over the rigid tube adjacent opening 256*c*. The stop tube 259 may be composed of heat shrinkable material, such that it is secured in place by application of heat. The vacuum housing 256 may be made of molded polypropylene plastic or other plastic material. A cross-section of the shaft 216*a* through the stop tube 259 is shown in FIG. 49.

After the shaft 216*a* is assembled as described above with vacuum housing 256 upon the rigid tube 52, a plastic shrink wrap layer or tubing 258 may be installed over the stop tube 259, and then shrunk in response to applied heat onto exposed surfaces of shaft 216*a*. Preferably, as shown in FIG. 46 and cross-section of FIG. 50, the shrink tubing 258 is applied upon the rigid tube 52 and stop tube 259 applied over tubing 258.

Figure 59:
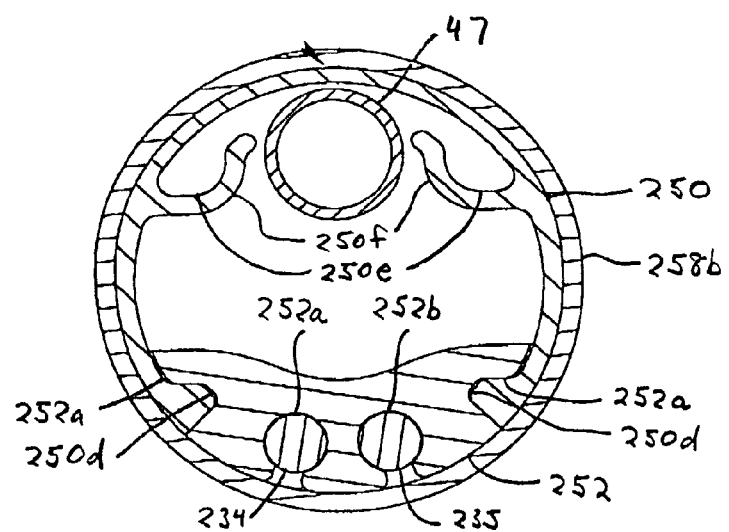
FIG. 59 is cross-sectional view along lines 59-59 of FIG. 48.
Figure 59A:
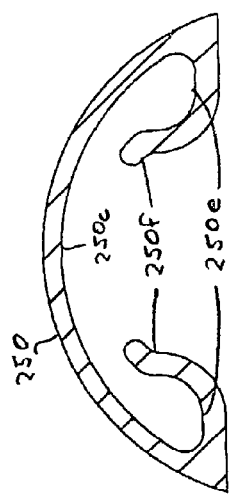
FIG. 59A is a cross-sectional view along lines 59A-59A of FIG. 48.

Suction can be communicated from vacuum housing 256 through shaft 216*a* to the sew tip 248. The channel or path of the suction, i.e., negative air pressure, extends through the rigid tube 52, via opening(s) 52*c*, opening 240*a* of the proximal coupler 240, the flexible body 238 in the space outside interior tubing 241 and suture tube 47, opening 251*c* of the distal coupler 251 in the space outside suture tube 47 through cavity 252*c* into gap 248*a* of the sew tip, and along two longitudinal channels 250*e* each formed by J-shaped flanges extending from interior surface 250*c* of frame body 250 from cavity 252*c* through gap 258*a*. Cross-sections of the sew tip 248 showing channels 250*e* are shown in FIGS. 59, 59A, and 64A. In operation, when the gap 248 is presented at a tissue site to be sutured, suction is provided to the vacuum housing 256, as described earlier, and communicated to gap 248*a*, such that the tissue is pulled into the gap and into cavity 252*c*, while channels 250*e* distribute the suction across the gap to maintain engagement of the tissue as needles are selectably actuated to capture ferrules. Similarly, such channel or path of suction may be used for passage of fluids to the gap 248*a* through port 256*i* of vacuum housing 256, if needed.

The flexible body 238 substantially defines the extent of the flexible section 233 of shaft 216*a*, while the rigid tube 52 substantially defines the extent of the rigid section 33 of the shaft 216*a* after exiting housing 30. For example, the outer diameter of the shaft 216*a* may be 0.203 inches, and the outer diameter of the assembled sew tip 248 may be 0.231 inches. The length of suturing instrument 216 along shaft 216*a* from the vacuum housing 256 to the end of the distal tissue engaging end 216*b* may be similar to the length of shaft 16*b* of suturing instrument 16, such that the distal tissue engaging end 216*b* when inserted through the accessory tube 12 or 212 extends out the distal end of the accessory tube. For example, the length of instrument 216 from housing 30 along shaft 216*a* and distal tissue engaging end 216*b* may be between 31-32 inches (e.g., about 31.5 inches), of which the rigid shaft section (from housing 30 to the distal end of the proximal coupler 240) is about 6 inches, and flexible shaft section 233 (from distal end of the proximal coupler 240 to the proximal end of the distal coupler 251) is about 25 inches, in which the length of the distal end of middle coupler 242 until the distal tissue engaging end 216*b* is between 6 and 7 seven inches.

The operation of suturing instrument 216 for passage of the instrument through accessory tube 12 or 212, applying suction to gap 248*a* at tissue engaging end 216*b* to capture tissue and extending and retracting needles 234 and 235 through such tissue to capture ferrules is similar to that described above for suturing instrument 16. The advantage of suturing instrument 216 is that there are fewer components than instrument 16, and the mechanical snap fit provided easier manufacture at lower cost. Further, suturing instrument 216 has enhanced flexibility of the flexible section as the guide tube 58 of instrument 16 has been replaced with flexible body 258 and needle guide tubes 234*a* and 235*a*, and is further enhanced in the flexible section 233 by the use of flexible guide tube 246, coupling cable 244 between the middle coupler 242 and distal coupler 251, and undulating regions of small and large diameters along needles 234 and 235. Also, suction can be achieved in gap 248*a* of the sew tip in suturing instrument 216 without a vacuum sleeve 106 of instrument 16. The enhanced flexibility of instrument 216 can allow additional flexibility to follow in accessory tube the flexures of the shaft of the endoscope 14.

Figure 24:
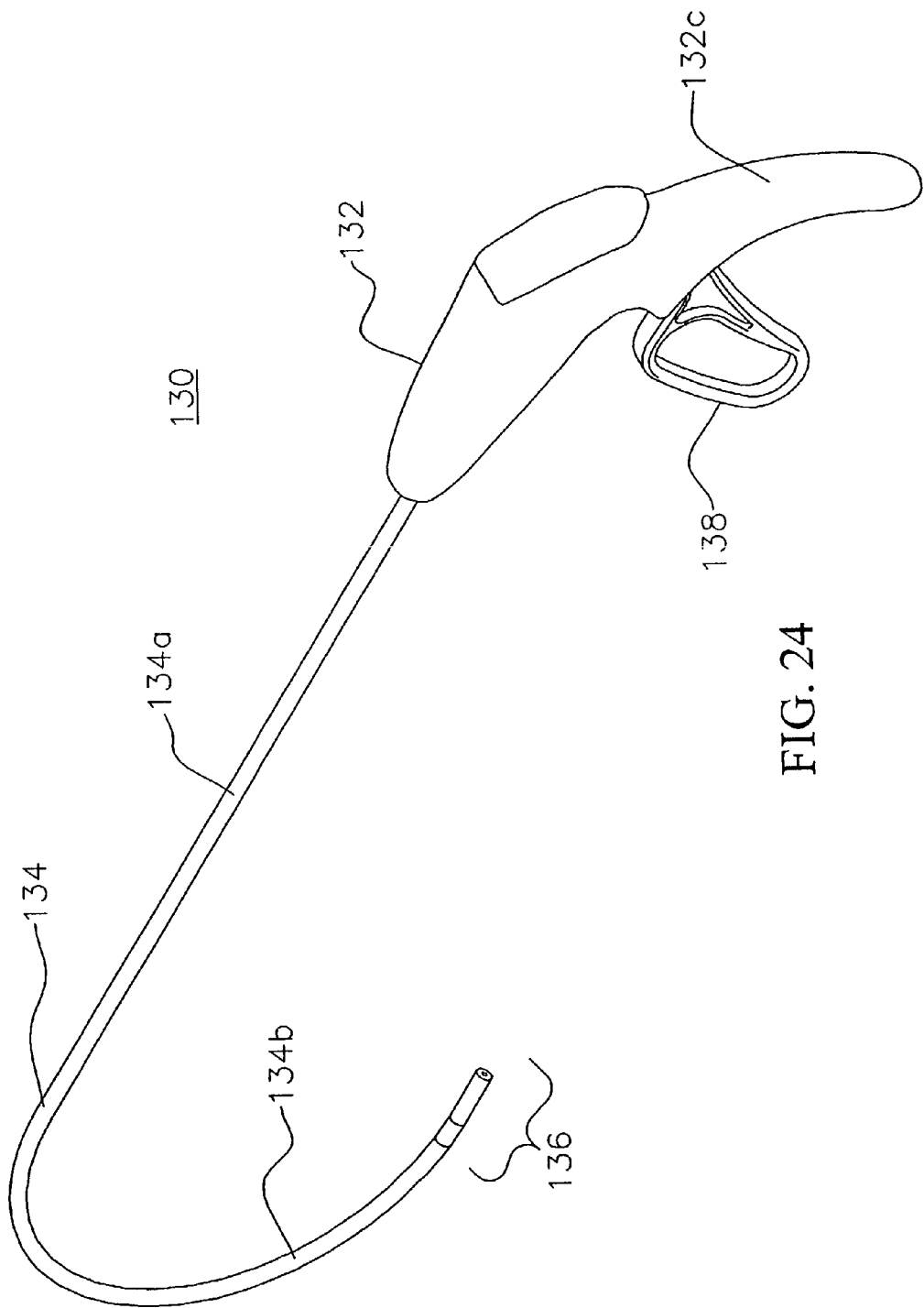
FIG. 24 is a perspective view of the suture securing instrument of the system in accordance with the present invention to retain close the suture applied by the suturing instrument.
Figure 24A:
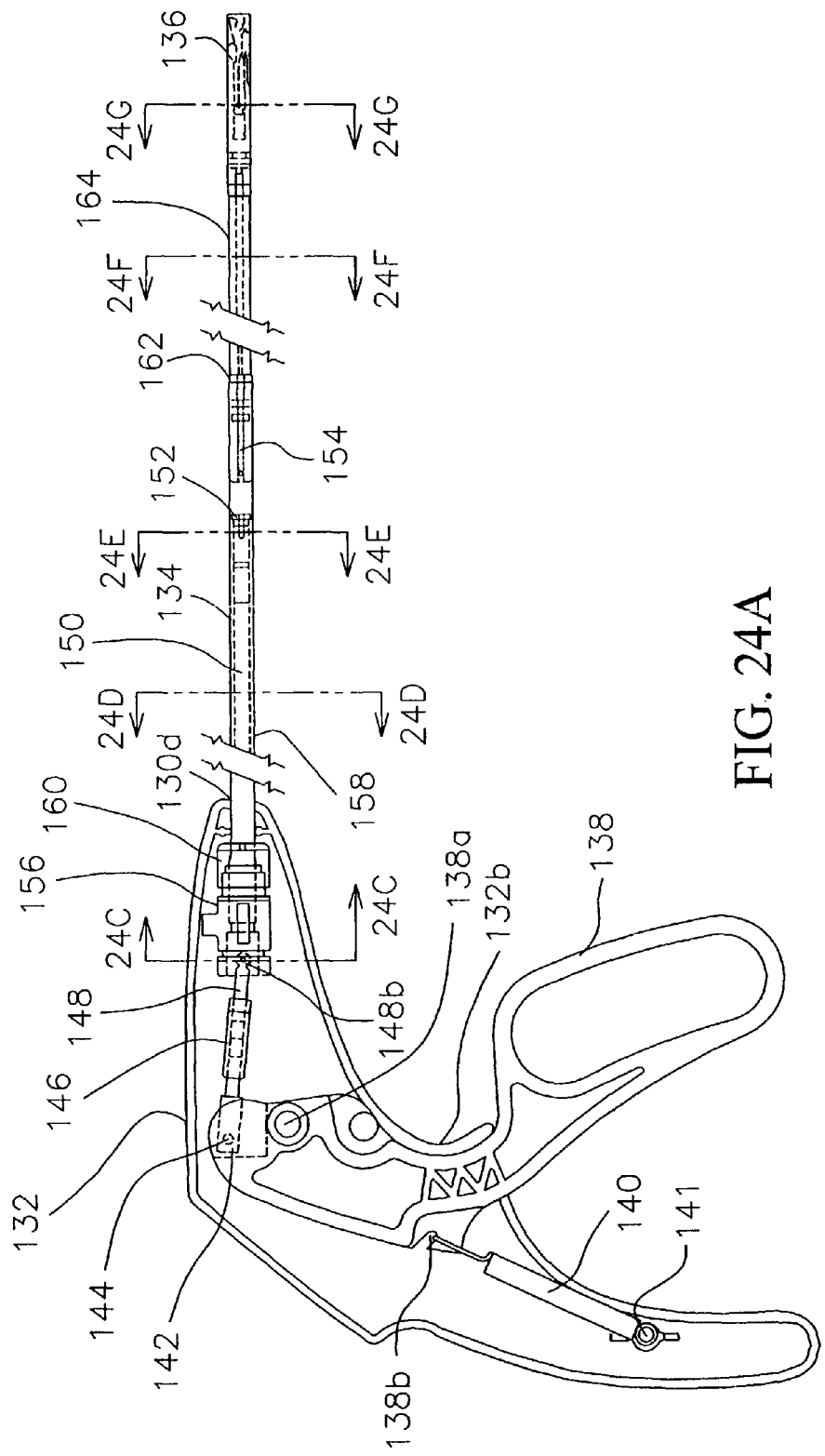
FIG. 24A is a side view of the suture securing instrument of FIG. 24 in which the right cover of the housing of the instrument is removed.

Referring to FIGS. 24, 24A, and 24B, the suture securing instrument 130 of the system is shown having a housing 132 similar to housing 30 of suturing instrument 16. Suture securing instrument 130 represents the Ti-KNOT® TK•5™ manufactured by LSI Solutions, Inc. (formally LaserSurge, Inc.) of Rochester, N.Y., except that its shaft 134 is longer and partially flexible, and means are provided for calibrating the length of a drive wire to the distal end 136 of the instrument 130. The distal end of instrument 130 may be similar to that described in U.S. Pat. Nos. 5,669,917, 5,643,289, 5,520,702, or European Patent Application No. 95102587.3, filed Feb. 23, 1995 and published Feb. 2, 1994 under Publication No. 0669103A1, which are herein incorporated by reference. The suture securing instrument 130 includes an actuator member 138 representing a lever having two pins 138*a* extending into holes in the sides of housing 132 upon which the actuator member is pivotally mounted in the housing. Actuator member 138 has a portion which extends through an opening 132*a* in housing 132 to enable pivotal movement about pin 138*a*. A extension spring 140 is provided which hooks at one end in a notch 138*b* of actuator member 138 and is wound at the other end around a pin 141 located in holes in the sides of housing 132, such that the actuator member 138 is spring biased to retain actuator member 138 normally in a forward position, as shown for example in FIG. 24A. The body of housing 132 has a front portion 132b providing a stop that limits the pivotal movement of the actuator member 138. A pivot barrel 142 is coupled by a pin 144 which extends through an opening 142a through the pivot barrel and two holes 143 between flanges 144 of actuator member 138. A turnbuckle 146 is provided representing a tubular member which has an interior surface right-hand threaded from one end and left-hand threaded from the other end. The turnbuckle 146 is attached to a threaded circular end 142b of pivot barrel 142 and then to the threaded circular end 148a of a ball connector 148. The ball connector has a ball 148b having a hole 148c there through. Drive tube 150 has one end 150a into which ball 148b is received and then coupled to the tube, via a pin 149, which extend through hole 148c of the ball 148b and two holes 150c in drive tube 150. An adapter 152 is received in the other end 150b of the driver tube 150 and has a hole partially extending there through in which is received and attached a drive wire 154. The adapter 152 is mounted in driver tube 150 for rotational movement about an annular groove 152a of the adapter 152. Multiple detents (not shown) are formed in the tube 150, such as by deforming the metal by pressure, over the annular groove 152a. The detents extend into the annular groove 152a to form a track guide within which the adapter 152 may be rotated.

Another adapter 156 is provided which has flanges 156a received in the two sides of housing 132. A rigid tube 158 having an end 158a which is D-shaped is registered into a corresponding shaped opening in adapter 156, and a threaded nut 160 having an opening which extends over mounting tube 158 and screws onto the end of the adapter 156 to secure tube 158 to adapter 156. Rigid tube 158 extends from housing 132 via an opening 130d in the housing. The assembly of components 142, 146, 148, 150, 152, and 154 described above are received in the adapter 156 and through rigid tube 158, as shown in FIG. 24A. A cross-section of the adapter 156 and rigid tube 158 at pin 149 is shown in FIG. 24C. Cross-section of shaft 134 through the rigid tube 158 at the drive tube is shown in FIG. 24D, and at the adapter 152 in FIG. 24E. The drive tube 150 is moveable through rigid tube 158. At the other end 158b of the rigid tube 158 is another adapter 162 which is cylindrical and has a central hole 162a extending there through. The adapter 162 is mounted in tube 158 by mechanical fastening in which small dents in the metal of the tip tube formed with a press into two slots 162b on either side of the adapter 162. The drive wire 154 extends through hole 162a of the adapter 162 and into an extension tube 164 which extends from the adapter 162 to the distal end 136 of instrument 130. Extension tube 164 is a stainless steel tube having for example, an inner diameter of 0.041 inches and an outer diameter of 0.059 inches, and is mounted in hole 162a of adapter 162, such as by welding or brazing, while enabling movement of the drive wire through adapter 162 and extension tube 164. Drive wire 154 may be, for example, stainless steel music wire. A cross-section of shaft 134b through extension tube 164 is shown in FIG. 24F. Pivot barrel 142, turnbuckle 146, ball connector 148, drive tube 150, adapter 152, rigid tube 158, and adapter 162 may be made of metal, such as stainless steel, while adapter 156 may be made of molded plastic.

Figure 25:
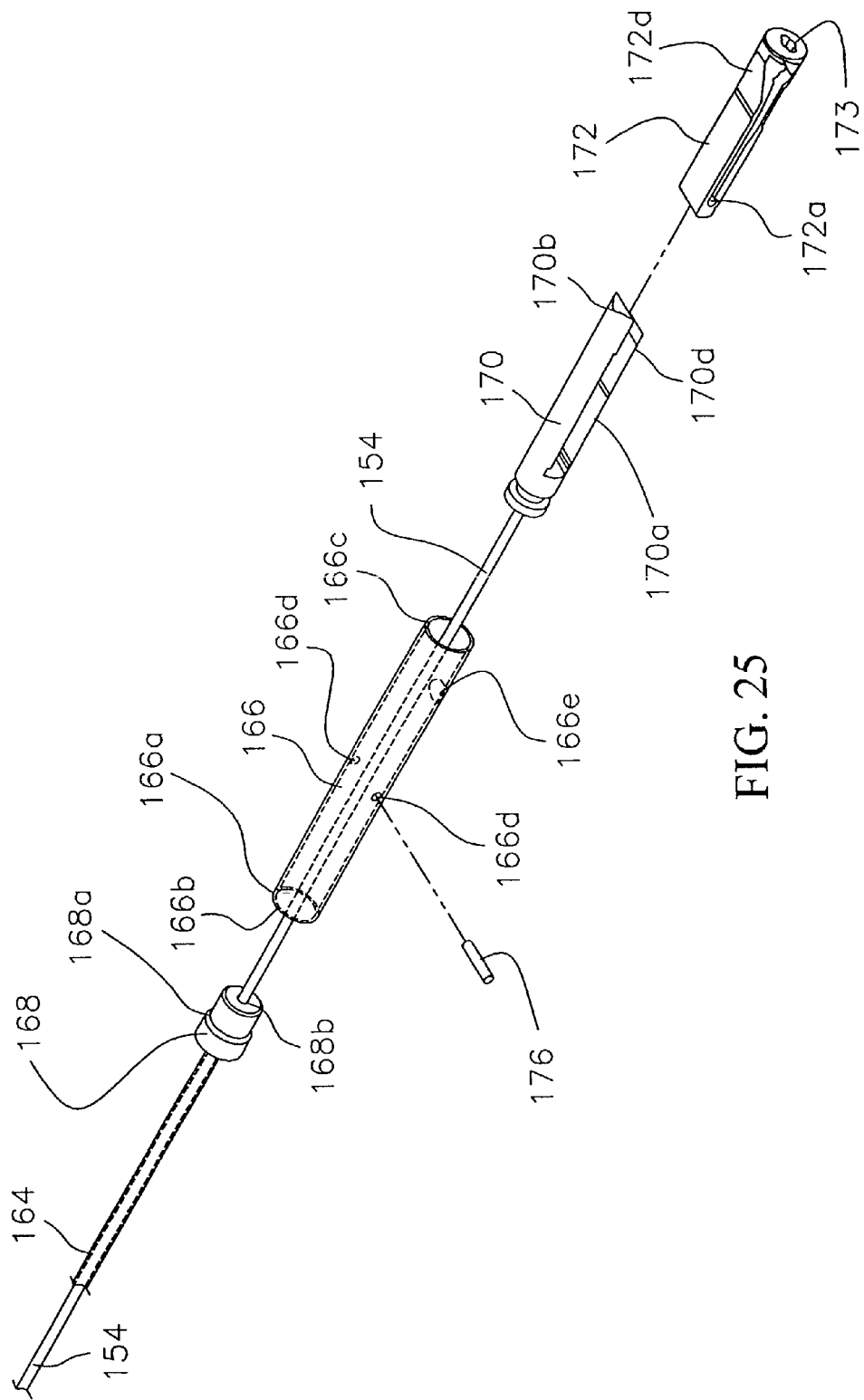
FIG. 25 is exploded view of the distal end of the suture securing instrument of FIG. 24.
Figure 25A:
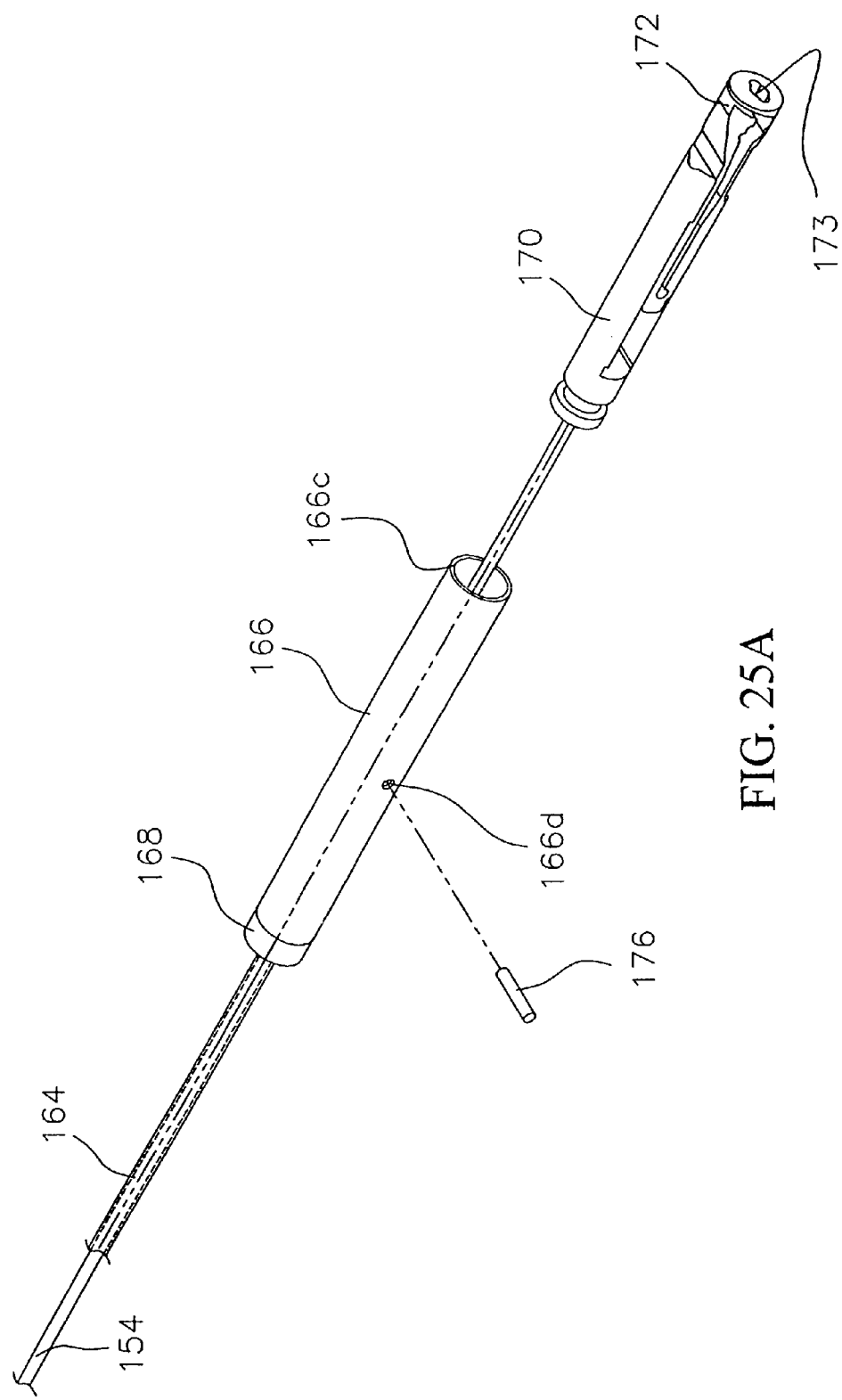

The assembly of the distal end 136 is best shown in FIGS. 25, 25A, and 25B. A tip tube 166 is provided having an end 166a into which is inserted a couple member 168 having an edge 168a which mates along the edge 166b of tip tube 166. The end 164a of extension tube 164 is received into a central hole 168b through coupler member 168 in which the drive wire 154 extends through the coupler member 168 and is received and attached in opening 171 (FIG. 25C) in a wedge tip section 170, where it is attached thereto, such as by Welding or brazing. The wedge tip section 170 has a slot 170a partially there through into which is received the hammer and anvil section 172, such that the hammer and anvil section is slidable in slot 170a. Sections 170 and 172 are received in the tip tube 166. A pin 176 extends through two holes 166d and an opening 172a through hammer and anvil section 172 to retain section 172 in tube 166.

A chamber 173 is provided in the hammer and anvil section into which a securing sleeve member 174 (FIG. 25B) is located. The securing sleeve member 174 may be a Titanium Knot™ titanium tube manufactured by LSI Solutions, Inc. (formally LaserSurge, Inc.) of Rochester, N.Y. Cross-sections through the distal end 136 of the suture securing instrument are shown in FIGS. 24G and 25C. The wedge tip section has an upper member 170b and a lower member 170d having a knife 170d when wedge tip section 170 is driven forward upper member 170b abuts ramp 172d of the hamper and anvil section 172 to first push hammer 172b down to deform and crimp sleeve member 174 against anvil 172c, and then knife 170d cut sutures extending from sleeve member 174 near opening 166e of tip tube 166. Thus, with ends of suture extending through the sleeve member 174 and exit the opening 166e of the tube tip 166, wedge tip section 170 and the hammer and anvil section 172 provides for crimping the sleeve member to retain the suture and then cuts the suture in response to forward movement of the drive tube 150 and drive wire 154. Drive tube 150 and drive wire 154 are moved forward by an operator pulling actuator member 138 towards handle 132c of housing 132, as will be described in more detail in connection with FIGS. 27A-H. Rotation of adapter 152 in tube 150 facilitates freedom of wedge tip 170 to translate, or tilt, along its center axis, which extends in the direction of wire 154, as the wedge tip is driven forward against the ramped surface of hammer 172b. Rotational movement of actuator member 138 is enabled by pivoting of the pivot barrel 142 about the axis defined by pin 144 in flanges 145.

Before attachment of the distal end 136 to extension tube 164 through which drive wire 154 extends, tube 164 is passes through a flexible plastic tubing 178, such as of Tygon. This tubing 178 extends from end 158b of rigid tube 158, until distal end 136 when mounted to extension tube 164. The diameter of tubing 178 is substantially matched to the outside diameter of tube 158 and tip tube 166. A shrink wrap layer 180 is applied on the entire length of shaft 134 of instrument 130 until distal end 136.

The entire length of the instrument 130 is such that it can extend through accessory tube 12 in which its shaft 134 has a non-flexible section 134a defined by the extend of rigid tube 158, and a flexible section defined by the extent of extension tube 164 in tubing 178. For example, the shaft 134 may be 31.5 inches in length, where its non-flexible section 134a is 12.0 inches in length, and the flexible section 134b is 19.5 inches in length.

Figure 26D:
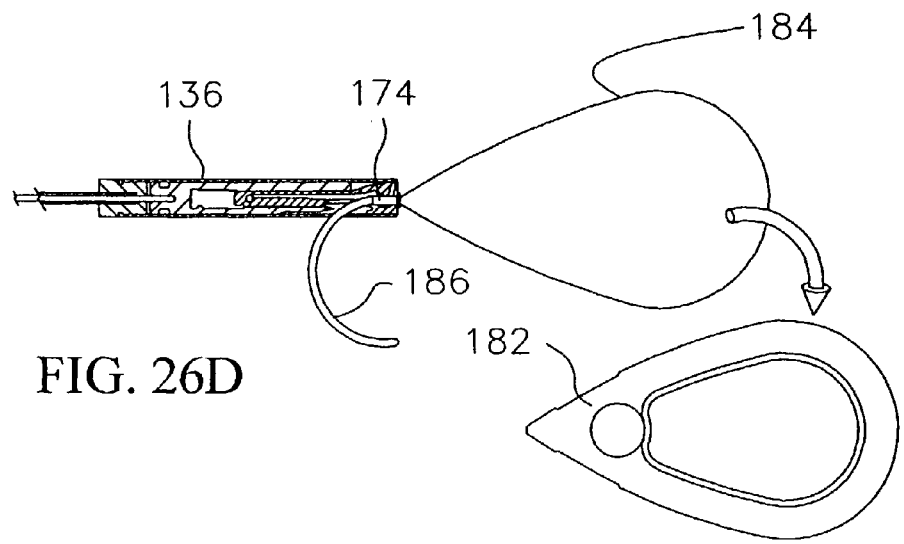
Figure 26E:
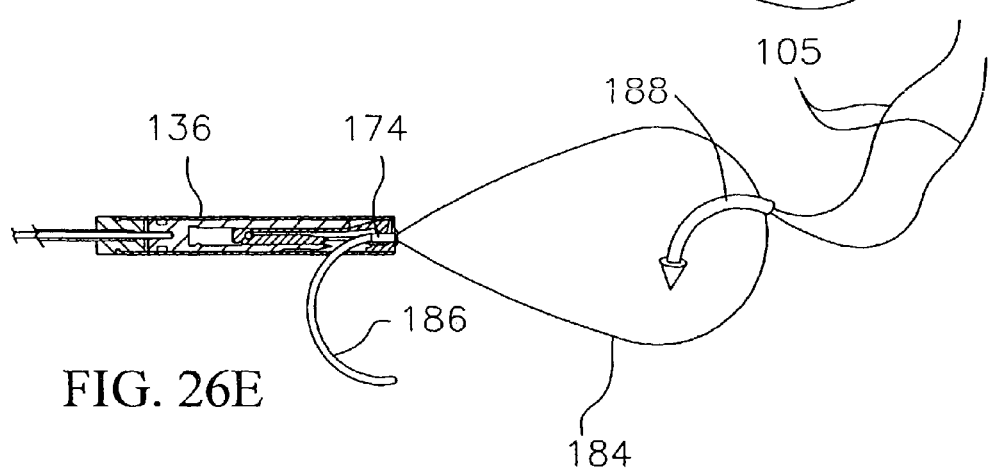
FIGS. 26E-26I illustrate use of the guide wire loop of FIG. 26D to load the suture through the sleeve member at the distal end of the suture securing instrument of FIG. 24.
Figure 26F:
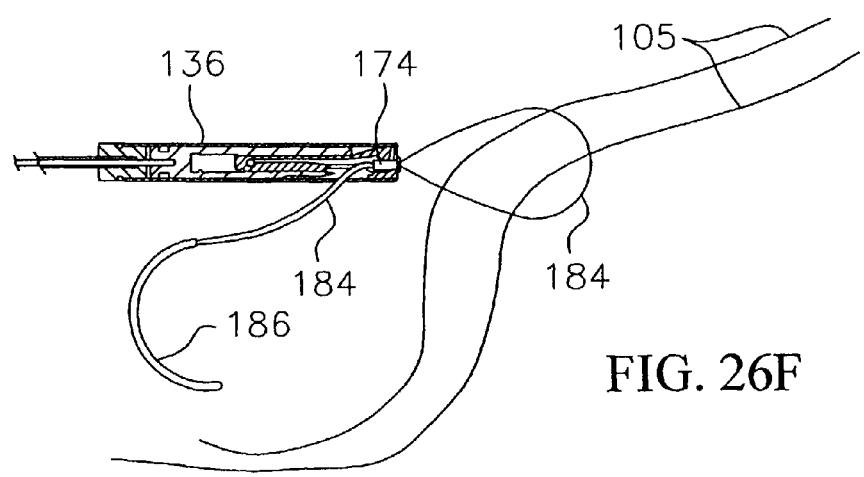

Referring to FIGS. 26A-26D, the loading of sleeve member 174 into the distal end 136 of the suture securing instrument 130 is shown using a flexible holder 182 having a outer groove (not shown) around which a wire 184 is passed to forming a loop. This loading holder is commercially available as a Ti-KNOT® TK•5™ Quick Load™ unit from LSI Solutions, Inc. (formally LaserSurge, Inc.), Rochester, N.Y. Holder 182 may be made of molded rubber, and having an opening 182a for the fingers of an operator. The ends of the wire loop 184 are attached to a C-shaped or curved handle 186, which may be composed of metal. A sleeve member 174 is slid along ring 186 until reaches the end of the ring at 186a (FIG. 26A). The ring 186 is then passed through chamber 173 of the distal end 136 between the hammer 172*b* and anvil 172*c* of section 172 and then exits through opening 166*e* of the tip tube 166 (FIG. 26B), until sleeve member 174 is located in chamber 173 (FIG. 26C). The flexible holder 184 may then be removed (FIG. 26D).

Figure 26G:
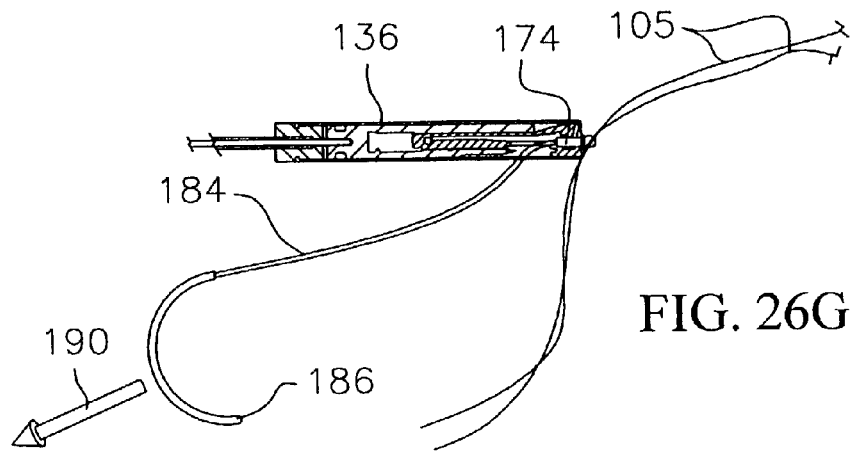
Figure 26H:
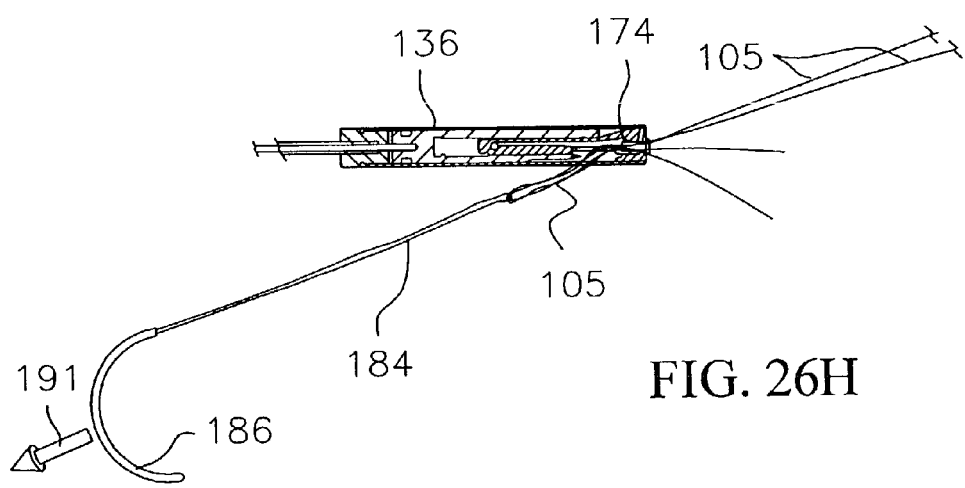
Figure 26I:
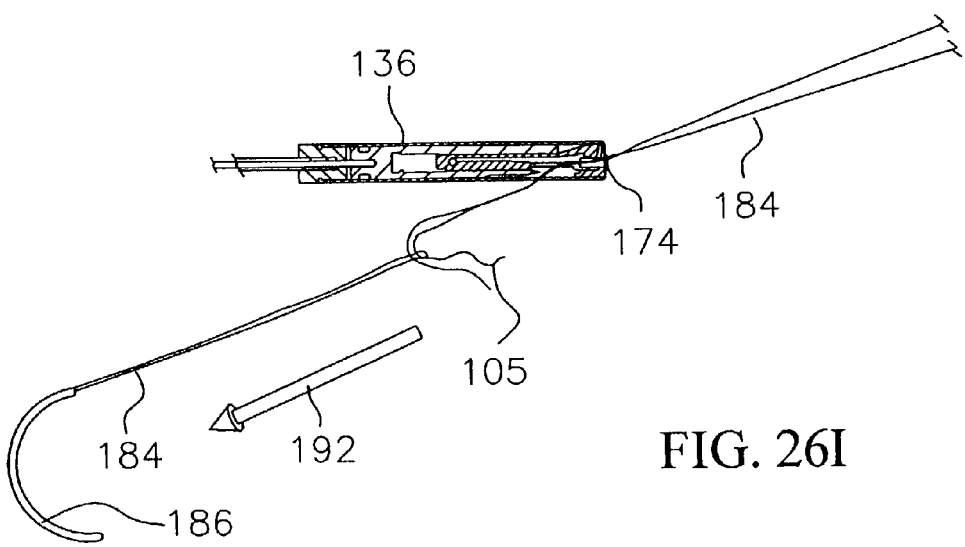

Referring to FIGS. 26E-26I, the loading of the two ends of a loop of suture 105 through a loaded sleeve member 174 in the distal end 136 of the suture securing instrument 130 is shown. The two ends of suture 105 are passed through the wire loop 184 (FIG. 26E), as shown by arrow 188, and are captured by the wire loop as the C-shaped handle 186 is used to pull the wire loop through the sleeve member 174 (FIG. 26F) and opening 166*e* of the tube tip 166, thereby pulling the two ends of the loop of suture through the sleeve member and opening 166*e* in the direction indicated by arrows 190-192 (FIGS. 26G-26I).

Figure 27A:
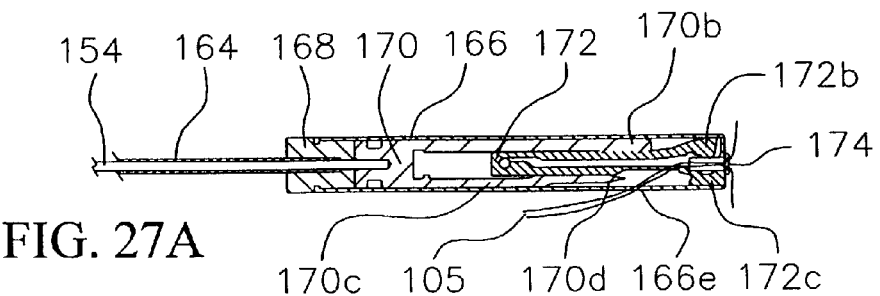
FIGS. 27A-27I illustrate at the distal end of the suture securing instrument the process of fastening a sleeve member to retain the sutured tissue closed and cutting of the suture.
Figure 27C:
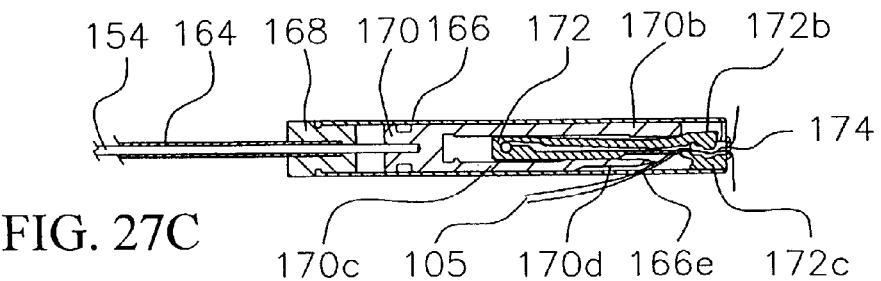
Figure 27E:
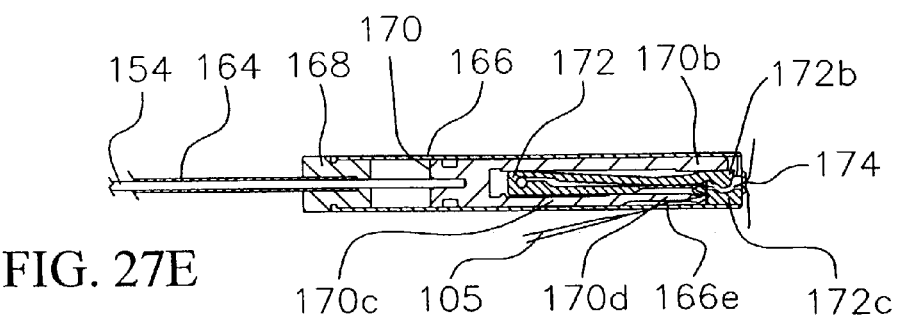
Figure 27G:
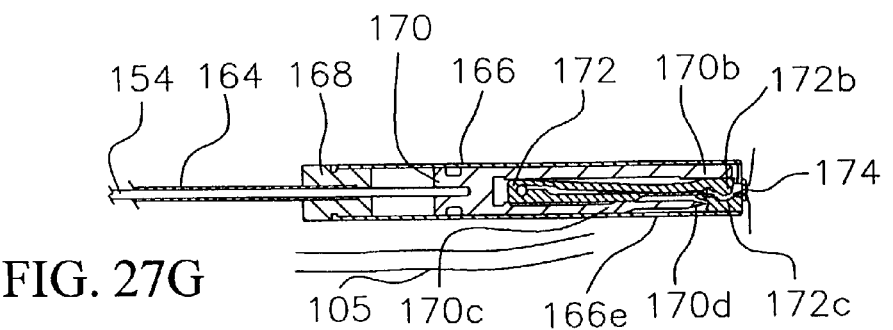
Figure 27B:
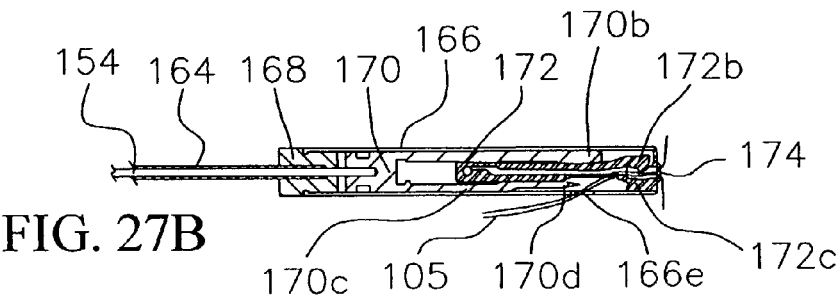
Figure 27D:
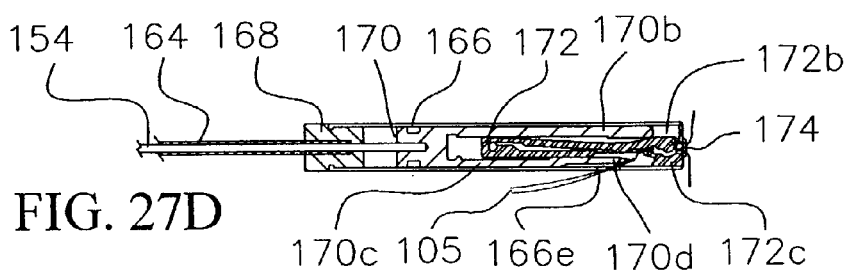
Figure 27F:
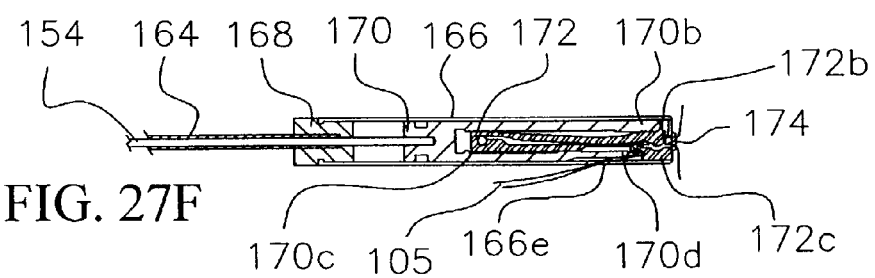
Figure 27H:
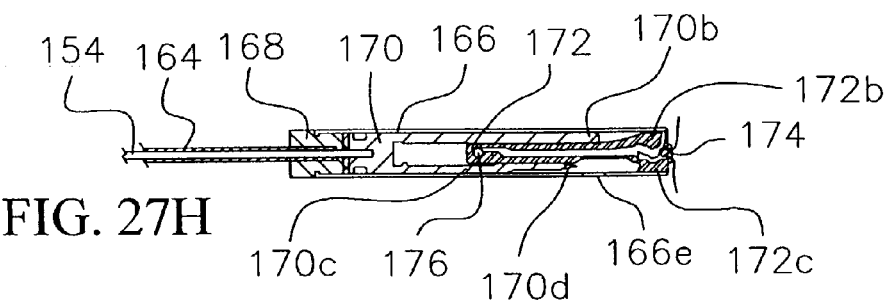
Figure 27I:
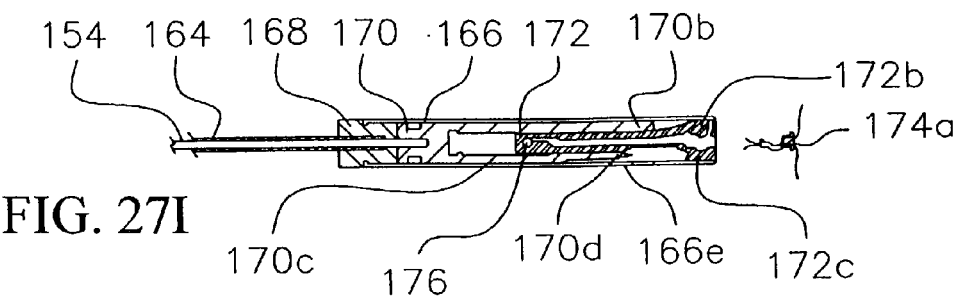

FIGS. 27A-27H shows the operation of suture securing instrument 130 to secure and cut the suture. With the ends of the loop of suture 105 extending through the sleeve member 174 at the distal end 136 of the suture securing instrument 130, the instrument may be inserted into the accessory tube 12 down to the tissue through which the suture loop extends. The ends of the suture are pulled through the distal end 136, until sleeve member 174 is located adjacent the tissue (FIG. 27A). An operator then pulls the actuator member 138 towards handle 132*c*, driving forward the wedge tip section 170 in which the motion is translated through shaft 134 via pivot barrel 142, turnbuckle 146, ball connection 148, through drive tube 150 and drive wire 154. In response, the upper member 170*b* of the wedge tip section 170 slides forward against hammer 172*b* deforming the sleeve member against anvil 170*c* to retain the suture. FIGS. 27B-27E illustrates the downwards movement of the hammer deforming on the sleeve member as the wedge tip section 170 is driven forward. The knife 170*d* at the lower member 170*c* of the wedge tip section 170 is also driven forward against the suture (FIG. 27F), to cut the ends of the suture near the sleeve member 174 (FIG. 27G). The operator then releases the actuator member 138 which automatically retracts in response to the forward bias by spring 140, and the wedge tip section 170 retracts releasing the sleeve member 174 from between hammer 172*b* and anvil 172*c* (FIG. 27H). The distal end 136 of suture instrument 130 is then removed leaving the crimped sleeve member 174*a* to retain the sutured tissue closed (FIG. 27I).

Figure 79:
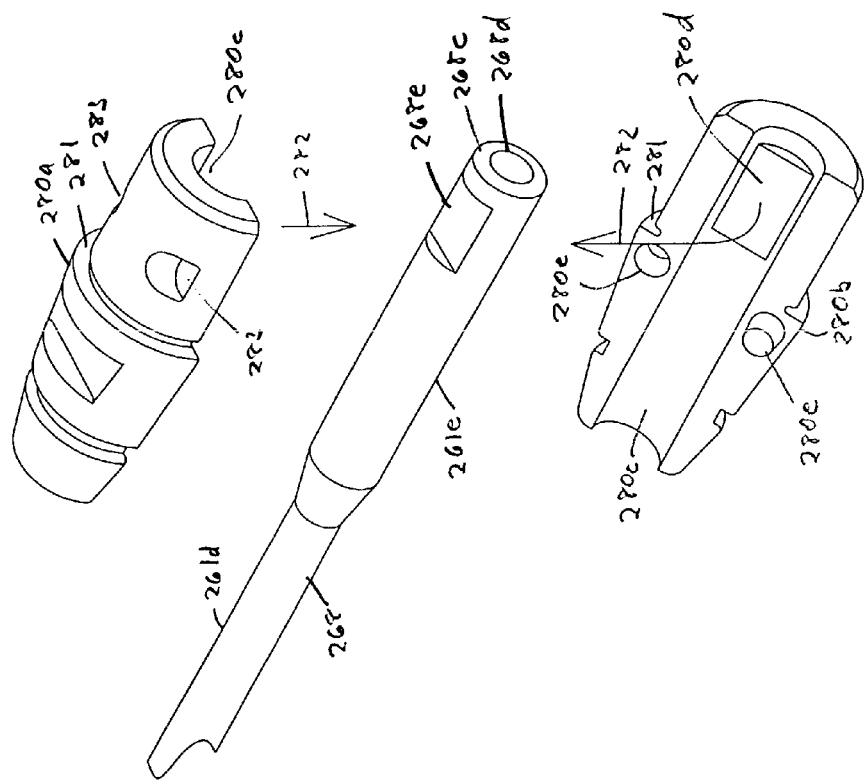
Figure 80:
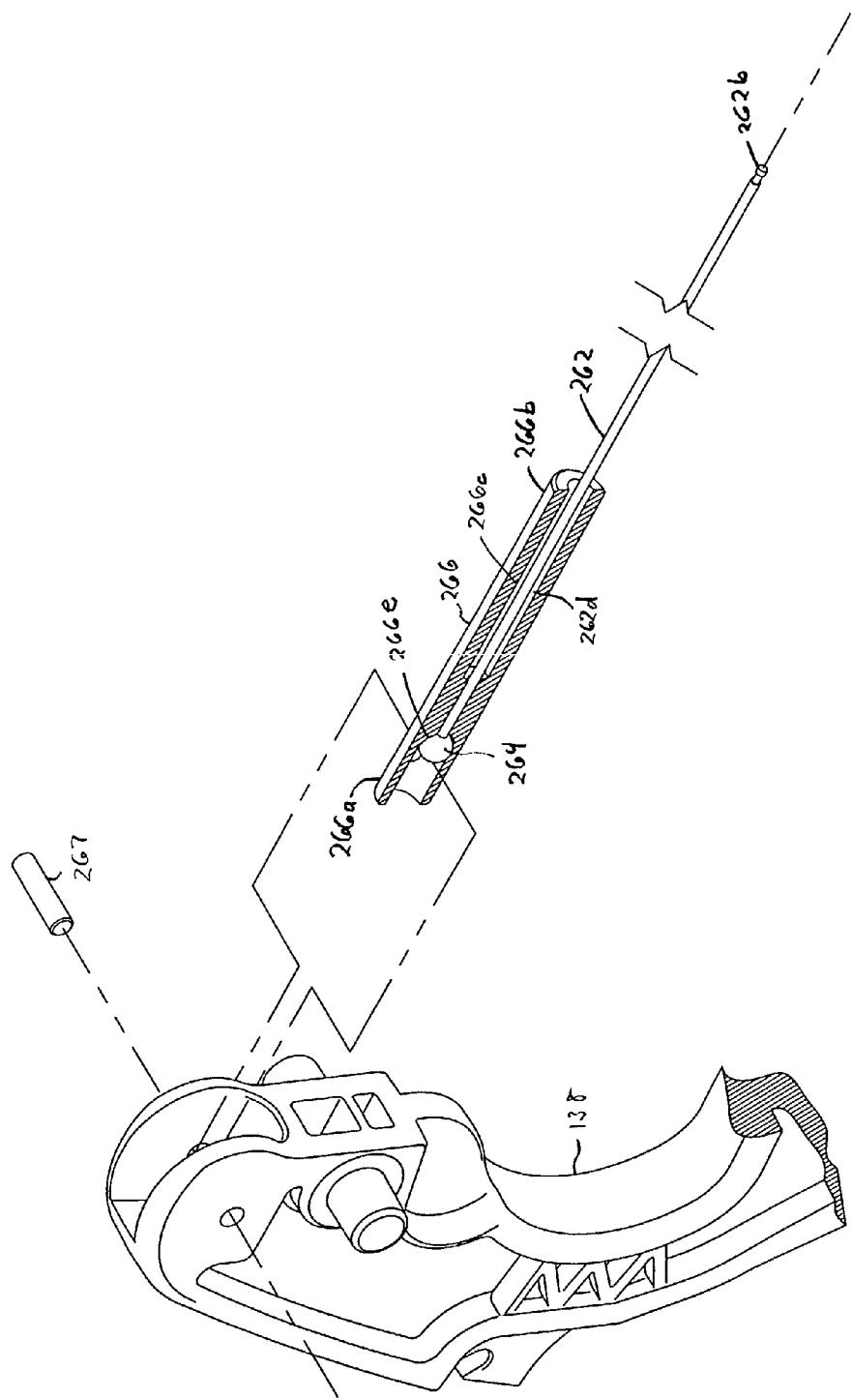

Referring to FIGS. 66, 66A, 67-82, and 82A, another embodiment of the suture securing instrument in system 10. In this embodiment, suture securing instrument 260, the housing 132, actuator member 138 and the component 166, 170, and 172 of distal end 260*a* are the same as suture securing instrument 130, and such components have identical reference numerals. The number of components has been reduced for mounting and driving wedge tip section 170 via a drive wire through shaft 260*b* of the instrument, and to provide flexibility along the entire shaft exiting housing 132. To attach a drive wire 262 to the actuator member 138, wire 262 is first attached, e.g., welded, at its end 262*a*, to a hole in hall 264, which is received as a socket 266*e* inside one end 266*a* of an adapter barrel 266, such that the wire extends through opening 266*c* to end 266*b* of the barrel, as best shown in FIG. 80. A pin 267 is received through hold 266*e* extending through barrel 266, and holes 143 of actuator member 138. Opening 266*c* after socket 266*e* expands to define a circular cross-section cavity 262*d* of a diameter into which one end 268*a* of a flexible tube 268 can be received and is slidable therein as actuator member 138 pivots forward or backwards.

Figure 69:
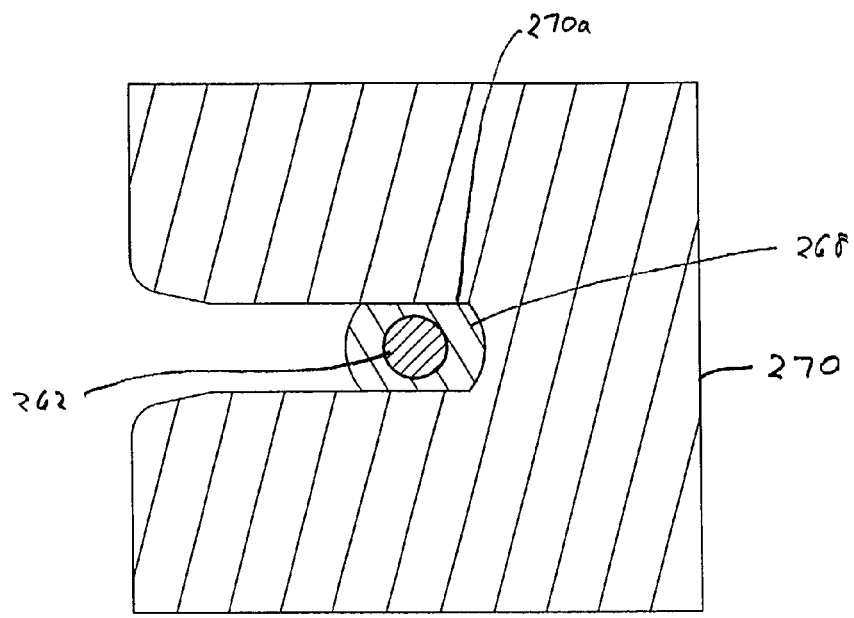
FIG. 69 is cross-sectional view along lines 69-69 of FIG. 68.
Figure 70:
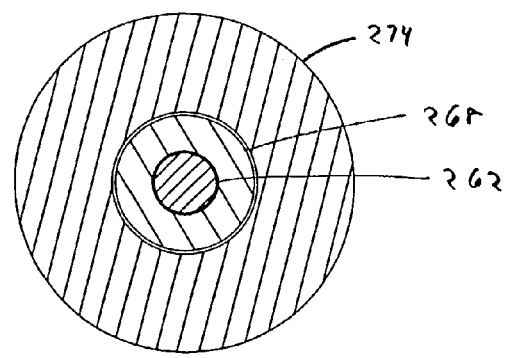
FIG. 70 is cross-sectional view along lines 70-70 of FIG. 68.
Figure 71:
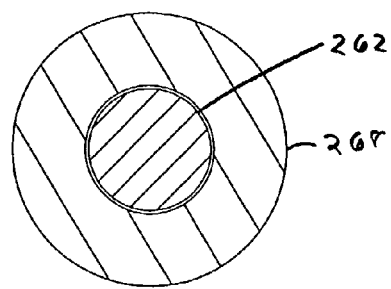
FIG. 71 is cross-sectional view along lines 71-71 of FIG. 68.
Figure 72:
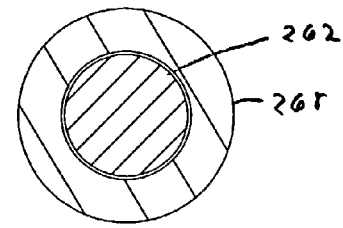
Figure 73:
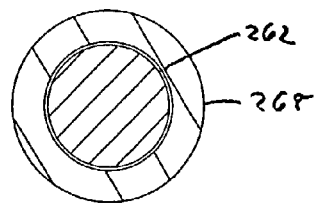
Figure 74:
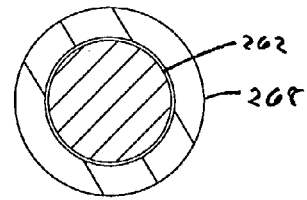
Figure 75:
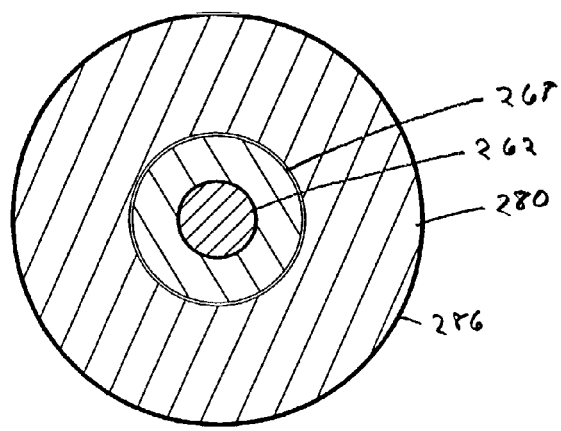
Figure 76:
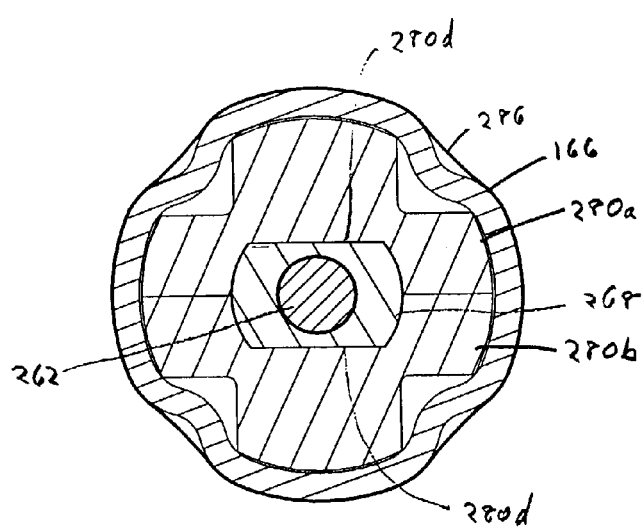
Figure 77:
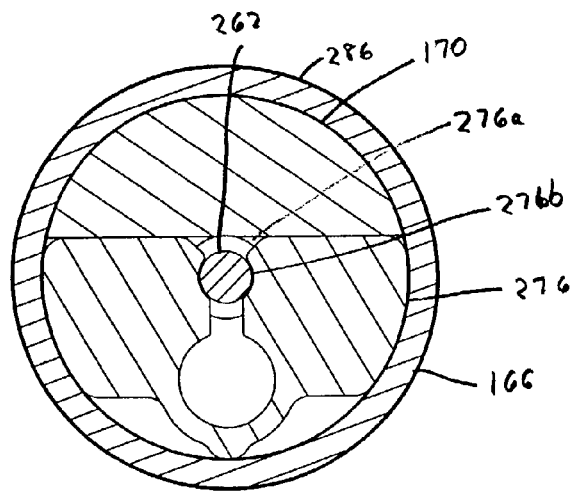
Figure 78:
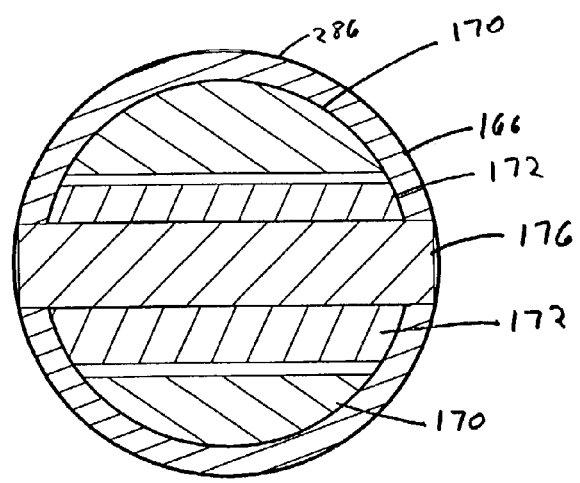

The wire 262 is movable within the flexible tube 268. The flexible tube 268 is mounted in one of the halves of housing 132 by a clip 270 having a slot 270*a* which engages two undercut regions 268*b* on the top and bottom, respectively, of the flexible tube. The clip 270 is then mounted in a recess 272 of housing 132 to lock the flexible tube 268 to housing 132. A partially flexible cylindrical overtube body 274 is then provided having its end 274*a* abutting clip 270 in housing 132 and extends out hole 130*d* of housing 132. The flexible tube 268 extends through the overtube body 274, which tapers to an opening 274*b*. A cross-section through clip 270 is shown in FIG. 69, and through the overtube body 274 and flexible tube 268 in FIG. 70. For example, flexible tube 268 and adapter barrel 266 may be of stainless steel or other biocompatible material, and overtube body 274 of molded plastic such as extrusion of pebax.

Figure 66:
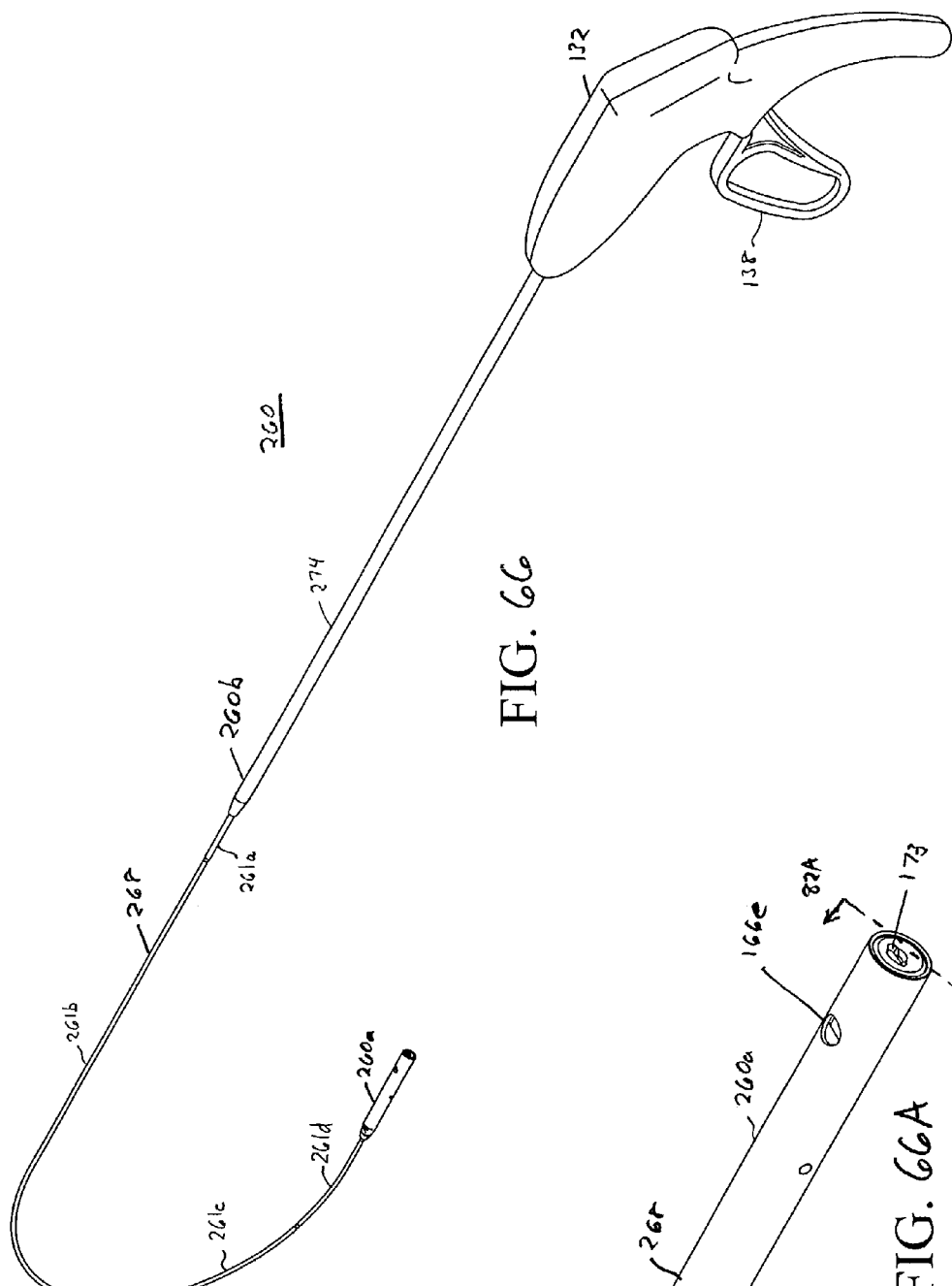
FIG. 66 is a perspective view of another embodiment of the suture securing instrument in the system of the present invention.
Figure 66A:
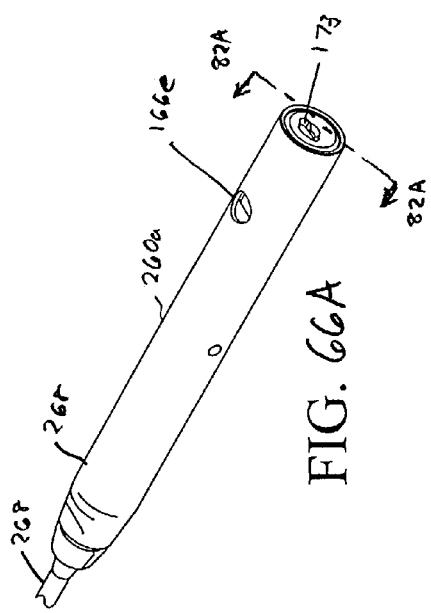
FIG. 66A is an expanded view of the distal end of the suture securing instrument of FIG. 66.
Figure 67:
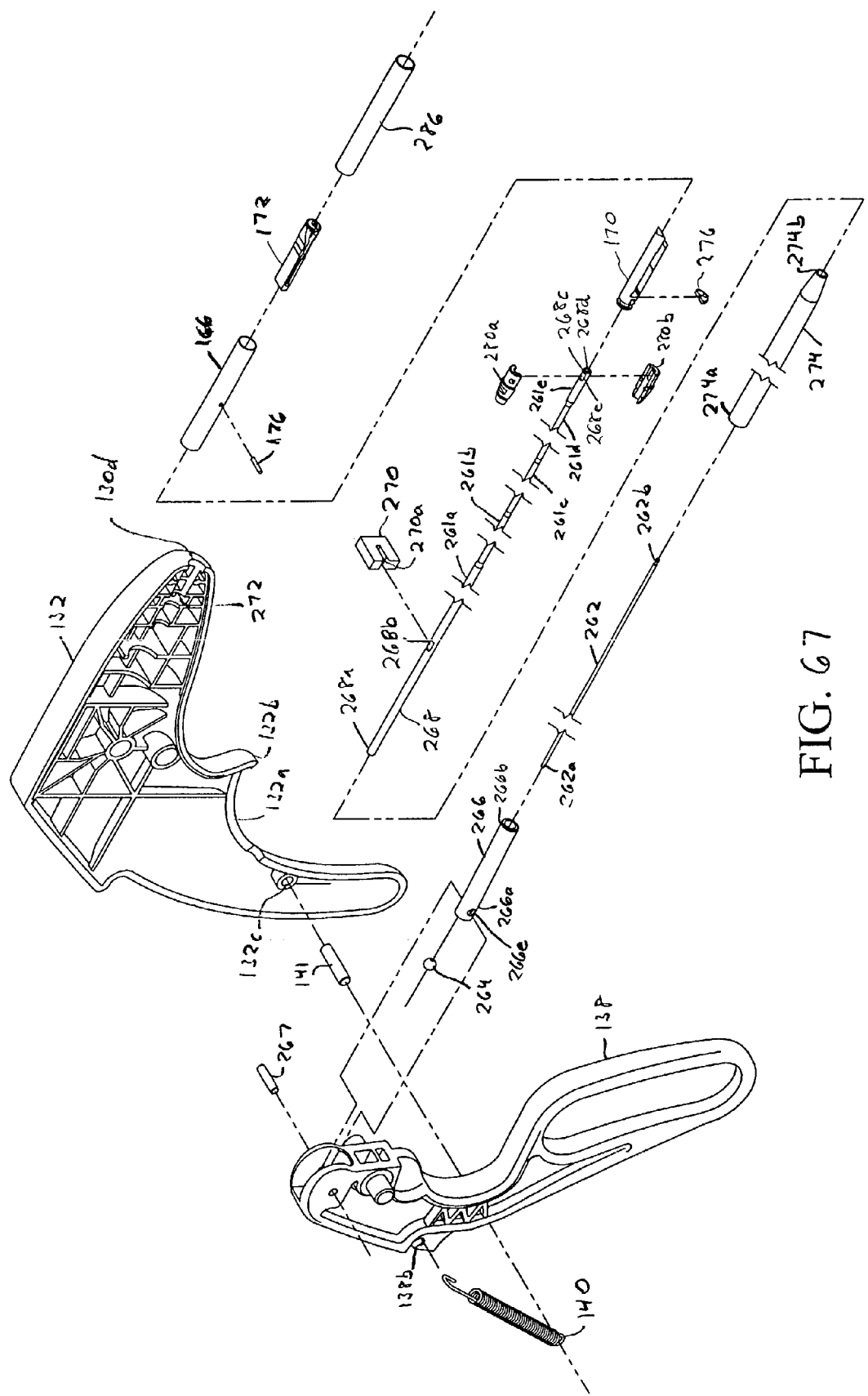
FIG. 67 is an exploded view of the suture securing instrument of FIG. 66 in which the right cover of the housing is removed.
Figure 68:
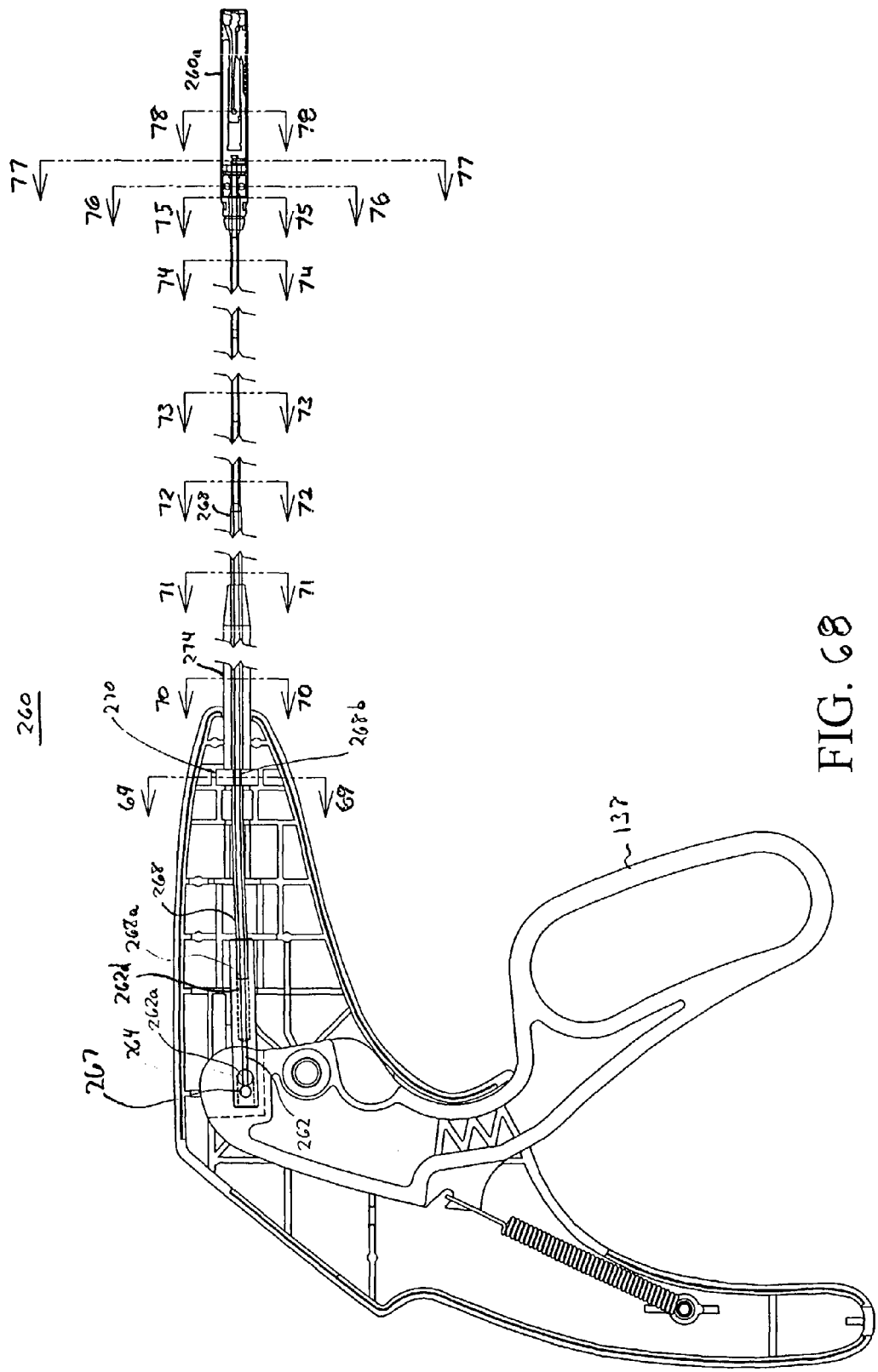
FIG. 68 is a side view of the suture securing instrument of FIG. 66 in which the right cover of the housing of the instrument is removed.

The flexible tube 268 after exiting overtube body 274 has a first diameter section 261*a* from its end 268*a*, and second smaller diameter sections 261*b*, 261*c*, and 261*d* each of a smaller diameter until end 268*c*. End 268*c* is part of a section 261*e* that may have the same diameter as the first section 261*a*. Preferably, flexible tube 268 is of a single tube grinded to provide sections 261*b-e* of desired diameters to enhance flexibility of shaft 260*b*. However, multiple segments may be coupled to each other to provide the flexible tube 268. For example, the inner diameter of the opening extending through flexible tube 268 may be 0.039 inches, the outer diameter of sections 261*a*, 261*b*, 261*c*, and 261*d* may be 0.083, 0.065, 0.058, and 0.057 inches, respectively, the outer diameter of overtube body 274 may be 0.307 inches, and the diameter of the wire 262 may be 0.037 inches. The length of shaft 260*b* provided by the overtube body 274 and flexible tube 268 may be the same as shaft 134 of instrument 130 described earlier. As shown in FIG. 66, flexible tube 268 at least along sections 261*b-d* provides part of the shaft 260*b* which is substantially bendable along its length. Cross-sections through the shaft are shown in FIGS. 71-74.

Figure 81:
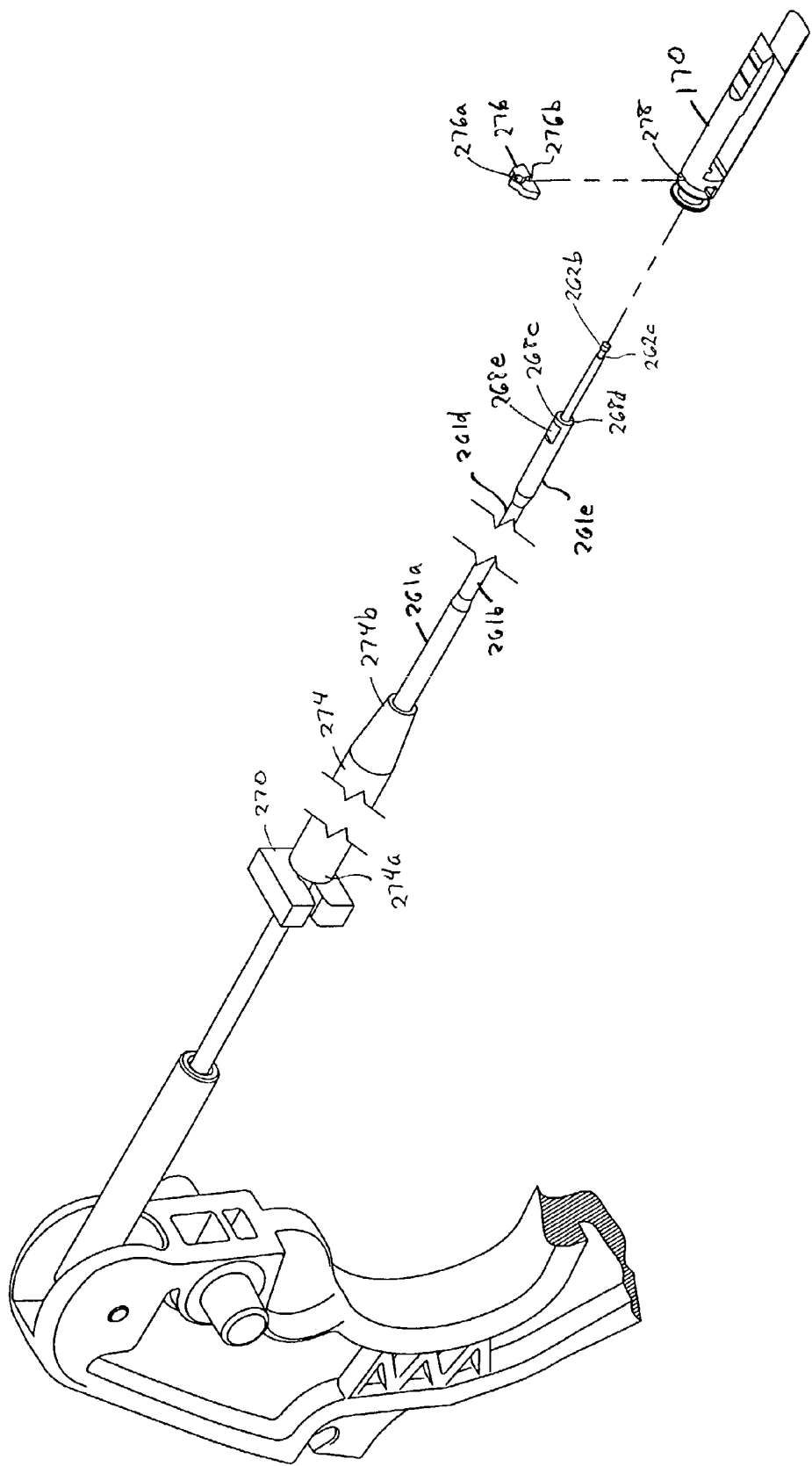

The wire 262 exits opening 268*d* of flexible tube 268 and the end 262*b* of the wire is inserted in hole 284 extending in the wedge tip section 170. Once inserted, the wire is captured in an opening 276*a* through a slot 276*b* of clip 276 which engages undercut annular region 262*c* of wire 262 as clip 276 is inserted in slot 278 provided in wedge tip section 170, thereby locking the wire to the wedge tip section, as best shown in FIG. 81.

Two identical halves 280*a* and 280*b* of distal coupler 280 capture the end 268*c* of flexible tube 268 along two undercut regions 268*e* on the top and bottom, respectively, of the tube 268. Distal coupler 280 has an opening 280*c* extending there through have two opposing surfaces 280*d* therein, one from each half 280*a* and 280*b*, which engage undercut regions 268*e* of flexible tube 268, to capture the flexible tube. The attachment of the distal coupler halves 280*a* and 280*b* to the flexible tube is best shown in FIG. 79 and is indicated by arrow 282. Features such as prong and holes 280*e* may be provided to enable the halves 280*a* and 280*b* to snap fit together. The distal coupler 280 once assembled is received in tip tube 166 up until annular ledge 281 (FIG. 82A), and is then attached to the tip tube 166, such as by staking or crimp the tip tube to deform into grooves 283 along the distal coupler. For example, four grooves may be provided, two on the exterior surface of each half 280*a* and 280*b*. A shrink wrap layer or tube 286 is applied over the tip tube 166 in which an opening is made through tube 286 to access suture hole 166*e*. Cross-sections through the distal end 260*a* of the instrument 260 are shown in FIGS. 75-78. For example, the outer diameter of the distal end 260*a* when assembled may be 0.203 inches. Thus, the flexible tube 268 is attached to tip tube 166, and wire 262 when driven forward or backward in response to actuator member 138 moves wedge tip section 170 relative to anvil section 172 situated in tip tube 166, as described earlier in suture securing instrument 130 to crimp a ferrule about suture and to cut the free ends of the suture. The sleeve member loading and suture loading of instrument 260 is the same as described earlier for instrument 130.

Figure 29A:
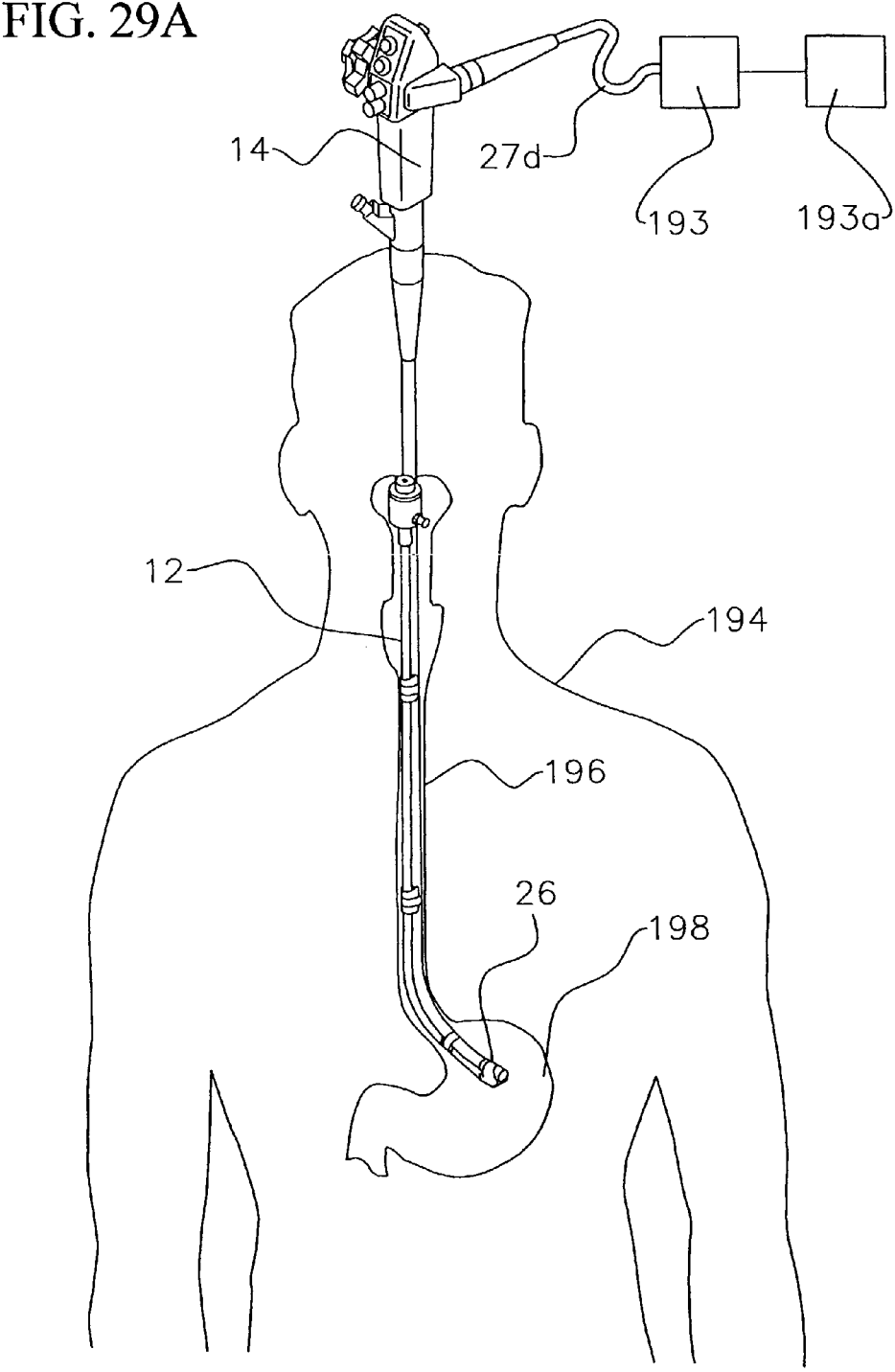
FIG. 29A is an example of the system of the present invention positioned in the gastroesophageal tract of a patient before insertion of the suturing instrument.
Figure 29B:
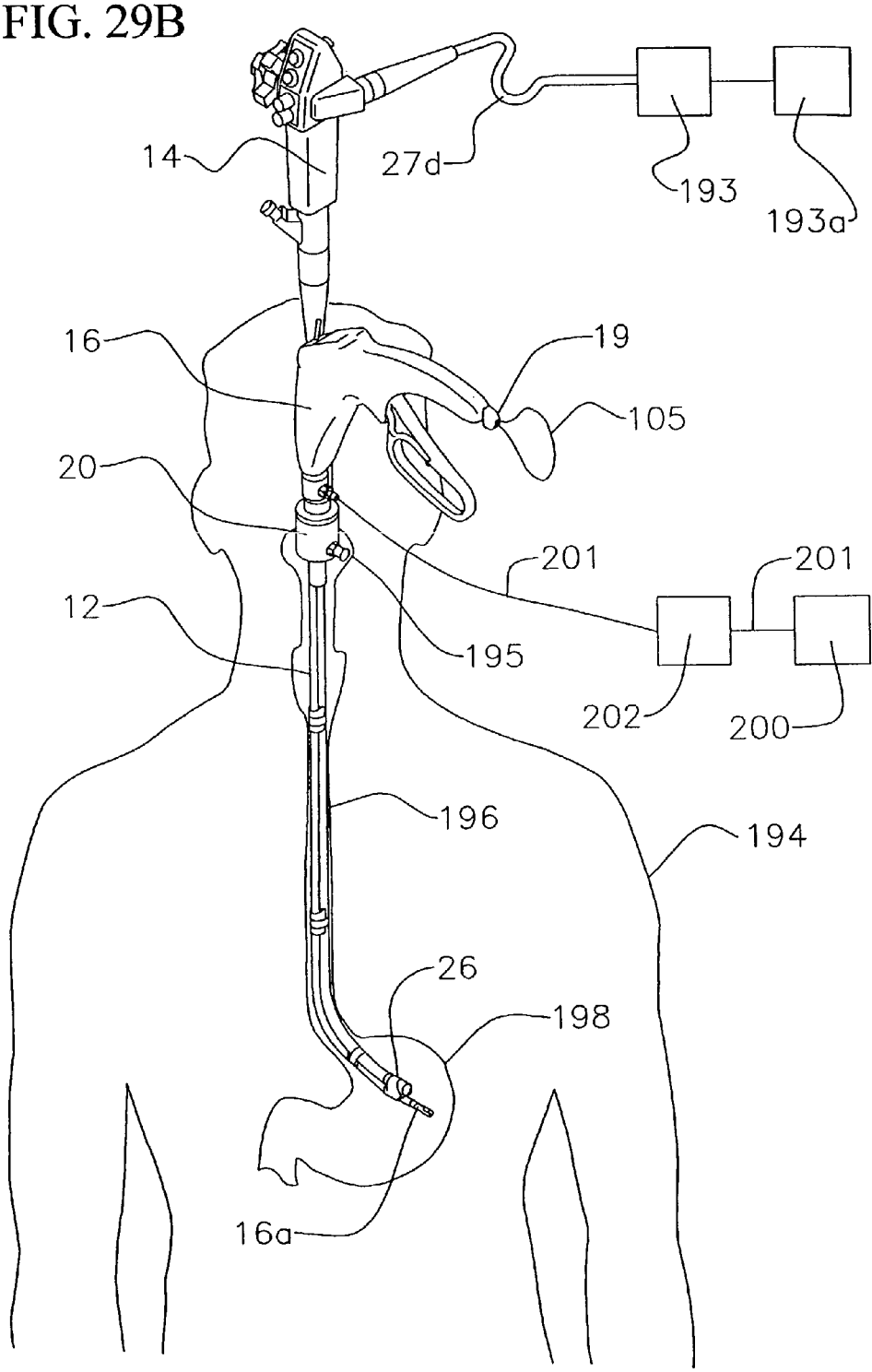
FIG. 29B is an example of the system of the present invention positioned in the gastroesophageal tract of a patient showing insertion of the suturing instrument through the accessory tube of the system.
Figure 29C:
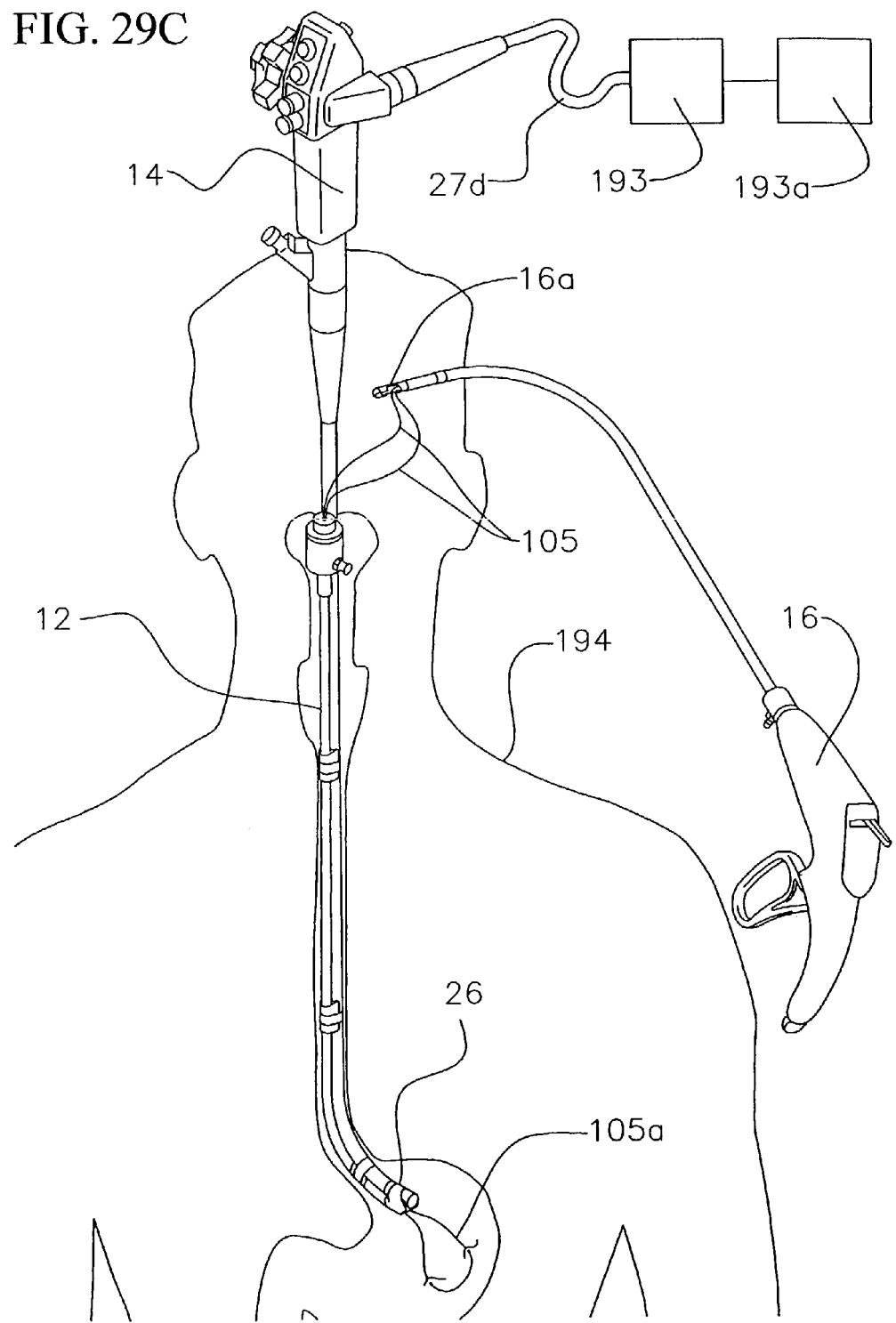
FIG. 29C is an example of the system of the present invention positioned in the gastroesophageal tract of a patient after placement of the suture thread and removal of the suturing instrument from the accessory tube of the system.
Figure 29D:
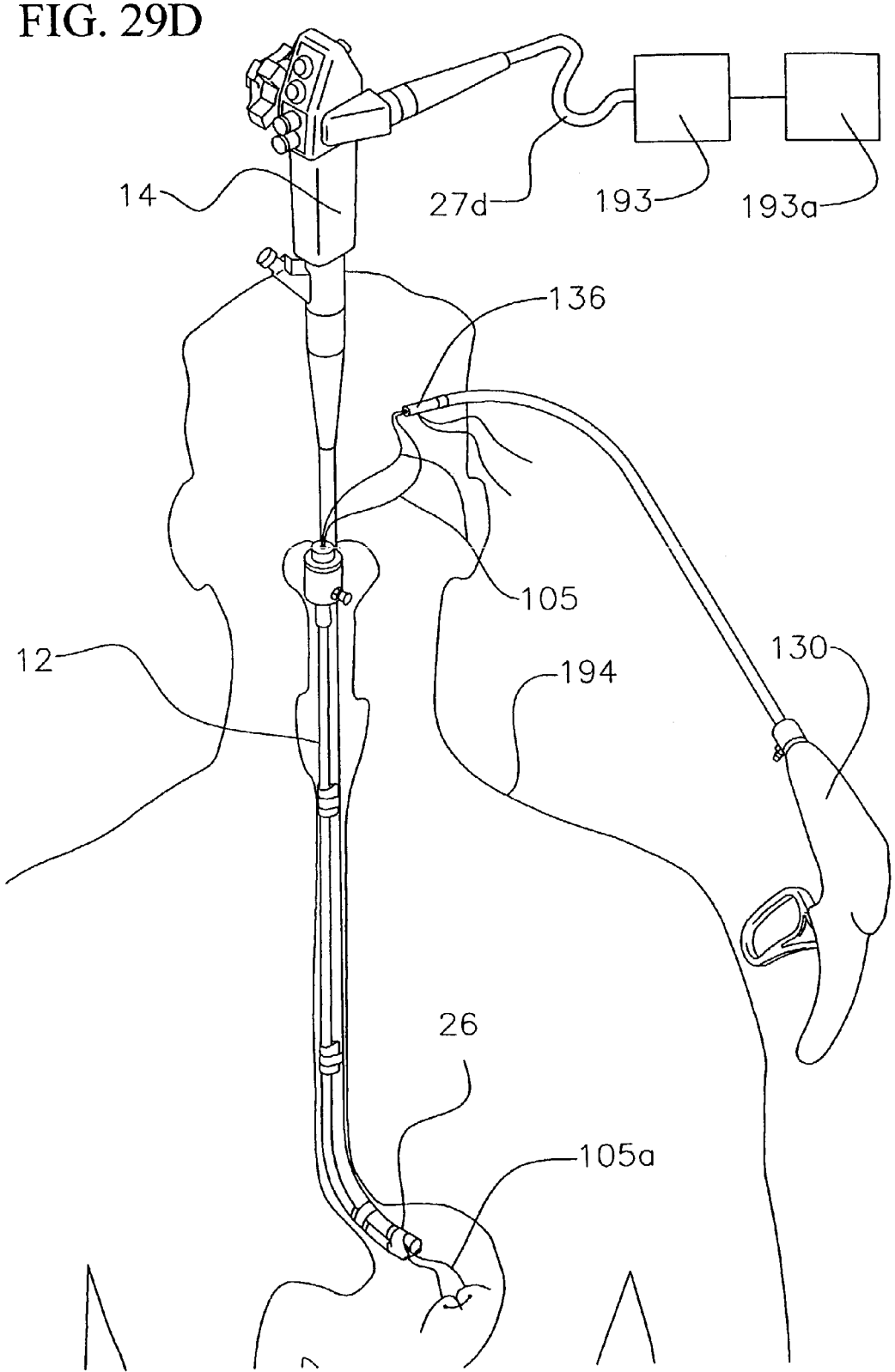
FIG. 29D is an example of the system of the present invention positioned in the gastroesophageal tract of a patient showing placement of the suture thread loop in the suture securing instrument.
Figure 29E:
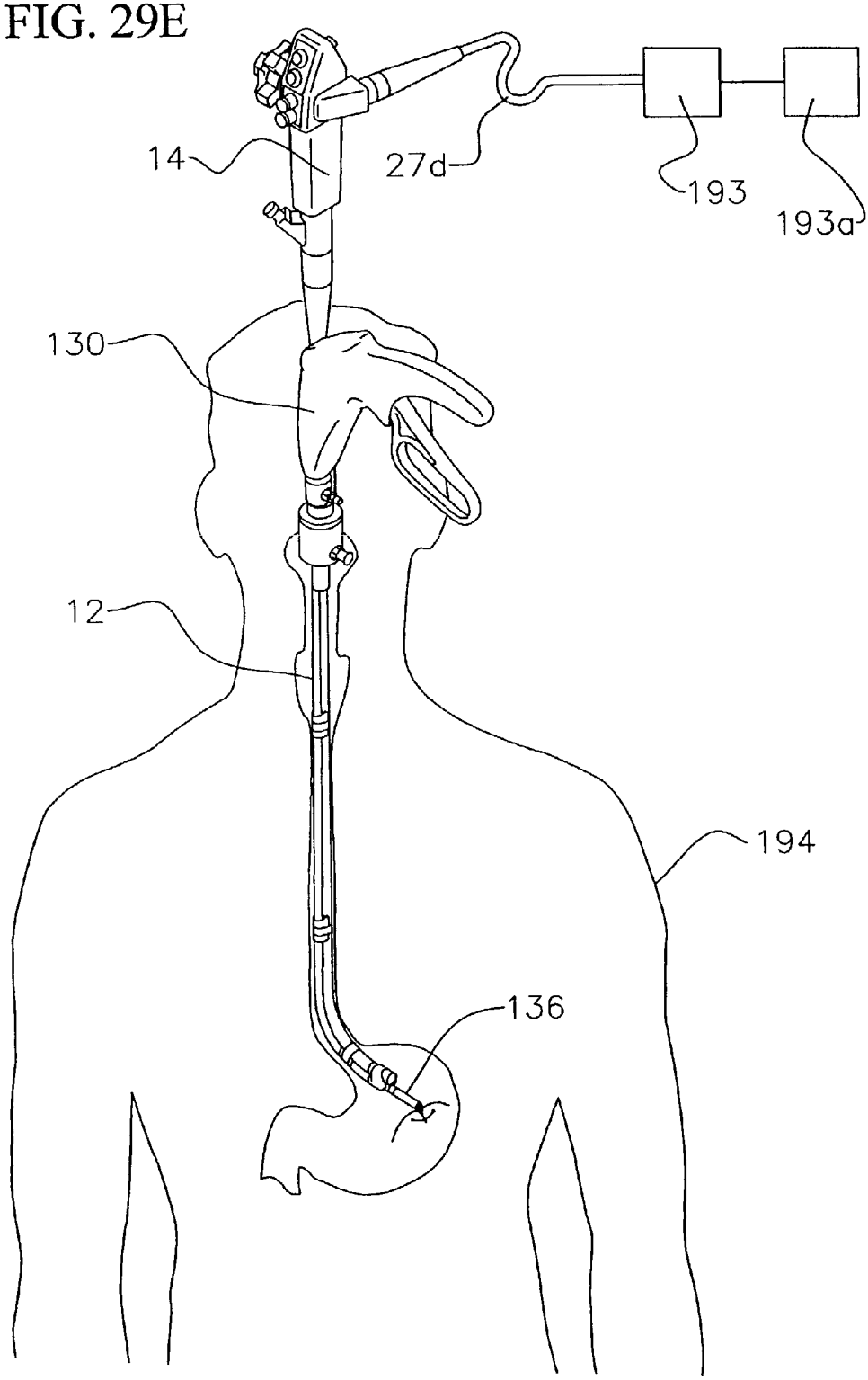
FIG. 29E is an example of the system of the present invention positioned in the gastroesophageal tract of a patient showing insertion of the suture securing instrument through the accessory tube of the system.
Figure 29F:
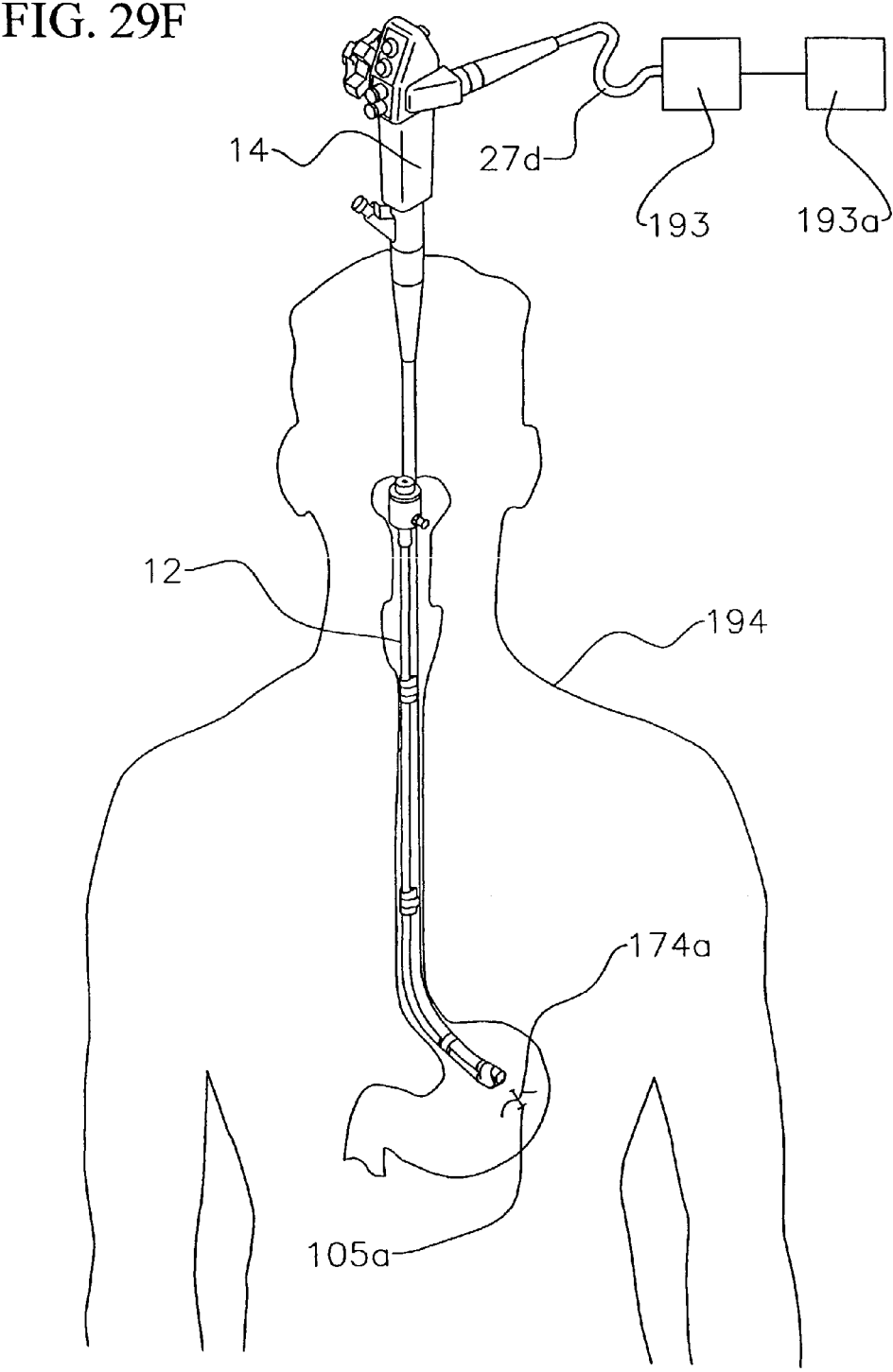
FIG. 29F is an example of the system of the present invention positioned in the gastroesophageal tract of a patient showing the secured suture remaining after removal of the suture securing instrument.
Figure 32:
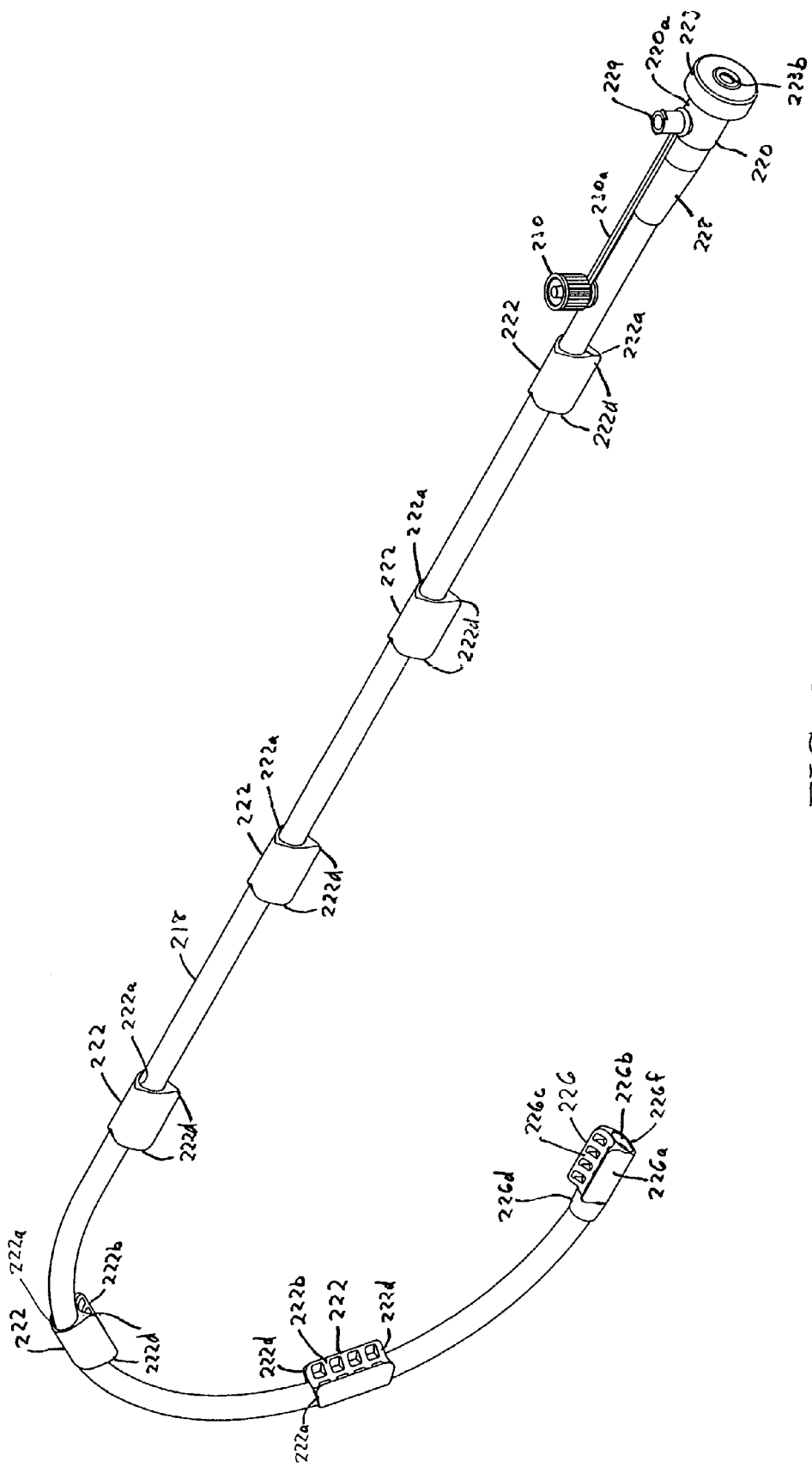
FIG. 32 is a perspective view of the accessory tube of FIG. 31 when detached from the endoscope.

Referring to FIGS. 28A-28M and 29A-29F the overall operation of system 10 will now be described in which FIGS. 28A-28M illustrate examples of the images on a display 193 provided by the gastroscope 14, and FIGS. 29A-29F illustrate the relative position of the gastroscope 14, accessory tube 12 (or 212), and instruments 16 (or 216) and 130 (or 260) during suturing and suture securing. With the patient 194 ready for the procedure, the gastroscope 14 and attached accessory tube 12 (or 212) are inserted through the mouth 195 down the esophagus 196 and into the stomach 198 where the suturing will take place (FIG. 29A). The suturing instrument 16 (or 216) with a loop of suture 105 loaded is then inserted into the accessory tube 12 via cannula 20, until the distal tissue engaging end 16a (or 216b) passes through attachment tip 26 (FIGS. 28A and 29A). The tissue engaging end 16a of the suturing instrument 16 is viewable to the operator on display 193 through the gastroscope (FIG. 28A). With the target area of the tissue located, the valve 19 is closed, and suction is applied to instrument via a vacuum source 200 and control (or regulator) 202 via tubing 201 to pull the tissue into gap 104 of sew tip 98 (or gap 248a of sew tip 248), as described earlier (FIG. 28B). Control 202 may be integrated in vacuum source 200 or along tubing 201, and is used to selectably enable and disable suction to the sew tip 98 or 248. A first one of needles 34 or 35 (234 or 235) is then extended and retracted by the operator, as described earlier, to locate the first end of the suture in the tissue. The suction is then disabled, valve 19 opened, and the sew tip is lifted leaving the suture extending through the tissue (FIGS. 28C, 28D, 28E, and 28F). The target area for the second end of the suture is then located, valve 19 closed, and vacuum again enabled to pull the tissue into the sew tip 98 (FIG. 28F). A second one of the needles 34 or 35 (234 or 235) is extended and retracted to locate the second end of the suture in the tissue. The suction is then disabled, valve 19 opened, and the sew tip lifted leaving the suture extending through the tissue. FIG. 28G shows an image of the first and second ends of the suture in the tissue. The suturing instrument 16 (or 216) is then removed from the accessory tube as shown in FIG. 29C, pulling a loop 105a of suture 105 through the stomach tissue (FIGS. 28H-28J). The ends of the suture material are cut from the suturing instrument 16 (or 216) and then loaded through the suture securing instrument 130 (or 260) which has been loaded with a sleeve member 174, as shown in FIG. 29D. The suture securing instrument 130 (or 260) is then inserted into the accessory tube 12 (or 212) while gentle tension is applied to the free ends of the loop of suture (FIG. 28K). The distal end 136 (or 260a) of the suture securing instrument passes through the attachment tip 26 (or 226) and is located near the suture loop extending from the tissue (FIG. 28L). The suture securing instrument 130 (or 260) is positioned adjacent to the tissue, appropriate suture tension applied and the instrument is then actuated as described earlier to crimp and cut the sleeve member (FIG. 28M), and then the instrument 130 (or 260) is removed leaving the crimped sleeve member 174a to close the suture (FIG. 28N). FIG. 29F illustrates the patient after the suture is closed and the suture securing instrument is removed. The gastroscope 14 and attached accessory tube 12 (or 212) remains in the patient during both the suturing and suture securing operations, and this procedure does not require the use of an overtube. If additional suturing is required, the suturing instrument 16 (or 216) may be reloaded with another suture loop and above described procedure repeated with the suture securing instrument reloaded with another sleeve member to secure the suture closed. In this manner, multiple sutures may be made in the stomach tissue with a single insertion of the gastroscope 14. When suturing is completed, the gastroscope 14 and attached accessory tube 12 (or 212) are removed from the patient.

Although the suturing instrument 16 or 216 and suture securing instrument 130 or 260 are described for use with gastroscope 14, these instruments may be used separately from the gastroscope 14 and accessory tube. Further, suturing instrument 16 or 216 and suture securing instrument 130 or 260 may pass through an internal channel 28d (FIG. 1B), often called a working or biopsy channel, provided in gastroscope 14 to its distal end 14a sized to receive the respective shaft of the instrument.

From the foregoing description, it will be apparent that there has been provided an improved system and method for endoscopic suturing. Variations and modifications in the herein described system and method in accordance with the invention will undoubtedly suggest themselves to those skilled in the art. Accordingly, the foregoing description should be taken as illustrative and not in a limiting sense.

What is claimed is:

1. A system for endoscopic suturing of tissue comprising:
an endoscope locatable in the body of a patient having a flexible shaft;
an accessory tube having first and second ends, and coupled along the outside of the shaft of said endoscope to flex in accordance with flexures of said shaft of said endoscope; and
at least one suturing instrument having a shaft insertable via said first of said ends of said tube, a distal tissue engaging end coupled to said shaft of the suturing instrument, one or more needles extendible through said shaft of the suturing instrument to said tissue engaging end, in which said shaft of the suturing instrument has a first section and a second section, said second section extends from said first section to said tissue engaging end, and a flexible needle carrying tube for each of said one or more needles, in which said flexible needle carrying tube extends through at least part of said second section and each of said one or more needles is extendible through their respective needle carrying tube, and said second section has sufficient flexibility to be extendible in said tube to said second of said ends of said tube when said tube has one or more flexures in accordance with one or more flexures of said endoscope.

2. The system according to claim 1 further comprising:
means for attaching said tube at a plurality of locations along said shaft of said endoscope to enable said tube to be substantially coaxial with said shaft of said endoscope while movable through said attaching means.

3. The system according to claim 1 further comprising:
a cannula attached to said first end of said accessory tube having a sealable opening in which said shaft of said suturing instrument passes through cannula to said tube.

4. The system according to claim 1 wherein said suturing instrument has a housing coupled to said shaft and said first section of said shaft is at least partially mounted within said housing.

5. The system according to claim 4 wherein said first section is rigid and extends from said housing, and said second section is flexible and extends from the first section to the tissue engaging end.

6. The system according to claim 5 wherein said first section of said shaft has a rigid tube and said second flexible section has a flexible tubular body, and a first coupler couples said rigid tube and said flexible tubular body, and the needle carrying tube for each of said needles is longitudinally fixed in said first coupler.

7. The system according to claim 6 wherein said flexible section of said shaft in said flexible tubular body further comprises a second coupler, a cable fixed to said second coupler extending to said tissue engaging end and attached to said tissue engaging end, and said second coupler couples the needle carrying tube for each of said needles to said cable.

8. The system according to claim 7 wherein said flexible section of said shaft in said flexible body further comprises a flexible guide member having three channels between said second coupler and said tissue engaging end for carrying said cable and one or more needles, wherein said one or more needles exit said needle carrying tubes prior to said flexible guide member.

9. The system according to claim 8 wherein said second section of said shaft of said suturing instrument between said second and third couplers represents a part of said second section having the greatest flexibility.

10. The system according to claim 7 wherein said tissue engaging end further comprises a third coupler attached to said cable and said flexible body, and a sew tip attached to said third coupler having channels for said one or more needles and a gap across which each of said one or more needles are extendible.

11. The system according to claim 1 wherein said tissue engaging end has a gap through which said one or more needles are extendable through said gap, and said system further comprises means for providing suction through said shaft to said gap of said tissue engaging end to enable tissue to be pulled into said gap prior to extending said one or more needles.

12. The system according to claim 11 wherein said tissue engaging end has channels for distributing said suction along said gap.

13. The system according to claim 11 wherein said suturing instrument further comprises a loop of suture having two ends, two ferrules each coupled to one of said ends of said loop of suture, means for selectably driving each of said one or more needles forward through said suctioned tissue into a different one of said two ferrules, and retracting each of said needles through said suctioned tissue with said ferrule.

14. The system according to claim 13 wherein said suturing instrument further comprises a suture carrying tube extending through said shaft to said tissue engaging end for carrying said loop of suture.

15. The system according to claim 1 wherein said distal tissue engaging end comprises a frame and a plurality of sections which are integrated to said frame.

16. The system according to claim 1 wherein said endoscope is a gastroscope.

17. The system according to claim 1 wherein said one or more needles each have a first diameter and has a plurality of regions of a second diameter less than said first diameter which alternate with regions of said first diameter in at least a portion of said second section to enhance flexibility of said one or more needles.

18. The system according to claim 1 wherein said suturing instrument is separate from said endoscope.

19. The system according to claim 1 further comprising a suture securing instrument having a flexible shaft insertable via said first of said ends of said accessory tube.

20. The system according to claim 19 wherein said suture securing instrument further comprises means for retaining in a sleeve member the two free ends of a loop of suture extending through tissue, and means for cutting the two free ends of the loop of suture near said sleeve member.

21. The system according to claim 19 wherein said suture securing instrument is separate from said endoscope.

22. The system according to claim 1 wherein said endoscope provides means for viewing the suturing instrument.

23. The system according to claim 1 wherein said shaft of said suturing instrument is insertable by said tissue engaging end first entering into said first of said ends of said accessory tube follows by said second section and then said first section until said tissue engaging end extends from said second of said ends of said accessory tube.

24. The system according to claim 1 wherein said one or more needles are extendible through the length of said first section and then along the length of said second section of said shaft.

25. A suturing instrument comprising:
a housing;
a shaft extending from said housing;
a tissue engaging end coupled to said shaft at the distal end of the instrument;
one or more needles which extend through said housing through said shaft to said tissue engaging end;
a suture tube extending through said housing and said shaft to said tissue engaging end;
said tissue engaging end having a sew tip with an opening through which said one or more needles are extendable to each capture one end of suture extending through said suture tube to said sew tip;
said shaft representing an assembly having a first section and a second section coupled to said first section, said first section being rigid and extends from said housing, and said second section being flexible and extends from the first section to the tissue engaging end;
a flexible needle carrying tube for each of said one or more needles, in which said flexible needle carrying tube extends through at least part of said first and second sections of said shaft; and
means for coupling said flexible needle carrying tube for each of said one or more needles by a cable to said tissue engaging ends; and
a flexible guide member having channels for carrying said one or more needles and cable to said tissue engaging end after each said needle exits their respective said needle carrying tube.

26. The suturing instrument of claim 25 further comprising means for providing suction to said opening of said sew tip through said shaft.

27. A system for endoscopic suturing of tissue comprising:
an endoscope locatable in the body of a patient having a flexible shaft;
an accessory tube having first and second ends, and coupled to said endoscope to flex with flexures of said shaft of said endoscope; and
at least one suturing instrument having a shaft locatable through said first and second ends of said tube, a distal tissue engaging end coupled to said shaft, one or more needles extendible through said shaft to said tissue engaging end, in which each of said one or more needles along a portion of the needle undulates between first diameter regions and second diameter regions larger than said first diameter regions to enhance flexibility of said one or more needles.

28. A suturing instrument which is capable of being used with or without an endoscope comprising:
- a shaft having a first end and a second end, and a first section and a second section between said first end and said second end in which at least part of said shaft is substantially flexible;
- a distal tissue engaging end coupled to said second end of said shaft in which said first section extends from said first end of the shaft, and said second section extends from said first section to said second end of the shaft;
- one or more needles extendible through said shaft to said tissue engaging end; and
- a tube for each of said one or more needles, said tube being substantially flexible and extending within at least the flexible part of said shaft, and each of said one or more needles being substantially flexible as each extends through their respective tube.

29. The suturing instrument according to claim 28 wherein said tissue engaging end further comprises a gap through which said one or more needles are extendible.

30. The suturing instrument according to claim 29 further comprising a channel for enabling suction through said shaft to said gap of said tissue engaging end to enable tissue to be pulled into said gap prior to extending said one or more needles, and said tissue engaging end has one or more channels for distributing said suction along said gap.

31. The suturing instrument according to claim 28 wherein said shaft is bendable along the flexible part of said shaft.

32. The suturing instrument according to claim 28 wherein said shaft is not part of any endoscope.

33. The instrument according to claim 28 wherein said needles are two in number, and said tissue engaging end has a gap through which said needles are extendable through said gap, and said instrument further comprises:
- means for providing suction through said shaft to said gap of said tissue engaging end to enable tissue to be pulled into said gap prior to extending said needles;
- a loop of suture having two ends;
- two ferrules each coupled to one of said ends of said loop of suture; and
- means for selectably driving each of said needles forward through said suctioned tissue into a different one of said two ferrules, and retracting each of said needles through said suctioned tissue with said ferrule.

34. The instrument according to claim 28 wherein said one or more needles are extendible through the length of said first section of said shaft and then the length of said second section of said shaft.

35. The instrument according to claim 28 further comprising a proximal member and an opening at one end of said member through which said shaft extends to said distal tissue engaging end in which said first end of said shaft and at least a part of said first section is mounted within said member.

36. The instrument according to claim 28 wherein said proximal member represents a housing having means for controlling movement of said one or more needles along said shaft.

37. The instrument according to claim 28 wherein said at least part of said shaft which is substantially flexible is along said second section of said shaft, and said second section of said shaft is substantially more flexible than said first section of said shaft.

38. A suturing instrument which is capable of being used with or without an endoscope comprising:
- a shaft in which is at least part of said shaft is substantially flexible;
- a distal tissue engaging end coupled to said shaft;
- one or more needles extendible through said shaft to said tissue engaging end; and
- a flexible tube for each of said one or more needles, said flexible tube extending within at least the flexible part of said shaft, and each of said one or more needles being extendible through their respective flexible tube, wherein at least one portion of each of said one or more needles has a first diameter and a plurality of regions which are less in diameter than said first diameter and alternate with regions of said first diameter to enhance flexibility of said one or more needles along said portion with regions of said first diameter to enhance flexibility of said one or more needles along said portion.

39. A suturing instrument which is capable of being used with or without an endoscope comprising:
- a shaft at least a part of which is bent or bendable along the length of the shaft;
- a distal tissue engaging end coupled to said shaft;
- one or more needles extendible through said shaft to said tissue engaging end, at least one portion of each of said one or more needles has a first diameter and a plurality of regions which are less in diameter than said first diameter and alternate with regions of said first diameter to enhance flexibility of said one or more needles along said portion with regions of said first diameter to enhance flexibility of said one or more needles along said portion; and
- said portion of each of said one or more needles passes through said part of said shaft which is bent or bendable.

40. A suturing instrument which is capable of being used with or without an endoscope comprising:
- a shaft in which at least part of said shaft is substantially flexible to bend in response to said shaft following along a substantially curved path in the body of a patient when said shaft is inserted in the body of the patient;
- a tissue engaging end coupled to said shaft;
- two separate needles through said shaft are present at the same time at said tissue engaging end when said shaft is inserted in the body of a patient; and
- each of said needles has one of a substantially flexible tube or member and extends within said tube or member through at least said part of said shaft which is substantially flexible, wherein each of needles is at least substantially flexible through their respective said tube or member.

* * * * *